(12) United States Patent
Sakamoto et al.

(10) Patent No.: US 9,994,816 B2
(45) Date of Patent: Jun. 12, 2018

(54) LRP4/CORIN DOPAMINE-PRODUCING NEURON PRECURSOR CELL MARKER

(71) Applicant: Eisai R&D Management Co., Ltd., Tokyo (JP)

(72) Inventors: Yoshimasa Sakamoto, Kobe (JP); Yuichi Ono, Kobe (JP); Toshio Imai, Kobe (JP); Yasuko Nakagawa, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days. days.

(21) Appl. No.: 14/703,000

(22) Filed: May 4, 2015

(65) Prior Publication Data

US 2015/0299654 A1 Oct. 22, 2015

Related U.S. Application Data

(62) Division of application No. 10/552,485, filed as application No. PCT/JP2005/013453 on Jul. 22, 2005, now abandoned.

(30) Foreign Application Priority Data

Jul. 22, 2004 (JP) .................. 2004-213743
Oct. 29, 2004 (JP) .................. 2004-315060

(51) Int. Cl.
| | | |
|---|---|---|
| *G01N 33/50* | (2006.01) | |
| *C12N 5/0797* | (2010.01) | |
| *C07K 16/28* | (2006.01) | |
| *C12Q 1/68* | (2018.01) | |
| *G01N 33/569* | (2006.01) | |
| *G01N 33/68* | (2006.01) | |
| *A61K 35/30* | (2015.01) | |

(52) U.S. Cl.
CPC ............ *C12N 5/0623* (2013.01); *A61K 35/30* (2013.01); *C07K 16/286* (2013.01); *C12Q 1/6881* (2013.01); *C12Q 1/6883* (2013.01); *G01N 33/5023* (2013.01); *G01N 33/56966* (2013.01); *G01N 33/6896* (2013.01); *C12Q 2600/158* (2013.01); *G01N 2500/00* (2013.01); *G01N 2800/2835* (2013.01)

(58) Field of Classification Search
None
See application file for complete search history.

(56) References Cited

U.S. PATENT DOCUMENTS

| | | |
|---|---|---|
| 5,690,927 A | 11/1997 | Major et al. |
| 6,277,820 B1 | 8/2001 | Rosenthal et al. |
| 7,807,371 B2 * | 10/2010 | Ono .................... C12Q 1/6883 435/6.16 |
| 8,232,052 B2 * | 7/2012 | Ono .................... C12Q 1/6883 435/6.1 |
| 2006/0240432 A1 | 10/2006 | Ono et al. |
| 2010/0323366 A1 | 12/2010 | Ono et al. |

FOREIGN PATENT DOCUMENTS

| | | |
|---|---|---|
| EP | 1 405 909 | 4/2004 |
| JP | 8-509215 | 10/1996 |
| JP | 9-505054 | 5/1997 |
| JP | 10-508487 | 8/1998 |
| JP | 10-508488 | 8/1998 |
| JP | 10-509034 | 9/1998 |
| JP | 11-501818 | 2/1999 |
| JP | 11-506930 | 6/1999 |
| JP | 11-509170 | 8/1999 |
| JP | 11-509729 | 8/1999 |
| JP | 2002-051775 | 2/2002 |
| JP | 2002-504503 | 2/2002 |
| JP | 2002-513545 | 5/2002 |
| JP | 2002-522070 | 7/2002 |
| WO | WO 1994/23754 | 10/1994 |
| WO | WO 1995/12982 | 5/1995 |
| WO | WO 1996/14397 | 5/1996 |
| WO | WO 1996/14398 | 5/1996 |
| WO | WO 1996/14399 | 5/1996 |
| WO | WO 1996/28030 | 9/1996 |
| WO | WO 1996/28174 | 9/1996 |
| WO | WO 1996/39496 | 12/1996 |
| WO | WO 1997/02049 | 1/1997 |
| WO | WO 1999/43286 | 9/1999 |
| WO | WO 1999/56759 | 11/1999 |
| WO | WO 1999/64608 | 12/1999 |
| WO | WO 2000/06700 | 2/2000 |
| WO | WO 2000/09669 | 2/2000 |
| WO | WO 2001/57194 | 8/2001 |
| WO | WO 2001/83715 | 11/2001 |
| WO | WO 2002/074906 | 9/2002 |
| WO | WO 2002/103007 | 12/2002 |

(Continued)

OTHER PUBLICATIONS

Ye et al., Cell, 93:755-766, May 1998.*
Sanchez-Ramos, Ex Neurol., 164:247-256, 2000.*
Barberi, Tiziano, et al; "Neural subtype specification of fertilization and nuclear transfer embryonic stem cells and application in Parkinsonian mice"; Nature Biotechnology; Oct. 2003; pp. 1200-1207; vol. 21, No. 10.
Bjorklund, Lars M., et al; "Embryonic stem cells develop into functional dopaminergic neurons after transplantation in a Parkinson rat model"; PNAS: Proceedings of the National Academy of Sciences of the United States of America; Feb. 19, 2002; pp, 2344-2349; vol. 99, No. 4.

(Continued)

*Primary Examiner* — Kimberly Ballard
*Assistant Examiner* — Stacey N MacFarlane
(74) *Attorney, Agent, or Firm* — Fish & Richardson P.C.

(57) ABSTRACT

The present invention relates to polynucleotide probes and antibodies for detecting Lrp4/Corin dopaminergic neuron progenitor cell markers, which enable the efficient separation of dopaminergic neuron progenitor cells; and methods for selecting the progenitor cells by the use thereof.

9 Claims, 18 Drawing Sheets

(56) References Cited

FOREIGN PATENT DOCUMENTS

| WO | WO 2003/106657 | | 12/2003 | |
|---|---|---|---|---|
| WO | WO/2003/106657 | A1 * | 12/2003 | |
| WO | WO 2004/038018 | | 5/2004 | |
| WO | WO 2004/065599 | | 8/2004 | |
| WO | WO 2004065599 | A1 * | 8/2004 | ........... C12Q 1/6883 |
| WO | WO 2004/081172 | | 9/2004 | |
| WO | WO 2005/052190 | | 6/2005 | |

OTHER PUBLICATIONS

Canadian Office Action for App. Ser. No. 2,574,177, dated Dec. 4, 2012, 2 pages.
Office Action for Israeli counterpart application No. 205193, 2 pages, dated Apr. 22, 2012.
Office Action issued for Chinese Application No. 200580031914.3, 8 pages, dated Feb. 3, 2012 (with English translation).
Office Action issued for Indian counterpart application No. 744/DELNP/2007, 2 pages, dated Mar. 6, 2012.
Office Action issued for Israeli counterpart application No. 180782, 14 pages, dated Mar. 26, 2012.
Office Action issued for the European counterpart application No. 05766437.7, dated Oct. 4, 2012, 5 pages.
Office Action issued for the Korean counterpart application No. 10-2007-7004164, 5 pages, dated Jun. 1, 2012.
Defer, Gilles-Louis, et al; "Long-term outcome of unilaterally transplanted Parkinsonian patients"; Brain; 1996; pp. 41-50; vol. 119.
English translation of Israeli Office Action for App. Ser. No. 205194, dated Feb. 17, 2013, 2 pages.
English translation of Official Notification dated Nov. 7, 2013 for corresponding IL Patent Application No. 205193.
Extended Search Report issued for European Application No. 05766437.7 dated Dec. 1, 2006.
Final Decision issued for Japanese Application No. JP2006-355330 dated Oct. 18, 2010.
Freed, Curt R, et al; "Survival of implanted fetal dopamine cells and neurologic improvement 12 to 46 months after transplantation for Parkinson's disease"; The New England Journal of Medicine; Nov. 26, 1992; pp. 1549-1555; vol. 327, No. 22.
Hearing Notice dated Jun. 4, 2013 for corresponding IN Patent Application No. 744/DELNP/2007.
Hooper, John D., et al; "Localization of the mosaic transmembrane serine protease corin to heart myocytes"; The FEBS Journal (Formerly European Journal of Biochemistrvl; 2000; pp. 6931-6937; vol. 267.
International Search Report issued for International Application No. PCT/JP05/013453 dated Oct. 25, 2005.
Kawasaki, Hirosh, et al.; "Induction of midbrain dopaminergic neurons from ES cells by stroma cell-derived inducing activity;" Neuron; Oct. 2000; pp. 31-40; 28:1.
Kawasaki, Hiroshi, et al.; "Generation of dopaminergic neurons and pigmented epithelia from primate ES cells by stromal cell-derived inducing activity"; PNAS: Proceedings of the National Academy of Sciences of the United States of America; Feb. 5, 2002; pp, 1580-1585; vol. 99, No. 3.
Kim, Jong-Hoon, et al.; "Dopamine neurons derived from embryonic stem cells function in an animal model of Parkinson's disease"; Nature; Jul. 4, 2002; pp. 50-56; vol. 418.
Kordower, Jeffrey ., et al; "Neuropathological evidence of graft survival and striatal reinnervation after the transplantation of fetal mesencephalic tissue in a patient with Parkinson's disease"; The New England Journal of Medicine; Apr. 27, 1995; pp. 1118-1124; vol. 332, No. 17.
Korean Office Action for App. Ser. No. 10-2007-7004164, dated Feb. 14, 2013, 8 pages (and English translation).
Lee, Sang-Hun, et al; "Efficient generation of midbrain and hindbrain neurons from mouse embryonic stem cells"; Nature Biotechnology; Jun. 2000; pp. 675-679; vol. 18, No. 6.
Li, Yonghe, et al.; "Low-Density Lipoprotein Receptor Family;" Molecular Neurobiology; Feb. 23, 2001; pp. 53-67; 23:1.
Lindvall, Olle, et al.; "Human fetal dopamine neurons grafted into the striatum in two patients with severe Parkinson's disease"; Archives of Neurology; Jun. 1989; pp. 615-631; vol. 46, No. 6.
Lopez-Lozano, J, J. et al; "Regression of Parkinsonian fetal ventral Mesencephalon grafts upon withdrawal of Cyclosporine A immunosuppression"; Transplantation Proceedings; Feb.-Mar. 1997; pp. 977-980; vol. 29, Nos. 1-2.
NCB I Accession No, AB013874, "Mus musculus mRNA for Low Density Lipoprotein Receptor Related Protein 4," 3 pgs. (Nov. 11, 1998).
Okazaki et aI., "Analysis of the mouse transcriptome based on functional annotation of 60,770 full-length cDNAs", Nature, 240(6915):563-573, Dec. 5, 2002.
Response filed on Mar. 9, 2014 for corresponding IL Patent Application No. 205193.
Response filed on May 16, 2014 for corresponding CA patent application No. 2574177.
Response to Office Action for corresponding EP Application No. 05 76 6437.7-1402 dated Jul. 22, 2014.
Response to Office Action for corresponding CA Application No. 2574177 dated Mar. 30, 2015.
Sakamoto, Yoshimasa, et al.; "Saibomaku hyomen maker 0 mochiita dopamine sansei neuron zenku saibo no bunri"; Annual Meeting of the Molecular Biology Society of Japan Program; Nov. 25, 2004, p. 762; vol. 27.
Sawamoto, Kazunobu, et al.: "Generation of dopaminergic neurons in the adult brain from mesencephalic precursor cells labeled with a nestin-GFP transgene"; The Journal of Neuroscience; Jun. 1, 2001; pp. 3895-3903; vol. 21, No. 11.
Sawamoto, Kazunobu, et al.: "Visualization, direct isolation, and transplantation of midbrain dopaminergic neurons"; PNAS: Proceedings of the National Academy of Sciences of the United States of America; May 22, 2001; pp. 6423-6428; vol. 98, No. 11.
Selawry, H, P, and D, F, Cameron; "Sertoli cell-enriched fractions in successful islet cell transplantation"; Cell Transplantation; Mar.-Apr. 1993; pp, 123-129; vol. 2, No. 2.
Spencer, Dennis D et al.; "Unilateral transplantation of human fetal mesencephalic tissue into the caudate nucleus of patients with Parkinson's disease"; The New England Journal of Medicine; Nov. 26, 1992; pp. 1541-1548; vol. 327, No. 22.
Studer, Lorenz, et al., "Transplantation of expanded mesencephalic precursors leads to recovery in Parkinsonian rats"; Nature Neuroscience; Aug. 1998; pp. 290-295: vol. 1, No. 4.
Submissions filed after Hearing of Sep. 13, 2013 for corresponding in Patent Application No. 744/DELNP/2007.
Submissions filed on Sep. 12, 2013 at a Hearing for the corresponding in Patent Application No. 744/DELNP/2007.
Suggs et al., 1981, "Use of synthetic oligonucleotides as hybridization probes: isolation of cloned cDNA sequences for human beta 2-microglobulin," Proc. Natl. Acad. Sci. USA 78(11):6613-17.
Tomita, Yasuhiro, et al.; "A Novel Low-Density Lipoprotein Receptor-Related Protein with Type II Membrane Protein-Like Structure Is Abundant in Heart;" Japanese Biochemistry; Oct. 1998; pp. 784-789; 124:4.
Widner, Hakan, et al.: "Bilateral fetal mesencephalic grafting in two patients with Parkinsonism induced by 1-methyl-4-phenyl-1,2,3,6-tetrahydropyridine (MPTP)", The New England J Medicine; Nov. 26, 1992; pp. 1556-1563; vol. 327, No. 22.
Yan, Wei, et al., "Corin, a Mosaic Transmembrane Serine Protease Encoded by a Novel cDNA from Human Heart"; The Journal of Biological Chemistry; May 21, 1999; pp. 14926-14935; vol. 274, No. 21.
Yoshizaki, Takahito, et al,; "Isolation and transplantation of dopaminergic neurons generated from mouse embryonic stem cells"; Neuroscience Letters; Jun. 3, 2004; pp. 33-37; vol. 363, No. 1.
Zhang et al. J Biol Chem, 289(19):19115-19126, Jan. 28, 2005.
Zhao, Suling, et al,; "Generation of embryonic stem celis and transgenic mice expressing green fluorescence protein in midbrain dopaminergic neurons"; European Journal of Neuroscience; Mar. 2004; pp. 1133-1140; vol. 19, No. 5.

(56) References Cited

OTHER PUBLICATIONS

Zigova, et al., "Neuronal Progenitor Cells of the Neonatal Subventricular Zone Differentiate and Disperse Following Transplantation Into the Adult Rat Striatum," Cell Transplantation, vol. 7, Issue 2, pp. 137-156 (Mar.-Apr. 1998).
Office Action issued in Canadian Application No. 2574177, dated Sep. 28, 2016, 3 pages.
Office Action in Canadian Application No. 2574177, dated Aug. 2, 2017, 3 pages.
Response to Office Action filed on Mar. 28, 2017 for corresponding Canadian Patent Application No. 2574177, 13 pages.
Office Action issued in Canadian App. No. 2574177, dated Dec. 4, 2012, 2 pages.
Office Action issued in Canadian App. No. 2574177, dated Nov. 21, 2013, 3 pages.
Office Action issued in Canadian App. No. 2574177, dated Sep. 30, 2014, 3 pages.
Office Action issued in Canadian App. No. 2574177, dated Aug. 2, 2017, 9 pages.
Office Action issued in Canadian App. No. 2574177, dated Oct. 9, 2015, 3 pages.
Office Action issued for Australian Application No. 2005264579 dated Dec. 9, 2005, 3 pages.
Office Action issued for Canadian Application No. 2,574,177 dated Nov. 21, 2011, 5 pages.
Office Action issued for Chinese Application No. 200580031914.3 dated Aug. 21, 2009, 12 pages (English Translation).
Office Action issued for Chinese Application No. 200580031914.3 dated Mar. 9, 2011, 6 pages (English Translation).
Office Action issued for Chinese Application No. 200580031914.3 dated Nov. 6, 2009, 15 pages (English Translation).
Office Action issued for European Application No. 05766437.7 dated Apr. 2, 2014, 4 pages.
Office Action issued for European Application No. 05766437.7 dated Feb. 3, 2011, 5 pages.
Office Action issued for European Application No. 05766437.7 dated Mar. 16, 2007, 5 pages.
Office Action issued for European Application No. 05766437.7 dated Nov. 6, 2009, 4 pages.
Office Action issued for Israeli Application No. 180782 dated Oct. 10, 2010, 3 pages (English Translation).
Office Action issued for Israeli Application No. 180782 dated Sep. 30, 2009, 3 pages (English Translation).
Office Action issued for Israeli Application No. 205193 dated Oct. 10, 2010, 4 pages (English Translation).
Office Action issued for Israeli Application No. 205194 dated Oct. 10, 2010, 4 pages (English Translation).
Office Action issued for Israeli Application No. 205195 dated Oct. 10, 2010, 4 pages (English Translation).
Office Action issued for Japanese Application No. JP2006-355330 dated Aug. 27, 2009, 11 pages (English Translation).
Office Action issued for Japanese Application No. JP2006-355330 dated Feb. 9, 2011, 4 pages (English Translation).
Office Action issued for Japanese Application No. JP2006-355330 dated Jun. 9, 2010, 13 pages (English Translation).
Office Action issued for Japanese Application No. JP2006-524554 dated Mar. 7, 2007, 10 pages (English Translation).
Office Action issued for Japanese Application No. JP2006-524554 dated Nov. 1, 2006, 10 pages (English Translation).
Office Action issued for Japanese Application No. JP2007-121660 dated Aug. 27, 2009, 14 pages (English Translation).
Office Action issued for Japanese Application No. JP2007-121660 dated Jun. 9, 2010, 7 pages (English Translation).
Office Action issued for Singapore Application No. 200700561-4 dated Mar. 6, 2008, 6 pages (English Translation).
Response to Office Action filed in Canadian Application No. 2574177, dated Apr. 8, 2016, 13 pages.
Response to Office Action filed in Canadian Application No. 2574177, dated Jan. 29, 2018, 9 pages.

\* cited by examiner

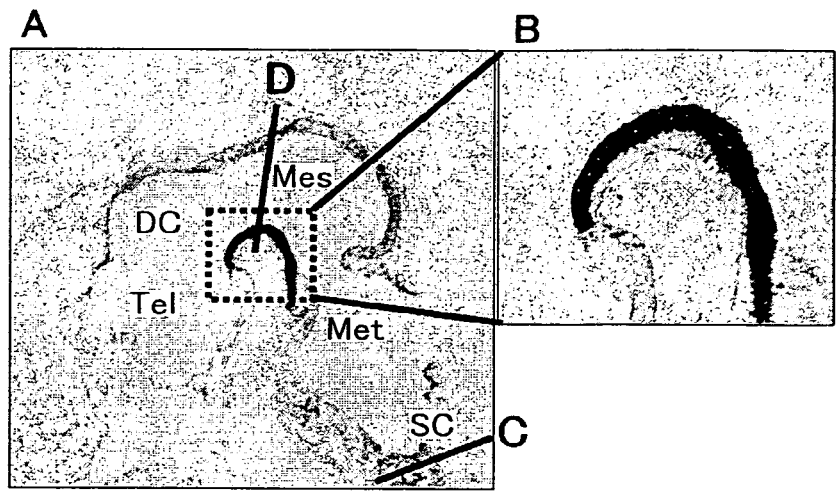
C. SPINAL CORD
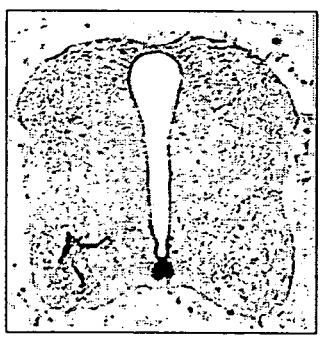
D. MIDBRAIN
Lrp4     TH
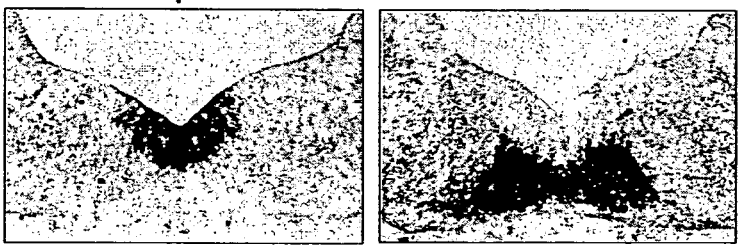
Shh
FIG. 5

LRP4/CORIN DOPAMINE-PRODUCING NEURON PRECURSOR CELL MARKER

TECHNICAL FIELD

The present invention relates to polynucleotide probes and antibodies for detecting and selecting dopaminergic neuron progenitor cells, and methods for detecting and selecting dopaminergic neuron progenitor cells by using them, and kits and therapeutic methods for treating neurodegenerative diseases such as Parkinson's disease using dopaminergic neuron progenitor cells.

BACKGROUND ART

The dopamine system is an extremely important system for essential motor regulation, hormone secretion regulation, emotion regulation, and such in the mammalian brain. Thus, abnormalities in dopaminergic neural transmission cause various neural disorders. For example, Parkinson's disease is a neurodegenerative disease of the extrapyramidal system that occurs due to specific degeneration of dopaminergic neurons in the substantia nigra of the midbrain (Harrison's Principles of Internal Medicine, Vol. 2, 23rd edition, Isselbacher et al., ed., McGraw-Hill Inc., NY (1994), pp. 2275-7). As a primary therapeutic method for Parkinson's disease, oral administration of L-DOPA (3,4-dihydroxyphenylalanine) is performed to compensate for the decrease in the amount of dopamine produced; however, the duration of the effect is known to be unsatisfactory.

More recently, a therapeutic method for Parkinson's disease was attempted in which the midbrain ventral regions of 6 to 9-week old aborted fetuses containing dopaminergic neuron progenitor cells are transplanted to compensate for the loss of dopaminergic neurons (Patent Document 1; and Non-Patent Documents 1 to 6). However, in addition to cell supply and ethical issues (Rosenstain (1995) Exp. Neurol. 33: 106; Turner et al. (1993) Neurosurg. 33: 1031-7), this method is currently under criticism for various other problems, including risk of infection and contamination, immunological rejection of transplants (Lopez-Lozano et al. (1997) Transp. Proc. 29: 977-980; Widner and Brudin (1988) Brain Res. Rev. 13: 287-324), and low survival rates due to the primary dependence of fetal tissues on lipid metabolism rather than glycolysis (Rosenstein (1995) Exp. Neurol. 33: 106).

In order to resolve the ethical issues and shortage of supply, methods have been proposed that use, for example, porcine cortex, stria, and midbrain cells (for example, see Patent Documents 2 to 4). In these methods, a complex procedure that involves altering cell surface antigens (MHC class I antigens) is required to suppress rejection. A method involving local immunosuppression by simultaneously transplanting Sertoli's cells has been proposed as a method for eliminating transplant rejection (Patent Documents 5 and 6; and Non-Patent Document 7). It is possible to obtain transplant cells from relatives that have matching MHCs, bone marrow from other individuals, bone marrow banks, or umbilical cord-blood banks. However, if it were possible to use the patient's own cells, the problem of rejection reactions could be overcome without any laborious procedures or trouble.

Therefore, as transplant materials, the use of dopaminergic neurons differentiated in vitro from non-neural cells such as embryonic stem (ES) cells and bone marrow interstitial cells, instead of cells from aborted fetuses, is considered to be promising. In fact, functional dopaminergic neurons were reported to have been formed by transplanting ES cells to lesion stria of a rat Parkinson's disease model (Non-Patent Document 8). It is believed that the importance of regenerative therapy from ES cells or the patient's own nerve stem cells will increase in the future.

In treating damaged nerve tissue, it is necessary to reconstruct brain function, and in order to form a suitable link with surrounding cells (network formation), it is necessary to transplant immature cells, cells capable of differentiating into neurons in vivo. In the transplanting of neuron progenitor cells, in addition to the aforementioned problem regarding supply, there is also the possibility that the progenitor cells will differentiate into groups of heterogeneous cells. For example, in treating Parkinson's disease, it is necessary to selectively transplant the catecholamine-containing neurons that produce dopamine. Examples of transplant cells that have previously been proposed for use in the treatment of Parkinson's disease include striatum (Non-Patent Documents 3 and 9), immortalized cell lines derived from human fetal neurons (Patent Documents 7 to 9), human postmitotic neurons derived from NT2Z cells (Patent Document 10), primordial neuron cells (Patent Document 11), cells and bone marrow stroma cells transfected with exogenous genes so as to produce catecholamines such as dopamines (Patent Documents 12 and 13), and genetically engineered ES cells (Non-Patent Document 8). Additionally, the use of dopaminergic neurons formed by contacting nerve progenitor cells derived from fetal midbrain tissue with FGF-8 and Shh (Patent Document 14), and of tyrosine hydroxylase-expressing cells obtained by treating NT2 nerve cells with retinoic acid (Patent Document 15) has been proposed. However, none of these contain only dopaminergic neurons or cells that differentiate into dopaminergic cells.

A method has been proposed for selectively concentrating and isolating dopaminergic neurons from undifferentiated cell populations. In this method, a reporter gene that expresses a fluorescent protein is introduced into each cell of a cell population, under the control of a gene promoter/enhancer such as the tyrosine hydroxylase expressed in dopaminergic neurons (hereinbelow, also referred to as "TH"), and then cells emitting fluorescence are isolated. The dopaminergic neurons are visualized in their viable state, then concentrated, isolated, and identified (Patent Document 16). This method requires the complicated step of introducing an exogenous gene, and further, the presence of a reporter gene poses problems of toxicity and immunogenicity when used in conjunction with gene therapy.

[Patent Document 1] U.S. Pat. No. 5,690,927
[Patent Document 2] Japanese Patent Kohyo Publication No. (JP-A) H10-508487 (unexamined Japanese national phase publication corresponding to a non-Japanese international publication)
[Patent Document 3] JP-A H10-508488
[Patent Document 4] JP-A H10-509034
[Patent Document 5] JP-A H11-509170
[Patent Document 6] JP-A H11-501818
[Patent Document 7] JP-A H8-509215
[Patent Document 8] JP-A H11-506930
[Patent Document 9] JP-A 2002-522070
[Patent Document 10] JP-A H9-5050554
[Patent Document 11] JP-A H11-509729
[Patent Document 12] JP-A 2002-504503
[Patent Document 13] JP-A 2002-513545
[Patent Document 14] U.S. Pat. No. 6,277,820
[Patent Document 15] International Publication WO 00/06700

[Patent Document 16] Japanese Patent Application Kokai Publication No. (JP-A) 2002-51775 (unexamined, published Japanese patent application)

[Non-Patent Document 1] Spencer et al. (1992) N. Engl. J. Med. 327: 1541-8

[Non-Patent Document 2] Freed et al. (1992) N. Engl. J. Med. 327: 1549-55

[Non-Patent Document 3] Widner et al. (1992) N. Engl. J. Med. 327: 1556-63

[Non-Patent Document 4] Kordower et al. (1995) N. Engl. J. Med. 332: 1118-24

[Non-Patent Document 5] Defer et al. (1996) Brain 119: 41-50

[Non-Patent Document 6] Lopez-Lozano et al. (1997) Transp. Proc. 29: 977-80

[Non-Patent Document 7] Selawry and Cameron (1993) Cell Transplant 2: 123-9

[Non-Patent Document 8] Kim et al. (2002) Nature 418: 50-56

[Non-Patent Document 9] Lindvall et al. (1989) Arch. Neurol. 46: 615-31

DISCLOSURE OF THE INVENTION

Problems to be Solved by the Invention

One of the major problems in Parkinson's disease transplantation therapy at the moment is that both in vitro differentiated dopaminergic neuron precursor cells and midbrain ventral region of aborted fetuses are mixtures of a myriad cell types. When considering safety in neural circuit formation, it is preferable to use isolated cells that comprise only the cell type of interest. Furthermore, when considering the risk of tumorigenesis, it is believed better to use isolated postmitotic neurons. Moreover, when considering the survival of cells at their transplantation site in the brain, and their ability to properly form a network, it is expected that therapeutic effects can be further improved by isolating dopaminergic neuron progenitor cells at as early a stage as possible.

Means to Solve the Problems

In order to isolate genes specific to dopaminergic neuron progenitor cells, a gene specifically expressed in the most ventral region of the E12.5 murine midbrain containing dopaminergic neurons was identified using a modification ("Method for Homogenizing the Amounts of DNA Fragments and Subtraction Method", WO 2002/103007 (International Publication Pamphlet)) of the subtraction method (N-RDA: Representational Difference Analysis; RDA (Listsyn N. A. (1995) Trends Genet. 11: 303-7) by additionally dividing the ventral region into two regions in the dorsoventral direction. As a result, the present inventors successfully isolated Lrp4/Corin. Lrp4 encoded a type II transmembrane protein (FIG. 1).

Lrp4 mRNA is specifically expressed in a ventral midline region in the midbrain. The areas where Lrp4 mRNA is expressed match the areas where dopaminergic neuron proliferative progenitor cells are present. Furthermore, when Lrp4 expression is compared to that of TH, which is a marker for dopaminergic neurons, their signals are in identical dorsoventral positions, but they do not overlap (FIGS. 4 and 5). This indicated that Lrp4 mRNA is not expressed in these progenitor cells, which had stopped cell division and migrated to the neural tube outer layer. Therefore, by using Lrp4 mRNA as an index, it is possible to specifically detect and select dopaminergic neuron proliferative progenitor cells.

Thus, the present invention provides dopaminergic neuron proliferative progenitor cell marker polynucleotide probes capable of specifically detecting Lrp4 mRNA, and methods for selecting dopaminergic neuron proliferative progenitor cells utilizing these probes. Furthermore, the present invention relates to dopaminergic neuron proliferative progenitor cells prior to cell cycle exit, selected by using such nucleotide probes (hereinbelow, sometimes referred to simply as "dopaminergic neuron proliferative progenitor cells"); as well as methods for isolating dopaminergic neuron proliferative progenitor cell-specific genes and genes specific for each maturation stage from progenitor cell to dopaminergic neuron, utilizing the proliferative progenitor cells; and methods of screening for compounds which induce differentiation or proliferation of the progenitor cells, using maturation as an index. It is also possible to culture the proliferative progenitor cells selected by using the nucleotide probes of the present invention, and to obtain dopaminergic neuron lineage cells comprising the postmitotic dopaminergic neuron precursor cells. The term "dopaminergic neuron lineage cells" used herein refers to dopaminergic neuron proliferative progenitor cells, postmitotic dopaminergic neuron precursor cells, and/or dopaminergic neurons. The dopaminergic neuron lineage cells can also be utilized for the methods for isolating genes specific to each stage of maturation to dopaminergic neuron, and the methods of screening for compounds which induce the differentiation or proliferation of progenitor cells, using maturation as an index. Therefore, the present invention relates to methods for obtaining the dopaminergic neuron lineage cells by culturing the dopaminergic neuron proliferative progenitor cells selected by using the nucleotide probes of the present invention; cells obtained in this way; methods for isolating genes specific to each stage of maturation to dopaminergic neurons that use the cells; and methods of screening for compounds which induce the differentiation or proliferation of the cells using maturation as an index.

Furthermore, the present inventors produced an anti-Lrp4 antibody, and examined Lrp4 protein expression. First, by analyzing its expression in tissues (FIG. 8), the Lrp4 protein was confirmed to be expressed in the same way as Lrp4 mRNA. In this experiment, Lrp4 protein signals were also detected in TH-expressing areas. However, since the proliferative progenitor cells extend processes toward the outer layer of the neural tube, this signal could not be determined to be caused by detecting proteins on the processes or the TH-expressing cells also expressed the Lrp4 protein. Next, by using the anti-Lrp4 antibody, whether Lrp4 protein was expressed on the cell surface was analyzed by flow cytometry. Cells in which Lrp4 mRNA expression was confirmed were obtained by inducing the differentiation of ES cells into dopaminergic neuron progenitor cells in vitro (SDIA method), and used as samples. As a result, it was confirmed that the Lrp4 protein was certainly expressed on the surface of the cells (FIG. 9). Such proteins expressed on the cell surface are particularly preferable to use as separation markers because living cells can be selected (see FIG. 15). In addition, ES cells were induced to differentiate in vitro into the dopaminergic neuron progenitor cells by the 5-stage method, and Lrp4 expression was confirmed by RT-PCR and flow cytometry using the anti-Lrp4 monoclonal antibody. As a result, Lrp4 was revealed to also be expressed in dopaminergic neuron progenitor cells differentiated by the 5-stage method (FIGS. 17A and 17B).

Next, Lrp4-positive cells were separated from cells induced to differentiate (SDIA method) and from mouse fetal ventral midbrain cells by a cell sorter using the anti-Lrp4 antibody. Gene expression in the separated cells was analyzed by the RT-PCR method. As a result, expression of the neuron proliferative progenitor cell marker Nestin was observed. In addition, cells expressing MAP2, which is a marker for postmitotic neurons, were also revealed to be included (FIG. 10). TH and Nurr1, which is a marker for postmitotic dopaminergic neuron precursor cells, were expressed at higher levels in an Lrp4-positive cell population than in an Lrp4-negative cell population. Therefore, unlike in the case of using Lrp4 mRNA as the index, when cells are selected using antibodies by using Lrp4 protein as an index, it is possible to isolate the dopaminergic neuron progenitor cells, including postmitotic dopaminergic neuron precursor cells. Hereinbelow, the term "dopaminergic neuron progenitor cells" refers to dopaminergic neuron proliferative progenitor cells and postmitotic dopaminergic neuron precursor cells. For cells separated using the anti-Lrp4 antibody from those cells induced to differentiate from the ES cells in vitro by the SDIA method, the expression of ERas and Nanog expressed specifically in the ES cells was analyzed. As a result, expression was not observed in Lrp4-positive cells, whereas expression of both genes was observed in Lrp4-negative cells (FIG. 18). Therefore, by selecting cells using the anti-Lrp4 antibody, it is possible to select and remove undifferentiated ES cells after inducing differentiation. Furthermore, Lrp4-positive cells were separated from cell populations including dopaminergic neuron progenitor cells induced to differentiate in vitro from ES cells by the 5-stage method. Next, the separated Lrp4-positive cells were cultured in vitro to induce TH protein-positive dopaminergic neurons (FIG. 17C). This revealed that Lrp4-positive cells induced by the 5-stage method are dopaminergic neuron progenitor cells and can mature in vitro.

Accordingly, the present invention provides antibodies which specifically detect the Lrp4 protein and methods that utilize the antibodies to select dopaminergic neuron progenitor cells. Furthermore, the present invention relates to dopaminergic neuron progenitor cells selected by using such antibodies; as well as methods that use the progenitor cells to isolate dopaminergic neuron progenitor cell-specific genes and genes specific for each maturation stage from progenitor cell to dopaminergic neuron; and methods of screening for compounds which induce the differentiation or proliferation of the progenitor cells using maturation as an index. It is also possible to obtain dopaminergic neuron lineage cells at other differentiation stages by culturing the progenitor cells selected using the antibodies of the present invention. Such cells can also be utilized in the methods for isolating genes specific to each stage of maturation to dopaminergic neuron, and the methods of screening for compounds which induce the differentiation or proliferation of the progenitor cell using maturation as an index. Accordingly, the present invention also relates to methods for obtaining dopaminergic neuron lineage cells by culturing dopaminergic neuron progenitor cells selected using the antibodies of the present invention; cells obtained using the methods; methods that use the cells to isolate genes specific to each stage of maturation to dopaminergic neurons; and methods of screening for compounds which induce the differentiation or proliferation of the cells using maturation as an index.

Furthermore, the present inventors transplanted Lrp4-expressing cells separated using the anti-Lrp4 monoclonal antibody into the striatum of Parkinson's disease model mice. As a result, EGFP-positive cells were observed in the striatum of transplanted mice (Table 1). Thus it appears that the transplanted Lrp4 protein-positive cells were successfully engrafted in the striatum of the Parkinson's disease model mice. Most of the successfully engrafted cells were positive for the mature neuron marker MAP2, and EGFP-positive axons were observed to extend into the striatum (Table 1 and FIG. 16). Most of the successfully engrafted cells differentiated into nerve cells and then matured, whereas the transplanted Lrp4 protein-positive cells were neural progenitor cells, and about 20% of the successfully engrafted cells were TH-positive. These findings strongly suggested that at least some of the transplanted Lrp4 protein-positive cells differentiated into dopaminergic neurons. Therefore, the dopaminergic neuron progenitor cells separated according to the present invention can differentiate into dopaminergic neurons upon being transplanted in to the brain, and may be effective for the treatment of Parkinson's disease. That is, the present invention also relates to kits for treating neurodegenerative diseases, preferably Parkinson's disease, comprising the dopaminergic neuron progenitor cells separated according to the present invention; and methods for treating neurodegenerative diseases, preferably Parkinson's disease, comprising the step of transplanting dopaminergic neuron progenitor cells into the brains of patients.

Effects of the Invention

There have been no previous reports of genes encoding membrane proteins specifically expressed in dopaminergic neuron proliferative progenitor cells. Antibodies to Lrp4 protein expressed on the cell membrane surface are believed to be extremely effective in isolating dopaminergic neuron progenitor cells. For example, pure dopaminergic neuron progenitor cells can be obtained by isolating Lrp4-expressing cells from the ventral midbrain region or cultured cells containing dopaminergic neuron progenitor cells differentiated in vitro, using anti-Lrp4 antibodies (FIG. 15). Lrp4 expression was confirmed on both of the dopaminergic neuron progenitor cells induced by two different differentiation methods (SDIA method and 5-stage method). Accordingly, Lrp4 is useful as a dopaminergic neuron progenitor cell marker, regardless of cell source. In addition, since ERas and Nanog, which are specifically expressed in ES cells, are not expressed in Lrp4-positive cells, it is possible to select undifferentiated ES cells using Lrp4 expression as an index.

Moreover, in the present invention, the isolated dopaminergic neuron progenitor cells can also be transplanted directly, or after having been grown in vitro. The dopaminergic neuron progenitor cells of the present invention also have the potential to differentiate and mature at the optimum region in the brain, as well as the potential to additionally grow in vivo, and can be expected to demonstrate long-term therapeutic effects. In addition, if Lrp4-expressing cells are transplanted after having differentiated and matured in vitro, they can be expected to demonstrate therapeutic effects, even if for some reason they do not differentiate into dopaminergic neurons in vivo. In consideration of the risks of tumorigenesis and such, an even higher degree of safety can be expected if cells that have been isolated using a postmitotic dopaminergic neuron precursor cell marker such as 65B13 (WO 2004/038018 pamphlet) after differentiating Lrp4-expressing cells grown in vitro are transplanted. The use of Lrp4-expressing cells for transplantation therapy after being isolated, regardless of the method, enables a high degree of safety since only the cell type of interest is isolated. In addition, since the earliest dopaminergic neuron progenitor cells can be used, high therapeutic efficacy can be expected in terms of survival rate, network formation ability, and such. Further, even if the best therapeutic effects cannot be achieved by these early progenitor cells immediately after isolation, since progenitor cells isolated using markers of the present invention can mature in vitro by culturing or such, materials in the optimum stage of differentiation can be prepared (FIG. 6).

On the other hand, pure dopaminergic neuron progenitor cells are also useful in the search for therapeutic targets for Parkinson's disease, such as for use in the isolation of genes specific to dopaminergic neurons. In particular, dopaminergic neuron proliferative progenitor cells are useful for research on the maturation process of dopaminergic neurons, screening systems using maturation as an index, drug screening in which progenitor cells are grown in vitro or in vivo, screening for drugs that induce differentiation of progenitor cells in vivo (in vivo regenerative therapy drugs), and the like.

BRIEF DESCRIPTION OF THE DRAWINGS

FIG. 5 is a set of photographs showing the results of Lrp4 mRNA expression analysis in the E12.5 mouse central nervous system by in situ hybridization. A: sagittal cross-section, B: enlarged photograph of the area inside the box in A, C: cross-section at the location of the red line in A, D: Expression of Lrp4, Shh, and tyrosine hydroxylase (TH) mRNA in the E12.5 mouse midbrain ventral region.

BEST MODE FOR CARRYING OUT THE INVENTION

Figure 1:
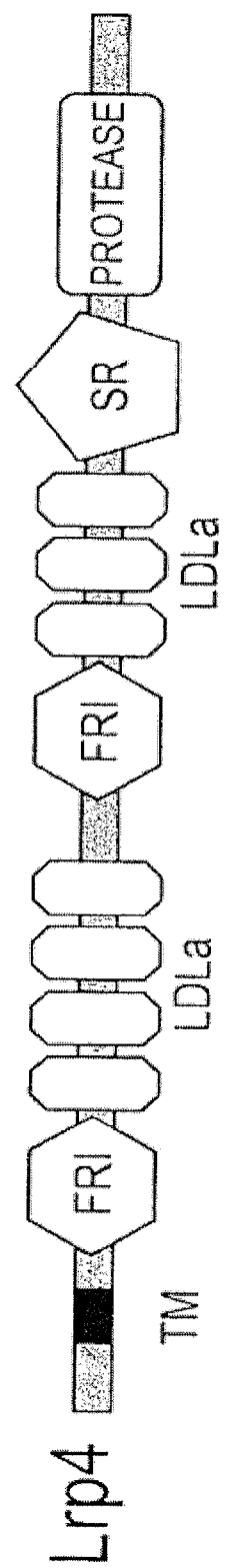
FIG. 1 schematically shows the structure of Lrp4. TM: transmembrane domain, FRI: frizzeled domain, LDLa: LDL receptor domain, SR: scavenger receptor domain, Protease: serine protease domain.

Hereinbelow, the embodiments of the present invention will be described, but they are exemplified to illustrate the present invention, and not to limit the present invention to these embodiments. The present invention can be carried out in various forms without departing from the scope thereof.

References, publications, patent publications, and patent references cited herein are incorporated by reference.

<Marker Polynucleotide Probes>

The dopaminergic neuron proliferative progenitor cell marker polynucleotide probes of the present invention are used as markers and/or reagents for selecting and/or detecting dopaminergic neuron proliferative progenitor cells. Polynucleotides used for this probe comprise a nucleotide sequence complementary to the nucleotide sequence of SEQ ID NO: 1 or 2 detected in dopaminergic neuron proliferative progenitor cells. SEQ ID NO: 1 is the nucleotide sequence of murine Lrp4 cDNA. SEQ ID NO: 2 is the nucleotide sequence of human Lrp4 cDNA. Both sequences are registered in GenBank (murine: Accession No. NM_016869; human: Accession No. XM_035037).

Here, a "marker polynucleotide probe" refers to a polymer composed of a number of nucleotides, such as deoxyribonucleic acids (DNAs) or ribonucleic acids (RNAs), or nucleotide pairs, where the polymer should be able to detect expression of Lrp4, particularly transcribed mRNA. Double-stranded cDNAs are also known to be able to be used as probes in tissue in situ hybridization, and such double-stranded cDNAs are included in the markers of the present invention. RNA probes (riboprobes) are particularly preferable as marker polynucleotide probes for detecting RNAs in tissue. If needed, the marker polynucleotide probes of the present invention can also contain non-naturally-occurring nucleotides such as 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl)threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, and 3-(3-amino-3-carboxy propyl)uridine.

Moreover, marker polynucleotide probes of the present invention comprise nucleotide sequences complementary to nucleotide sequences encoding the amino acid sequence of SEQ ID NO: 3 or 4. The nucleotide sequence that encodes the amino acid sequence of SEQ ID NO: 3 or 4 includes not only nucleotide sequences of SEQ ID NO: 1 or 2, but also nucleotide sequences that differ from the sequences of SEQ ID NO: 1 or 2 due to degeneracy of the genetic code. The marker polynucleotide probes of the present invention also include those which comprise sequences complementary to nucleotide sequences encoding a sequence that lacks the transmembrane domain in the amino acid sequence of SEQ ID NO: 3 or 4. There is no signal sequence in the amino acid sequence of SEQ ID NO: 3 or 4. In murine Lrp4 (SEQ ID NO: 3), amino acid residues 113-135 form a transmembrane domain, while in human Lrp4 (SEQ ID NO: 4), amino acid residues 46-68 form a transmembrane domain. The sequences described in SEQ ID NOs: 3 and 4 are respectively registered in GenBank (human Lrp4, XP_035037; murine Lrp4, NP_058565).

Herein, the phrase "complementary to a nucleotide sequence" encompasses not only cases wherein a nucleotide sequence completely pairs with the template, but also includes those that have at least 70%, preferably 80%, more preferably 90%, and even more preferably 95% or more (for example, 97% or 99%) of the nucleotides paired with the template. Pairing refers to the formation of a chain in which T (U in the case of RNAs) corresponds to A, A corresponds to T or U, G corresponds to C, and C corresponds to G in the nucleotide sequence of the template polynucleotide. Homologies at the nucleotide sequence level between certain polynucleotides can be determined by the BLAST algorithm (Altschul (1990) Proc. Natl. Acad. Sci. USA 87: 2264-8; Karlin and Altschul (1993) Proc. Natl. Acad. Sci. USA 90: 5873-7). The BLASTN program for nucleotide sequences (Altschul et al. (1990) J. Mol. Biol. 215: 403-410) has been developed based on this algorithm, and can be used to determine the homology of marker polynucleotide probe sequences (see http://www.ncbi.nlm.nih.gov for a specific example of analysis methods).

Moreover, marker polynucleotide probes of the present invention include polynucleotides that contain nucleotide sequences that hybridize under stringent conditions with polynucleotides comprised of the nucleotide sequence of SEQ ID NO: 1 or 2. Although polynucleotides with a nucleotide sequence indicated in SEQ ID NO: 1 or 2 are known with respect to Lrp4, alternative isoforms and allelic variants may also exist. Polynucleotides with a sequence complementary to such isoforms and allelic variants can also be used as marker polynucleotides of the present invention. Such isoforms and allelic variants can be obtained from cDNA libraries or genomic libraries derived from animals such as humans, mice, rats, rabbits, hamsters, chickens, pigs, cows, goats, and sheep, by using a polynucleotide probe comprising a nucleotide sequence of SEQ ID NO: 1 or SEQ ID NO: 2, in known hybridization methods such as colony hybridization, plaque hybridization, or Southern blotting. See "Molecular Cloning, A Laboratory Manual 2nd ed." (Cold Spring Harbor Press (1989)) for methods of cDNA library construction. In addition, commercially available cDNA libraries or genomic libraries may also be used.

More specifically, in constructing a cDNA library, total RNA is first prepared from cells, organs, tissues, or such that express Lrp4, by known techniques such as guanidine ultracentrifugation (Chirwin et al. (1979) Biochemistry 18: 5294-5299) or AGPC (Chomczynski and Sacchi (1987) Anal. Biochem. 162: 156-159), followed by purification of mRNA using an mRNA Purification Kit (Pharmacia), or such. A kit for direct mRNA preparation, such as the QuickPrep mRNA Purification Kit (Pharmacia), may also be used. Next, cDNAs are synthesized from the resulting mRNAs using reverse transcriptase. cDNA synthesis kits, such as the AMV Reverse Transcriptase First-strand cDNA Synthesis Kit (Seikagaku Corporation), are also commercially available. Other methods that use the 5'-RACE method to synthesize and amplify cDNA by PCR may also be used (Frohman et al. (1988) Proc. Natl. Acad. Sci. USA 85: 8998-9002; Belyaysky et al. (1989) Nucleic Acids Res. 17: 2919-32). In addition, in order to construct cDNA libraries containing a high percentage of full-length clones, known techniques such as the oligo-capping method (Maruyama and Sugano (1994) Gene 138: 171-4; Suzuki (1997) Gene 200: 149-56) can also be employed. The cDNA obtained in this manner can be then incorporated into a suitable vector.

Examples of stringent hybridization conditions suitable for use in the present invention include "2×SSC, 0.1% SDS, 50° C.", "2×SSC, 0.1% SDS, 42° C." and "1×SSC, 0.1% SDS, 37° C.". Examples of conditions of higher stringency include "2×SSC, 0.1% SDS, 65° C.", "0.5×SSC, 0.1% SDS, 42° C." and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for one hour or more, washing three times in 2×SSC/0.1% SDS at room temperature for 20 minutes each, washing three times in 1×SSC/0.1% SDS at 37° C. for 20 minutes each, and finally washing twice in 1×SSC/0.1% SDS at 50° C. for 20 minutes each. This can also be carried out using, for example, the Expresshyb Hybridization Solution (CLONTECH), by performing pre-hybridization at 55° C. for 30 minutes or more, adding a labeled probe and incubating at 37° C. to 55° C. for one hour or more, washing three times in 2×SSC/0.1% SDS at room temperature for 20 minutes each, and washing once at 37° C. for 20 minutes with 1×SSC/0.1% SDS. Herein, conditions of higher stringency can be achieved by increasing the temperature for pre-hybridization, hybridization, or the second wash. For example, pre-hybridization and hybridization temperatures of 60° C. can be raised to 68° C. for higher stringency. In addition to factors such as salt concentration of the buffer and temperature, those with ordinary skill in the art can also integrate other factors, such as probe concentration, probe length, and reaction time, to obtain Lrp4 isoforms and allelic variants, and corresponding genes derived from other organisms.

References such as Molecular Cloning, A Laboratory Manual 2nd ed. (Cold Spring Harbor Press (1989); Section 9.47-9.58), Current Protocols in Molecular Biology (John Wiley & Sons (1987-1997); Section 6.3-6.4), DNA Cloning 1: Core Techniques, A Practical Approach 2nd ed. (Oxford University (1995); Section 2.10 for conditions, in particular), can be referred to for detailed information on hybridization procedures. Examples of hybridizing polynucleotides include polynucleotides containing a nucleotide sequence that has at least 50% or more, preferably 70%, more preferably 80% and even more preferably 90% (for example, 95% or more, or 99%) identity with a nucleotide sequence comprising the nucleotides of SEQ ID NO: 1 or SEQ ID NO: 2. Such identities can be determined by the BLAST algorithm (Altschul (1990) Proc. Natl. Acad. Sci. USA 87: 2264-8; Karlin and Altschul (1993) Proc. Natl. Acad. Sci. USA 90: 5873-7) as described in the homology determination above. In addition to the above-described BLASTN program for nucleotide sequences, the BLASTX program for determining the identity of amino acid sequences (Altschul et al. (1990) J. Mol. Biol. 215: 403-10) and the like has been developed based on this algorithm and can be used (as described above, see http://www.ncbi.nlm.nih.gov. for a specific example of analysis methods).

Lrp4 isoforms or allelic variants, and other genes with an Lrp4-like structure or function, can be obtained from cDNA libraries and genomic libraries of animals such as humans, mice, rats, rabbits, hamsters, chickens, pigs, cows, goats, and sheep, by designing primers based on the nucleotide sequences of SEQ ID NOs: 1 and 2, using gene amplification technology (PCR) (Current Protocols in Molecular Biology, John Wiley & Sons (1987) Sections 6.1-6.4).

The polynucleotide sequences can be confirmed by using conventional sequence determination methods. For example, the dideoxynucleotide chain termination method (Sanger et al. (1977) Proc. Natl. Acad. Sci. USA 74: 5463) can be used. In addition, sequences can also be analyzed using a suitable DNA sequencer.

Moreover, marker polynucleotide probes of the present invention include the aforementioned (1) sequences complementary to the nucleotide sequence of SEQ ID NO: 1 or 2, (2) sequences complementary to nucleotide sequences that encode the amino acid sequence described in SEQ ID NO: 3 or 4, (3) sequences complementary to nucleotide sequences that encode a sequence lacking the transmembrane domain portion of the amino acid sequence described in SEQ ID NO: 3 or 4, and (4) polynucleotides comprising nucleotide sequences that contain at least 15 consecutive nucleotides in each of the nucleotide sequences that hybridize under stringent conditions with a polynucleotide comprised of the nucleotide sequence of SEQ ID NO: 1 or 2. Such polynucleotides comprising a nucleotide sequence that contains at least 15 consecutive nucleotides can be used as a probe for detecting, or as a primer for amplifying, the expression of Lrp4 mRNA. The nucleotide chain normally consists of 15 to 100, and is preferably 15 to 35 nucleotides when used as a probe, or at least 15 and preferably 30 nucleotides when used as a primer. A primer can be designed to have a restriction enzyme recognition sequence, a tag or such, added to the 5'-end side thereof, and at the 3' end, a sequence complementary to a target sequence. Such polynucleotides, comprising a nucleotide sequence that contains at lease 15 consecutive nucleotides, can hybridize with an Lrp4 polynucleotide.

Furthermore, the marker polynucleotide probes of the present invention comprise a second polynucleotide which hybridizes under stringent conditions with a first polynucleotide comprising any one of: (1) the nucleotide sequence of SEQ ID NO: 1 or 2; (2) nucleotide sequences comprising polynucleotides encoding polypeptides comprising the amino acid sequence of SEQ ID NO: 3 or 4; (3) nucleotide sequences comprising polynucleotides encoding polypeptides comprising an amino acid sequence which lacks the transmembrane region in the amino acid sequence of SEQ ID NO: 3 or 4; and (4) nucleotide sequences comprising polynucleotides which hybridize under stringent conditions with a polynucleotide comprising the nucleotide sequence of SEQ ID NO: 1 or 2. Polynucleotides consisting of a nucleotide sequence comprising at least 15 consecutive nucleotides are preferred as the second polynucleotide.

Marker polynucleotide probes of the present invention can be prepared from cells that express Lrp4 by the aforementioned hybridization or PCR or such. In addition, marker polynucleotide probes of the present invention can also be produced by chemical synthesis based on known Lrp4 sequence data. Riboprobes, which are considered to be particularly preferable for detecting RNA in tissues, can be obtained by, for example, inserting a cloned Lrp4 gene or portion thereof into plasmid vector pSP64 in the reverse direction, followed by run-off transcription of the inserted sequence portion. Although pSP64 contains an SP6 promoter, methods for producing riboprobes by combining phage T3, T7 promoter and RNA polymerase are also known. The marker polynucleotide probes of the present invention may be used as reagents for discriminating the dopaminergic neuron proliferative progenitor cells. In the above-described reagents, the polynucleotides as active ingredients may be mixed as necessary with, for example, sterile water, saline, vegetable oils, surfactants, lipids, solubilizers, buffers, stabilizers, and preservatives.

<Antibodies>

The present invention provides dopaminergic neuron progenitor cell marker antibodies (hereinbelow, sometimes referred to as "antibodies of the present invention") which can be used to select dopaminergic neuron progenitor cells from brain tissue or cultured cells. Unlike Lrp4 mRNA, the Lrp4 polypeptide is expressed not only in the dopaminergic neuron proliferative progenitor cells prior to cell cycle exit, but also in postmitotic dopaminergic neuron precursor cells. Therefore, by using the antibodies of the present invention against the polypeptide, it is possible to select and/or obtain dopaminergic neuron progenitor cells prior to and after cell cycle exit. Antibodies of the present invention include polyclonal antibodies, monoclonal antibodies, chimeric antibodies, single-chain antibodies (scFV) (Huston et al. (1988) Proc. Natl. Acad. Sci. USA 85: 5879-83; The Pharmacology of Monoclonal Antibody, vol. 113, Rosenburg and Moore ed., Springer Verlag (1994) pp. 269-315), humanized antibodies, multispecific antibodies (LeDoussal et al. (1992) Int. J. Cancer Suppl. 7: 58-62; Paulus (1985) Behring Inst. Mitt. 78: 118-32; Millstein and Cuello (1983) Nature 305: 537-9; Zimmermann (1986) Rev. Physiol. Biochem. Pharmacol. 105: 176-260; Van Dijk et al. (1989) Int. J. Cancer 43: 944-9), and antibody fragments such as Fab, Fab', F(ab')2, and Fv. Moreover, antibodies of the present invention may also be modified by PEG and such, as necessary. Antibodies of the present invention may also be produced in the form of a fusion protein with β-galactosidase, maltose-binding protein, GST, green fluorescent protein (GFP) and such, to allow detection without the use of a secondary antibody. In addition, antibodies of the present invention may be modified by labeling with biotin or such, to allow recovery using avidin, streptoavidin, or such.

The antibodies of present invention are specific to any of (1) polypeptides encoded by the nucleotide sequence of SEQ ID NO: 1 or 2, (2) polypeptides comprised of the amino acid sequence described in SEQ ID NO: 3 or 4, (3) polypeptides comprised of an amino acid sequence lacking the transmembrane domain in the amino acid sequence described in SEQ ID NO: 3 or 4, (4) polypeptides comprised of an amino acid sequence wherein one or more amino acids in the amino acid sequence of SEQ ID NO: 3 or 4 are deleted, inserted, substituted, or added, (5) polypeptides encoded by a nucleotide sequence that hybridizes under stringent conditions with a sequence complementary to the nucleotide sequence of SEQ ID NO: 1 or 2, and (6) polypeptides that are fragments of the polypeptides of (1) to (5) above, with at least eight amino acid residues.

Also, the antibodies of the present invention may be antibodies that bind to polypeptides comprising any one of the following amino acid sequences (1) to (4) or parts thereof: (1) the amino acid sequence of SEQ ID NO: 3 or 4; (2) amino acid sequences which lack the transmembrane region in the amino acid sequence of SEQ ID NO: 3 or 4; (3) amino acid sequences mutated by one or more amino acid deletions, substitutions, or additions, or combinations thereof, in the amino acid sequence of SEQ ID NO: 3 or 4; and (4) amino acid sequences comprising polypeptides encoded by polynucleotides which hybridize under stringent conditions with polynucleotides comprising a nucleotide sequence complementary to the nucleotide sequence of SEQ ID NO: 1 or 2. The above-described polypeptides consisting of partial sequences include polypeptides comprising preferably at least six consecutive amino acid residues (e.g., 8, 10, 12, or 15 amino acid residues or more).

The amino acid sequences mutated by one or more amino acid deletions, substitutions, or additions, or combinations thereof in the amino acid sequence of SEQ ID NO: 3 include, for example: (i) amino acid sequences with 1 to 9 (e.g., 1 to 5, preferably 1 to 3, more preferably 1 to 2, and still more preferably 1) amino acid deletions in the amino acid sequence of SEQ ID NO: 3; (ii) amino acid sequences with 1 to 9 (e.g., 1 to 5, preferably 1 to 3, more preferably 1 to 2, and still more preferably 1) amino acid additions in the amino acid sequence of SEQ ID NO: 3; (iii) amino acid sequences with 1 to 9 (e.g., 1 to 5, preferably 1 to 3, more preferably 1 to 2, and still more preferably 1) amino acids substituted by other amino acids in the amino acid sequence of SEQ ID NO: 3; and (iv) an amino acid sequence mutated by any combination of the above (i) to (iii).

The amino acid sequences mutated by one or more amino acid deletions, substitutions, or additions, or any combinations thereof in the amino acid sequence of SEQ ID NO: 4 include, for example: (i) amino acid sequences with 1 to 9 (e.g., 1 to 5, preferably 1 to 3, more preferably 1 to 2, and still more preferably 1) amino acid deletions in the amino acid sequence of SEQ ID NO: 4; (ii) amino acid sequences with 1 to 9 (e.g., 1 to 5, preferably 1 to 3, more preferably 1 to 2, and still more preferably 1) amino acid additions in the amino acid sequence of SEQ ID NO: 4; (iii) amino acid sequences with 1 to 9 (e.g., 1 to 5, preferably 1 to 3, more preferably 1 to 2, and still more preferably 1) amino acids substituted by other amino acids in the amino acid sequence of SEQ ID NO: 4; and (iv) amino acid sequences mutated by any combination of the above (i) to (iii).

The term "amino acid deletions" herein means variants in which one or more amino acid residues in the sequence are deleted. The term "deletion" includes the deletion of an amino acid at either end of an amino acid sequence and the deletion of an amino acid in an amino acid sequence.

The term "amino acid additions" herein means variants in which one or more amino acid residues have been added to the sequence. The term "addition" includes the addition of an amino acid to either end of an amino acid sequence and the addition of an amino acid in an amino acid sequence.

The term "amino acid substitutions" herein means variants in which one or more amino acid residues in the sequence are substituted with different amino acid residues. When amino acid sequences are modified by such substitution, conservative substitution is preferably carried out. The term "conservative substitution" means changing the sequence to encode an amino acid with similar properties to the amino acid prior to substitution. Amino acids can be classified according to their properties into, for example: non-polar amino acids (Ala, Ile, Leu, Met, Phe, Pro, Trp, and Val); non-charged amino acids (Asn, Cys, Gln, Gly, Ser, Thr, and Tyr); acidic amino acids (Asp and Glu); basic amino acids (Arg, His, and Lys); neutral amino acids (Ala, Asn, Cys, Gln, Gly, Ile, Leu, Met, Phe, Pro, Ser, Thr, Trp, Tyr, and Val); aliphatic amino acids (Ala and Gly); branched amino acids (Ile, Leu, and Val), hydroxyamino acids (Ser and Thr); amide-type amino acids (Gln and Asn); sulfur-containing amino acids (Cys and Met); aromatic amino acids (His, Phe, Trp, and Tyr); heterocyclic amino acids (His and Trp); and imino acids (Pro and 4Hyp).

Therefore, it is preferable that non-polar amino acids are substituted with each other, or that non-charged amino acids are substituted with each other. Of these, substitutions among Ala, Val, Leu, and Ile, between Ser and Thr, between Asp and Glu, between Asn and Gln, between Lys and Arg, and between Phe and Tyr are preferable for retaining properties of the proteins. The number and sites of mutated amino acids are not particularly limited.

As the antibodies of the present invention, the two anti-Lrp4 antibodies used in Example 4, and modifications comprising fragments thereof, are particularly preferable. The two antibodies have been internationally deposited under the following accession numbers:
(1) Name and address of the depositary institution
Name: International Patent Organism Depositary, National Institute of Advanced Industrial Science and Technology
Address: Central 6, 1-1-1 Higashi, Tsukuba-shi, Ibaraki Prefecture, Japan 305-8566
(2) Deposit date: Jul. 14, 2004
(3) Accession Nos: FERM BP-10315 and FERM BP-10316 (transferred from FERM P-20120 and FERM P-20121 domestically deposited in Japan)

Antibodies of the present invention can be produced using a sensitizing antigen such as an Lrp4 polypeptide, or fragments thereof, or cells that express Lrp4 polypeptide or Lrp4 polypeptide fragments. In addition, short Lrp4 polypeptide fragments may also be used as immunogens by coupling with a carrier such as bovine serum albumin, Keyhole-limpet hemocyanin, and ovalbumin. In addition, the Lrp4 polypeptide, or fragments thereof, may be used in combination with known adjuvants, such as aluminum adjuvant, Freund's complete (or incomplete) adjuvant, or pertussis adjuvant, to enhance immune response to the antigen.

The "Lrp4 polypeptide" in the present invention is a peptide polymer, a preferred example of which is a protein having the amino acid sequence described in SEQ ID NO: 3 or 4. The amino acid residues that compose an Lrp4 polypeptide may be naturally occurring or modified. Moreover, the Lrp4 polypeptides include proteins lacking a transmembrane domain portion, and fusion proteins modified by other peptide sequences.

In the present invention, the Lrp4 polypeptides should have the antigenicity of the Lrp4 polypeptide, and include polypeptides with an amino acid sequence wherein one or more amino acids in the amino acid sequence of SEQ ID NO: 3 or 4 are deleted, inserted, substituted, or added. It is well known that mutant polypeptides comprising an amino acid sequence in which one or more amino acids are deleted, inserted, substituted, or added, maintain the same biological activity as the original polypeptide (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; Dalbadie-McFarland et al. (1982) Proc. Natl. Acad. Sci. USA 79: 6409-13). Such polypeptides that maintain the antigenicity of Lrp4 and have an amino acid sequence in which one or more amino acids are deleted, inserted, substituted, or added to the amino acid sequence of SEQ ID NO: 3 or 4, can be obtained by preparing polynucleotides that encode the polypeptides using known methods such as site-directed mutagenesis described in "Molecular Cloning, A Laboratory Manual 2nd ed." (Cold Spring Harbor Press (1989)), "Current Protocols in Molecular Biology" (John Wiley & Sons (1987-1997); especially section 8.1-8.5), Hashimoto-Goto et al. (1995) Gene 152: 271-5, Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6), and others, and then suitably expressing. In addition to the above-described site-directed mutagenesis, methods for subjecting genes to mutagens can be used. Alternatively, methods for selectively cleaving genes; removing, adding, or substituting selected nucleotides; and then ligating the genes can also be used.

Lrp4 polypeptide fragments are identical to a portion of the aforementioned Lrp4 polypeptide, and preferably consists of at least six continuous amino acid residues or more (for example, 8, 10, 12, or 15 amino acid residues or more). A particularly preferred fragment can be exemplified by a polypeptide fragment lacking an amino terminus, carboxyl terminus, and transmembrane domain. The Lrp4 polypeptide fragments include fragments containing an α-helix and α-helix forming region, α-amphipathic region, β-sheet and β-sheet forming region, β-amphipathic region, substrate binding region, high antigen index region, coil and coil forming region, hydrophilic region, hydrophobic region, turn and turn forming region, and surface forming region. In the context of the present invention, an Lrp4 polypeptide fragment may be any fragment, so long as it has the antigenicity of an Lrp4 polypeptide. The antigen-determining site of a polypeptide can be predicted by using methods for analyzing the hydrophobicity/hydrophilicity of an amino acid sequence of a protein (Kyte-Doolittle (1982) J. Mol. Biol. 157: 105-22), or methods of secondary structure analysis (Chou-Fasman (1978) Ann. Rev. Biochem. 47: 251-76), and can be confirmed using computer programs (Anal. Biochem. 151: 540-6 (1985)), or the PEPSCAN method in which a short peptide is synthesized followed by confirmation of its antigenicity (Published Japanese Translation of International Publication No. Sho 60-500684), or the like.

Lrp4 polypeptides and Lrp4 polypeptide fragments can be isolated from Lrp4-expressing cells, tissues, etc., based on their physical properties and such. In addition, these polypeptides and polypeptide fragments can also be produced using known genetic recombination techniques or chemical synthesis methods. For example, for in vitro Lrp4 polypeptide production, Lrp4 polypeptides can be produced in an in vitro cell-free system using methods such as in vitro translation (Dasso and Jackson (1989) Nucleic Acids Res. 17: 3129-44). In contrast, when producing polypeptides using cells, a polynucleotide that encodes a polypeptide of interest is first incorporated into an appropriate vector, a suitable host cell is selected, and then the cells are transformed by the vector. Subsequently, the transformed cells can be cultured to obtain the polypeptide of interest.

Appropriate vectors include various vectors such as plasmids, cosmids, viruses, bacteriophages, cloning vectors, and expression vectors (Molecular Cloning, A Laboratory Manual $2^{nd}$ ed., Cold Spring Harbor Press (1989); Current Protocols in Molecular Biology, John Wiley & Sons (1987)). The vectors comprise regulatory sequences for the expression of a desired polynucleotide in transfected host cells, and the polynucleotide is incorporated therein so that it will be under the control of the regulatory sequences. Here, the phrase "regulatory sequence" includes promoters, ribosome binding sites, and terminators in the case of a prokaryotic host cell, and promoters and terminators in the case of a eukaryotic host cell, and in some cases, may also contain transactivators, transcription factors, poly A signals which stabilize transcription products, splicing and polyadenylation signals, and others. Such regulatory sequences comprise all the components required for the expression of a polynucleotide linked thereto. Vectors may further comprise a selection marker. Moreover, a signal peptide required for transferring an intracellularlly expressed polypeptide into the lumen of the endoplasmic reticulum, or the periplasm or extracellular space when the host is a Gram negative microbe, can also be incorporated into an expression vector by linking to a polypeptide of interest. Such signal peptides can be signal peptides derived from heterogeneous proteins. Moreover, a linker may be added, and a start (ATG) or stop codon (TAA, TAG, or TGA) may be inserted as necessary.

Examples of vectors capable of expressing polypeptides in vitro include pBEST (Promega). In addition, various vectors are known to be suitable for expression in prokaryotic hosts (see, e.g., "Basic Microbiology Course 8—Genetic Engineering" (Kyoritsu Publishing)). When selecting prokaryotic cells as the host, a person with ordinary skill in the art can suitably select a vector suitable for the host and a method suitable for introducing the vector into the host. Other examples of hosts that can be used to express Lrp4 polypeptides and their antigenic fragments include fungal cells such as yeasts, higher plants, insects, fish, amphibians, reptiles, birds, mammals, cultured cells (COS, Hela, C127, 3T3, BHK, HEK293, Bowes melanoma cells), myeloma, Vero, Namalwa, Namalwa KJM-1, and HBT5637 (Unexamined Published Japanese Patent Application No. Sho 63-299). Vector systems suitable for each cell and methods for introducing a vector into host cells are also known. Moreover, methods for expressing exogenous proteins in animals in vivo (see, e.g., Susumu (1985) Nature 315: 592-4; Lubon (1998) Biotechnol. Annu. Rev. 4: 1-54) and in plant bodies are also known, and can be used to express Lrp4 polynucleotides.

DNAs can be inserted into vectors in a ligase reaction using restriction enzyme sites (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63). In addition, an Lrp4 polypeptide-encoding expression vector can be designed as necessary by selecting a nucleotide sequence that has high expression efficiency in view of the host's codon usage frequency (Grantham et al. (1981) Nucleic Acids Res. 9: r43-74). A host that produces an Lrp4 polypeptide comprises in its cells a polynucleotide that encodes an Lrp4 polypeptide. So long as the polynucleotide does not exist at a naturally occurring position in the genome of a host cell, the polynucleotide itself may be regulated by its own promoter, incorporated in the host genome, or maintained as an extrachromosomal structure.

Transduction (transformation/transfection) of host cells with vectors can be performed using well-known methods.

Transformation can be performed, for example, by the method by Cohen et al. (Proc. Natl. Acad. Sci. USA 69, 2110 (1972)), protoplast methods (Mol. Gen. Genet., 168, 111 (1979)), and the competent method (J. Mol. Biol., 56, 209 (1971)) for bacteria (*E. coli, Bacillus subtilis*, etc.); by the method by Hinnen et al. (Proc. Natl. Acad. Sci. USA 75, 1927 (1978)) and lithium methods (J. Bacteriol., 153, 163 (1983)) for *Saccharomyces cerevisiae*; by leaf disk methods (Science, 227, 129 (1985)), electroporation methods (Nature, 319, 791 (1986)), and *Agrobacterium* methods (Horsch et al., Science, 227, 129 (1985); and Hiei et al., Plant J., 6, 271-282 (1994)) for plant cells; by the method by Graham (Virology, 52, 456 (1973)) for animal cells; and by the method by Summers et al. (Mol. Cell Biol., 3, 2156-2165 (1983)) for insect cells.

Culturing of host cells is carried out using known methods that are appropriate for the host cell selected. For example, when animal cells are selected, culturing can be carried out at a pH of about 6 to 8 and a temperature of 30° C. to 40° C. for about 15 to 200 hours, using a medium such as DMEM (Virology 8: 396 (1959)), MEM (Science 122: 501 (1952)), RPMI1640 (J. Am. Med. Assoc. 199: 519 (1967)), 199 (Proc. Soc. Biol. Med. 73: 1 (1950)), or IMDM, and adding serum such as fetal calf serum (FCS), as necessary. In addition, the medium may be replaced, aerated, or stirred during the course of culturing, as necessary.

Normally, an Lrp4 polypeptide produced by gene recombination techniques can be recovered from the medium if the polypeptide is secreted outside of a cell, or from the body fluid of a transgenic organism. When a polypeptide is produced inside of a cell, the cells can be dissolved and the polypeptide is recovered from the dissolved product. The polypeptide of interest can be then purified by suitably combining known methods of protein purification, such as salting out, distillation, various types of chromatography, gel electrophoresis, gel filtration, ultrafiltration, recrystallization, acid extraction, dialysis, immunoprecipitation, solvent precipitation, solvent extraction, and ammonium sulfate or ethanol precipitation. Examples of chromatographies include ion exchange chromatography, such as anion or cation exchange chromatography, affinity chromatography, reversed-phase chromatography, adsorption chromatography, gel filtration chromatography, hydrophobic chromatography, hydroxyapatite chromatography, phosphocellulose chromatography, and lectin chromatography (Strategies for Protein Purification and Characterization: A Laboratory Course Manual, Marshak et al. ed., Cold Spring Harbor Laboratory Press (1996)). Chromatography can be carried out using a liquid phase chromatography, such as HPLC or FPLC. In addition, for example, a protein fused with GST can be purified using a glutathione column, and a protein with a histidine tag can be purified using a nickel column. When an Lrp4 polypeptide is produced as a fusion protein, unnecessary portions can be removed using thrombin, factor Xa, or the like, following purification as necessary.

In addition, naturally-occurring polypeptides can also be purified and obtained. For example, polypeptides can be purified by affinity chromatography using antibodies against the Lrp4 polypeptides (Current Protocols in Molecular Biology, John Wiley & Sons (1987) Section 16.1-16.19). Moreover, purified polypeptides can also be modified using enzymes, such as chymotrypsin, glucosidase, trypsin, protein kinase, and lysyl endopeptidase, as necessary. In addition to the aforementioned synthesis and genetic engineering techniques as used for Lrp4 polypeptides, Lrp4 polypeptide fragments can also be produced by cleaving an Lrp4 polypeptide, using suitable enzymes, such as peptidases.

Polyclonal antibodies for selecting dopaminergic neuron progenitor cells can be obtained from, for example, the serum of an immunized animal after immunizing a mammal with an Lrp4 polypeptide purified as described above, or a fragment thereof, coupled to a desired adjuvant. Although there are no particular limitations on the mammals used, typical examples include rodents, lagomorphs, and primates. Specific examples include rodents such as mice, rats, and hamsters, lagomorphs such as rabbits, and primates such as monkeys, including cynomolgus monkeys, rhesus monkeys, baboons, and chimpanzees. Animal immunization is carried out by suitably diluting and suspending a sensitizing antigen in phosphate-buffered saline (PBS) or physiological saline, mixing with an adjuvant as necessary until emulsified, and injecting into an animal intraperitoneally or subcutaneously. The sensitizing antigen mixed with Freund's incomplete adjuvant is preferably administered several times, every 4 to 21 days. Antibody production can be confirmed by measuring the level of an antibody of interest in the serum using conventional methods. Finally, the serum itself may be used as a polyclonal antibody, or it may be further purified. See, for example, "Current Protocols in Molecular Biology" (John Wiley & Sons (1987) Sections 11.12-11.13), for specific methods.

A monoclonal antibody can be produced by removing the spleen from an animal immunized in the manner described above, separating immunocytes from the spleen, and fusing with a suitable myeloma cell using polyethylene glycol (PEG) or such to establish hybridomas. Cell fusion can be carried out according to the Milstein method (Galfre and Milstein (1981) Methods Enzymol. 73: 3-46). Here, suitable myeloma cells are exemplified particularly by cells that allow chemical selection of fused cells. When using such myeloma cells, fused hybridomas can be selected by culturing in a culture medium (HAT culture medium) that contains hypoxanthine, aminopterin, and thymidine, which destroys cells other than fused cells. Next, clones that produce antibodies against polypeptides of the present invention, or a fragment thereof, can be selected from the established hybridomas. Subsequently, the selected clone is introduced into the abdominal cavity of a mouse or such, and ascites can be collected to obtain a monoclonal antibody. See also "Current Protocols in Molecular Biology" (John Wiley & Sons (1987) Section 11.4-11.11), for information on specific methods. Preferable hybridomas of the present invention can be FERM BP-10315 and FERM BP-10316.

Hybridomas can also be obtained by first sensitizing human lymphocytes that have been infected by EB virus with an immunogen in vitro, and fusing the sensitized lymphocytes with human myeloma cells (such as U266) to obtain hybridomas that produce human antibodies (Unexamined Published Japanese Patent Application No. Sho 63-17688). In addition, human antibodies can also be obtained by using antibody-producing cells generated by sensitizing a transgenic animal with a human antibody gene repertoire (WO92/03918; WO93-02227; WO94/02602; WO94/25585; WO96/33735; WO96/34096; Mendez et al. (1997) Nat. Genet. 15: 146-156, etc.). Methods that do not use hybridomas can be exemplified by a method in which a cancer gene is introduced to immortalize immunocytes such as antibody-producing lymphocytes.

In addition, antibodies of the present invention can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is then cultured to produce the antibody. This type of recombinant antibody is also included in the antibodies of the present invention. Typical examples of recombinant antibodies include chimeric antibodies, comprising a non-human antibody-derived variable region and a human antibody-derived constant region, and humanized antibodies, comprising a non-human-derived antibody complementarity determining region (CDR), human antibody-derived framework region (FR), and human antibody constant region (Jones et al. (1986) Nature 321: 522-5; Reichmann et al. (1988) Nature 332: 323-9; Presta (1992) Curr. Op. Struct. Biol. 2: 593-6; Methods Enzymol. 203: 99-121 (1991)).

Antibody fragments can be produced by treating the aforementioned polyclonal or monoclonal antibodies with enzymes such as papain or pepsin. Alternatively, antibody fragments can be produced by genetic engineering techniques using genes that encode antibody fragments (see Co et al., (1994) J. Immunol. 152: 2968-76; Better and Horwitz (1989) Methods Enzymol. 178: 476-96; Pluckthun and Skerra (1989) Methods Enzymol. 178: 497-515; Lamoyi (1986) Methods Enzymol. 121: 652-63; Rousseaux et al. (1986) 121: 663-9; Bird and Walker (1991) Trends Biotechnol. 9: 132-7).

Multispecific antibodies include bispecific antibodies (BsAb), diabodies (Db), and such. Multispecific antibodies can be produced by methods such as (1) chemically coupling antibodies having different specificities with different types of bifunctional linkers (Paulus (1985) Behring Inst. Mill. 78: 118-32), (2) fusing hybridomas that secrete different monoclonal antibodies (Millstein and Cuello (1983) Nature 305: 537-9), or (3) transfecting eukaryotic cell expression systems, such as mouse myeloma cells, with a light chain gene and a heavy chain gene of different monoclonal antibodies (four types of DNA), followed by the isolation of a bispecific monovalent portion (Zimmermann (1986) Rev. Physio. Biochem. Pharmacol. 105: 176-260; Van Dijk et al. (1989) Int. J. Cancer 43: 944-9). Alternatively, diabodies are dimer antibody fragments comprising two bivalent polypeptide chains that can be constructed by gene fusion. These can be produced using known methods (see Holliger et al. (1993) Proc. Natl. Acad. Sci. USA 90: 6444-8; EP404097; WO93/11161).

Recovery and purification of antibodies and antibody fragments can be carried out using Protein A and Protein G, or according to the protein purification techniques described above in producing non-antibody polypeptides (Antibodies: A Laboratory Manual, Ed Harlow and David Lane, Cold Spring Harbor Laboratory (1988)). For example, when using Protein A to purify antibodies of the present invention, Protein A columns such as Hyper D, POROS, or Sepharose F.F. (Pharmacia), can be used. The concentration of the resulting antibodies can be determined by measuring absorbance or by enzyme linked immunosorbent assay (ELISA).

The antigen binding activity of an antibody can be determined using absorbance measurements, or by using fluorescent antibody methods, enzyme immunoassay (EIA) methods, radioimmunoassay (RIA) methods, or ELISA. When ELISA is used, for example, antibodies of the present invention are first immobilized onto a support, such as a plate. An Lrp4 polypeptide is added, and then a sample containing the antibody of interest is added. Herein, samples containing an antibody of interest include, for example, culture supernatants of antibody-producing cells, purified antibodies, and such. Next, secondary antibodies that recognize the antibodies of the present invention are added, and the plate is incubated. The plate is then washed and a label attached to the secondary antibody is detected. Namely, if a secondary antibody is labeled with alkaline phosphatase, antigen binding activity can be determined by adding an enzyme substrate such as p-nitrophenyl phosphate, and measuring absorbance. In addition, a commercially available system such as BIAcore (Pharmacia) can also be used to evaluate antibody activities.

The present invention relates to reagents which comprise the anti-Lrp4 antibody as an active ingredient for identifying dopaminergic neuron progenitor cells. In the above-described reagents, the antibodies of the present invention as active ingredients may be mixed as necessary with, for example, sterile water, saline, vegetable oils, surfactants, lipids, solubilizer, buffers, protein stabilizers (such as BSA and gelatin), and preservatives.

<Methods for Selecting Dopaminergic Neuron Progenitor Cells and Such>

The present invention provides methods for selecting dopaminergic neuron proliferative progenitor cells as a selectively uniform population. The dopaminergic neuron proliferative progenitor cells can be selected by using the marker polynucleotide probes of the present invention. The present invention also provides methods for selecting the dopaminergic neuron progenitor cells as a selectively uniform population. The dopaminergic neuron progenitor cells can suitably be selected using the antibodies of the present invention. As described above, by using the polynucleotide probes or antibodies of the present invention, the dopaminergic neuron lineage cells which eventually differentiate into dopaminergic neurons can be specifically selected.

Here, the term "selected" includes both detecting the presence of cells expressing markers in a sample, and subsequently separating or isolating those progenitor cells after detecting their presence. The present invention provides methods for selecting dopaminergic neuron proliferative progenitor cells, comprising a step of contacting marker polynucleotide probes of the present invention with cell samples containing dopaminergic neuron proliferative progenitor cells. In this method, marker polynucleotide probes are preferably labeled with a radioactive isotope or non-radioactive compound. Examples of the radioactive isotopes used for labeling include $^{35}$S and $^{3}$H. When using a radiolabeled marker polynucleotide probe, RNA that binds with the marker can be detected by detecting silver particles using emulsion autoradiography. Examples of non-radioactive isotopes for labeling a marker polynucleotide probe include biotin and digoxigenin. A biotin-labeled marker can be detected using, for example, avidin labeled with fluorescence or an enzyme such as alkaline phosphatase or horseradish peroxidase. On the other hand, anti-digoxigenin antibodies labeled with fluorescence or an enzyme, such as alkaline phosphatase or horseradish peroxidase, can be used to detect a digoxigenin-labeled marker. When using enzyme labeling, detection can be carried out by incubating with the enzyme substrate to form a stable pigment at the location of the marker. Fluorescent in situ hybridization (FISH) is convenient and particularly preferable.

In addition, the present invention provides methods for selecting dopaminergic neuron progenitor cells comprising the step of contacting antibodies for selecting the dopaminergic neuron progenitor cells of the present invention with cell samples containing dopaminergic neuron progenitor cells. Namely, dopaminergic neuron progenitor cells can be acquired by contacting cell samples containing potential dopaminergic neuron progenitor cells with antibodies of the present invention, and selecting those cells that have bound to the antibody (see FIG. 13). The antibodies of the present invention may also be immobilized on a suitable support, prior to contact with cell samples. Alternatively, cells that bind with the antibodies can be selectively recovered by contacting cell samples with the antibodies of the present invention, allowing them to bind, and then purifying the antibody by affinity chromatography. For example, if the antibodies of the present invention are conjugated to biotin, they can be purified on a plate or column bound with avidin or streptoavidin. In addition, magnetic particles can be bound to an antibody, for example, and the antibody and cells that express Lrp4 on their surfaces, where the Lrp4 is bound to the antibody, can be recovered using a magnet. Dopaminergic neuron progenitor cells that express Lrp4 can be selected by flow cytometry using a cell sorter and fluorescent-labeled anti-Lrp4 antibodies and such.

The dopaminergic neuron progenitor cell populations obtained as described above are cell populations comprising, for example, 40% or more, preferably 50% or more, more preferably 60% or more, and particularly preferably 70% or more dopaminergic neuron progenitor cells.

The present invention provides methods for selecting and/or producing postmitotic dopaminergic neuron precursor cells, which comprise the step of culturing the dopaminergic neuron progenitor cells selected by using the marker polynucleotide probes or antibodies of the present invention. The present invention also provides methods for selecting and/or producing postmitotic dopaminergic neuron precursorcells, which comprise the steps of contacting cell samples comprising the dopaminergic neuron progenitor cells with the marker polynucleotide probes or antibodies of the present invention; selecting the dopaminergic neuron progenitor cells; and culturing the selected cells.

Furthermore, according to the present invention, the postmitotic dopaminergic neuron precursor cells, which have a low risk of tumorigenesis and are suitable for transplant therapy, can be obtained by culturing the dopaminergic neuron progenitor cells selected by using the marker polynucleotide probes or antibodies of the present invention; and selecting and/or screening by using the postmitotic dopaminergic neuron precursorcell markers. The postmitotic dopaminergic neuron precursor cell markers can include, for example, 65B13, Nurr1, and TH (WO 2004/038018; Kawasaki et al., Neuron 28:31-40 (2000); Wallen et al., Exp. Cell Res., 253:737-46 (1999)). For example, the postmitotic dopaminergic neuron precursor cells can be selected and/or produced by contacting cell samples comprising dopaminergic neuron progenitor cells with the marker polynucleotide probes or antibodies of the present invention; selecting the dopaminergic neuron progenitor cells; and contacting the antibody against 65B13 polypeptide with the dopaminergic neuron progenitor cells further cultured as necessary to select the cells expressing the 65B13 polypeptide.

The present invention provides methods for selecting and/or producing dopaminergic neurons, where the methods comprise the step of culturing the dopaminergic neuron progenitor cells selected by using the marker polynucleotide probes or antibodies of the present invention. The present invention also provides methods for selecting and/or producing dopaminergic neurons which comprise the steps of contacting cell samples containing the dopaminergic neuron progenitor cells with the marker polynucleotide probes or antibodies of the present invention; selecting the dopaminergic neuron progenitor cells; and culturing the selected cells.

According to the present invention, dopaminergic neurons, which have a low risk of tumorigenesis and are suited to transplant therapy, can also be obtained by culturing the dopaminergic neuron progenitor cells selected by using the marker polynucleotide probes or antibodies of the present invention; and selecting and/or screening by using the dopaminergic neuron markers. The dopaminergic neuron markers can include, for example, DAT (Development 131 (5): 1145-55 (2004)). For example, the dopaminergic neurons can be selected and/or produced by contacting cell samples containing the dopaminergic neuron progenitor cells with the marker polynucleotide probes or antibodies of the present invention; selecting the dopaminergic neuron progenitor cells; and contacting an antibody against DAT with the further cultured dopaminergic neuron progenitor cells to select cells expressing DAT.

The present invention provides methods for selecting and/or producing dopaminergic neuron proliferative progenitor cells capable of proliferating when cultivated, where the methods comprise the steps of culturing or not culturing the dopaminergic neuron progenitor cells selected by using the antibodies of the present invention; and removing the postmitotic dopaminergic neuronprecursor cells. The present invention also provides methods for selecting and/or producing the dopaminergic neuron proliferative progenitor cells capable of proliferating when cultivated, where the methods comprise the steps of contacting cell samples containing the dopaminergic neuron progenitor cells with the antibodies of the present invention; selecting the dopaminergic neuron progenitor cells; culturing or not culturing the selected cells; and then removing the postmitotic dopaminergic neuron precursor cells.

In the step of removing the postmitotic dopaminergic neuron precursor cells, dopaminergic neuron proliferative progenitor cells capable of proliferating when cultivated can also be obtained by selection and/or removal using markers for postmitotic dopaminergic neuron precursor cells. Markers for postmitotic dopaminergic neuron precursor cells can include, for example, 65B13, Nurr1, and TH (WO 2004/038018; Kawasaki et al., Neuron 28:31-40 (2000); Wallen et al., Exp. Cell Res., 253:737-46 (1999)). Dopaminergic neuron proliferative progenitor cells can be selected and/or produced by, for example, contacting the antibodies of the present invention with cell samples containing dopaminergic neuron progenitor cells, selecting the dopaminergic neuron progenitor cells, and contacting an antibody against the 65B13 polypeptide with the dopaminergic neuron progenitor cells further cultured as necessary to select cells which do not express the 65B13 polypeptide.

In addition, Lrp4-expressing dopaminergic neuron progenitor cells can also be selected and/or screened using promoters for Lrp4 (see, for example, Unexamined Published Japanese Patent Application No. 2002-51775). For example, a vector harboring a construct that comprises a gene encoding a detection marker, such as GFP, linked to a promoter region obtained from analyzing the Lrp4 expression regulatory regions to be described later, can be transfected into cells. In addition, a gene encoding a marker can also be knocked in at the Lrp4 gene locus. In either case, specific cells can be selected by detecting the expression of a marker gene specific to dopaminergic neuron progenitor cells.

The cell samples used herein preferably comprise cells of the ventral midbrain region or culture cells containing in vitro differentiated dopaminergic neuron progenitor cells. In vitro differentiation of dopaminergic neurons can be carried out by known methods using a starting material like cells such as known ES cells, bone marrow interstitial cells, immortalized neuron-derived cell lines (Published Japanese Translation of International Publication No. Hei 8-509215; Published Japanese Translation of International Publication No. Hei 11-506930; Published Japanese Translation of International Publication No. 2002-522070), or primordial neuron cells (Published Japanese Translation of International Publication No. Hei 11-509729). Normally, dopaminergic neurons can be differentiated by co-culturing a tissue obtained from a dopaminergic neuron region of the brain, with a sustentacular cell layer derived from neural tissues. Moreover, methods are also known for deriving dopaminergic neurons from neural tissues that do not normally produce dopamine, such as the striatum and cortex (Published Japanese Translation of International Publication No. Hei 10-509319). In addition, culturing under hypoxic conditions has been reported to produce cells containing a greater number of dopaminergic neurons (Published Japanese Translation of International Publication No. 2002-530068). ES cells (CCE) can also be induced to differentiate to dopaminergic neurons using the 5-stage method (Lee et al. (2000) Nat. Biotech. 18: 675-679, mouse dopaminergic neuron differentiation kit (R&D Systems)). Cell samples used in the selection of dopaminergic neuron progenitor cells of the present invention may be cell populations isolated or cultured by any method, including the above-described methods.

In addition, the supports used in immobilizing the antibodies of the present invention are preferably safe for cells. Examples of such supports include synthetic or naturally-occurring organic polymer compounds, inorganic materials such as glass beads, silica gel, alumina, and activated charcoal, and those with surfaces coated with a polysaccharide or synthetic polymer. There are no particular limitations on the form of the support, examples of which include films, fibers, granules, hollow fibers, non-woven fabrics, porous supports, or honeycombed supports. The contact surface area of the supports can be controlled by changing their thickness, surface area, width, length, shape, and size in various ways.

<Kits for Treating Neurodegenerative Diseases Comprising Dopaminergic Neuron Progenitor Cells, and Methods for Treating Neurodegenerative Diseases Using Dopaminergic Neuron Progenitor Cells>

Figure 13:
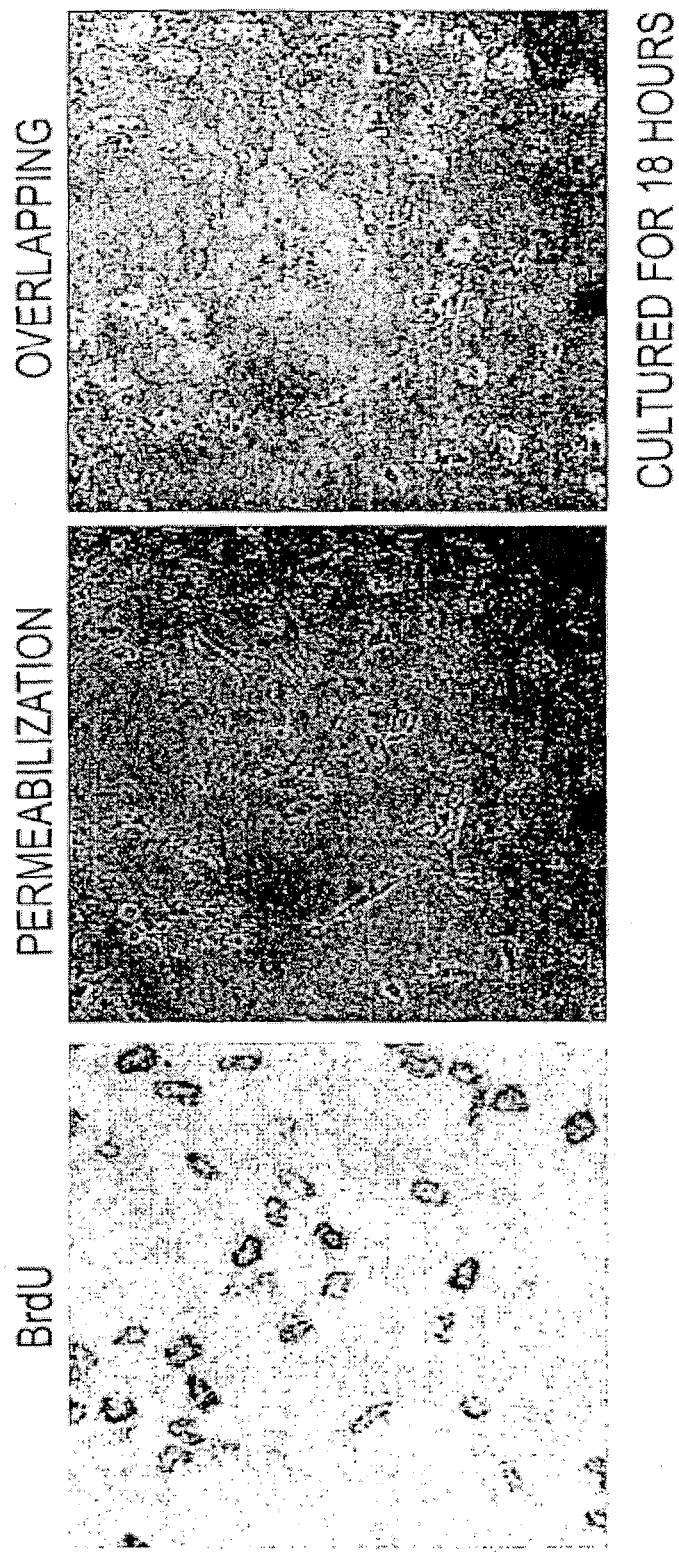
FIG. 13 is a set of photographs showing the in vitro proliferation of Lrp4-positive cells.

The cells acquired using polynucleotide probes and expression of Lrp4 mRNA as an index are dopaminergic neuron proliferative progenitor cells. Cells acquired using the antibodies and expression of Lrp4 polypeptides as an index are dopaminergic neuron progenitor cells. Thus, by using either the mRNAs or the polypeptides as indexes, dopaminergic neuron lineage cell populations can be obtained. The progenitor cells obtained by the methods of the present invention are more preferable for transplant therapy for diseases related to postural reflex, movement, and reward-associated behaviors, particularly neurodegenerative diseases such as Parkinson's disease, schizophrenia, and drug habits (Hynes et al., Cell 80: 95-101 (1995)) in terms of safety, survival rate, and network forming capacity compared to conventional unpurified cell populations or dopaminergic neurons into which exogenous genes are introduced. The cells acquired using Lrp4 expression as an index can be used for transplantation directly or after in vitro proliferation (FIG. 13). Such cells are expected to exert therapeutic effects because they are likely to differentiate and mature in an optimal place in the brain. Therefore, the present invention also provides kits (hereinafter, sometimes referred to as "kits of the present invention") for treating neurodegenerative diseases, where the kits comprises dopaminergic neuron proliferative progenitor cells, postmitoticc dopaminergic neuron precursor cells, and/or dopaminergic neurons selected and/or produced using the marker polynucleotide probes or antibodies of the present invention, as well as methods for treating neurodegenerative diseases which comprise the step of transplanting the cells into the brains of patients. Furthermore, the present invention also provides uses of dopaminergic neuron proliferative progenitor cells, postmitotic dopaminergic neuron precursorcells, and/or dopaminergic neurons selected and/or produced using the marker polynucleotide probes or antibodies of the present invention for producing the kits for treating neurodegenerative disease. In the present invention, the term "neurodegenerative diseases" preferably includes Parkinson's disease. The kits of the present invention may comprise pharmaceutically acceptable carriers in addition to the cells. The term "carriers" include, for example, salines, phosphate buffers, media, sera, body fluids, carboxymethyl cellulose solutions, scaffolding solids for supporting cells (e.g., cytodex3 (Amersham Bioscience, 17-0485-01)), extracellular matrix components (e.g., collagen, fibronectin, vitronectin, laminin, heparan sulfate, proteoglycan, glucosaminoglycan, chondroitin sulfate, hyaluronate, elastin, or combination of two or more thereof), or gel-like supports. A pH adjuster, buffer, stabilizer, preservative, and the like can be added to the kits of the present invention. The kits of the present invention may be for single or multiple inoculation. It is also possible to appropriately select dosage depending on the body weight and age of the humans or animals to be inoculated, the administration methods, and so on.

Since the dopaminergic neuron progenitor cells selected using Lrp4 expression as an index are likely to further proliferate in vivo, they are expected to exert therapeutic effects for an extended period. Furthermore, the dopaminergic neuron progenitor cells selected using the Lrp4 expression as an index can be differentiated in vitro to an appropriate stage by selecting conditions such as the medium, and are preferred as the materials for various neural transplant therapies. As described above, for example, the dopaminergic neuron progenitor cells selected using Lrp4 expression as an index can be subjected to further selection using markers (e.g., 65B13, Nurr1, TH, etc.) for postmitotic dopaminergic neuron precursor cells, to obtain even safer cells for use in transplantation. The present invention relates to methods for culturing the above-described progenitor cells in vitro for differentiation and proliferation. The dopaminergic neuron progenitor cells for culturing can be postmitotic precursor cells.

For example, $1\times10^2$ to $1\times10^8$ dopaminergic neuron progenitor cells obtained using the methods of the present invention can be transplanted, preferably $1\times10^3$ to $1\times10^6$ cells, and more preferably $5\times10^4$ to $6\times10^4$ cells. The primary method is stereotaxic surgery, in which a cell suspension is transplanted into the brain. In addition, cells may also be transplanted by microsurgery. For methods of transplanting neuron tissues see Backlund et al. (Backlund et al. (1985) J. Neurosurg. 62: 169-73), Lindvall et al. (Lindvall et al.

(1987) Ann. Neurol. 22: 457-68), or Madrazo et al. (Madrazo et al. (1987) New Engl. J. Med. 316: 831-4).

Moreover, the cells of the present invention can also be used to isolate genes specific to dopaminergic neuron proliferative progenitor cells, and genes specific to each stage of maturation from proliferative progenitor cells into dopaminergic neurons. They can also be used to search for therapeutic targets for Parkinson's disease, to elucidate the maturation process of dopaminergic neurons, and in screenings using maturation as an indicator.

<Comparison of Gene Expression Levels>

Dopaminergic neuron progenitor cells, obtained using the polynucleotide probes and antibodies of the present invention, can be used as materials to isolate genes specifically expressed in these cells. They can also be used to investigate and isolate genes specifically expressed in cells that have been differentiated, induced, or proliferated from the dopaminergic neuron progenitor cells of the present invention. In addition, they can also be used to investigate the genes required for in vivo differentiation of dopaminergic neurons, by investigating genes that have different expression levels in cells that have differentiated, induced, or proliferated and the original progenitor cells. Since such genes are potential candidates for treating diseases caused by defects in dopaminergic neurons, determining and isolating them is extremely useful.

Comparison of gene expression levels in the dopaminergic neuron progenitor cells of the present invention with those in cells that have been differentiated, induced, or proliferated therefrom, or other cells; or comparison of gene expression levels of the differentiated, induced, or proliferated cells with those of other cells, can be done using commonly used methods, such as cell in situ hybridization, Northern blot hybridization, RNA dot blot hybridization, reverse transcription PCR, RNase protection assay, DNA microarray hybridization, serial analysis of gene expression (SAGE) (Velculescu et al. (1995) Science 270: 484-487), subtractive hybridization, and representation difference analysis (RDA) (Lisitsyn (1995) Trends Genet. 11: 303-307).

For cellular in situ hybridization, places where RNA processing, transport, and localization into the cytoplasm occur in individual cells can be investigated, by hybridizing total RNA or poly A$^+$ RNA prepared from cells with a labeling probe specific to a given RNA sequence. In addition, RNA size can be determined from size fractioning using gel electrophoresis. Moreover, RNA transcription products can be visualized in situ by using quantitative fluorescent in situ hybridization (FISH) and a digital imaging microscope (Femino et al. (1998) Science 280: 585-90), which are applicable to the present invention.

When using reverse transcription PCR for gene expression analysis, the expression of specific genes can be roughly quantified. Various isoforms of a single RNA transcription product can also be detected and analyzed using the present methods. For reverse transcription PCR, when the reaction is carried out using exon-specific primers, and amplification products other than the predicted product are detected, mRNA isoforms produced by alternative splicing can be identified by analyzing these products. For more details see, for example, the method described in Pykett et al. (1994) Hum. Mol. Genet. 3: 559-64. When a quick and rough analysis of expression pattern is required, the methods which use PCR of the present invention are particularly preferred, in terms of their high speed, high sensitivity, and simplicity.

The efficiency of gene expression screening can be improved by using DNA chips. Herein, a DNA chip refers to a miniature array in which oligonucleotides, DNA clones, or such are immobilized at a high density on a support surface, such as glass. For example, in order to carry out multiple expression screening, cDNA clones for each gene of interest, or oligonucleotides specific to each gene, are immobilized on a chip to produce a microarray. Next, RNAs are prepared from the dopaminergic neuron progenitor cells of the present invention, or cells differentiated, induced, or proliferated therefrom, and treated with reverse transcriptase to yield cDNAs. Next, the resulting cDNA samples are labeled with fluorescent tags or other tags, and then hybridized to the microarray. As a result, genes that are actively expressed in the cells have a higher percentage of total labeled cDNA, while genes that are not significantly expressed have a lower percentage. Namely, the fluorescent signal intensity, which represents hybridization between a labeled cDNA and a cDNA clone or an oligonucleotide on the chip, reflects the expression level of each sequence in the labeled cDNA, and thereby enables quantification of gene expression.

In addition, multiple genes in the dopaminergic neuron progenitor cells of the present invention, or cells differentiated, induced, or proliferated therefrom, can be simultaneously analyzed by mRNA differential display, which involves reverse transcription PCR using degenerate PCR primers. First, a modified oligo dT primer is prepared, in which one or two nucleotides at the 3' terminus in the poly A tail of a given mRNA have been altered. Then, a reverse transcription reaction is carried out using the total RNAs isolated from the dopaminergic neuron progenitor cells of the present invention, cells differentiated or proliferated therefrom, or control cells to be used for expression comparison (Liang et al. (1993) Nucleic Acids Res. 21: 3269-3275). If the altered nucleotide is a "G", then mRNAs with a "C" immediately before the poly A tail can be selectively amplified. If the altered nucleotides are "CA", then mRNAs with "TG" immediately before the poly A tail can be selectively amplified. Next, an arbitrary nucleotide sequence of about 10 nucleotides in length is prepared for use as a second primer, and a PCR amplification reaction is carried out using the modified oligo dT primer and this second primer. The amplification product is subjected to size fractionation by electrophoresis using a long polyacrylamide gel. By using such methods, cDNAs derived from the mRNAs specifically expressed in either of the cells of the present invention or the control cells can be detected as bands only present in the samples that have been electrophoresed. These methods can also be used to analyze expression of unidentified genes.

SAGE analysis does not require a special device for detection, and is one of the preferred analytical methods for simultaneously detecting the expression of a large number of transcription products. First, poly A$^+$ RNA is extracted from the dopaminergic neuron progenitor cells of the present invention, or cells differentiated, induced, or proliferated therefrom, using standard methods. Next, the RNAs are converted into cDNAs using a biotinylated oligo (dT) primer, and are then treated with a four-base recognizing restriction enzyme (Anchoring Enzyme: AE). Here, the AE-treated fragments contain a biotin group at their 3' terminus Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. Herein, the linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. The clone's determined nucleotide sequence can be used to obtain a read-out of consecutive ditags of constant length. The presence of mRNA corresponding to each tag can then be identified once from the determination of the clone's nucleotide sequence and information on the sequence tags thus obtained.

Subtraction hybridization is frequently used to clone genes with different expression levels in various tissues or cells, and can also be used to clone genes specifically expressed in the dopaminergic neuron progenitor cells of the present invention, or cells differentiated, induced, or proliferated therefrom. First, from the dopaminergic neuron progenitor cells of the present invention, a DNA sample of a cell to be tested is prepared (hereinafter referred to as "test DNA"). Next, a DNA of a cell to be compared is prepared (hereinafter referred to as "driver DNA"). The test and driver DNAs can also be used interchangeably. In any case, genes present in the test DNA but absent from the driver DNA are detected. Next, the prepared test DNA is mixed with a large excess of driver DNA, denatured to form single-stranded DNA, then annealed. By regulating the annealing conditions, specific sequences absent from the driver DNA can be isolated as double-stranded DNAs comprising only the test DNA sequence. For further detail on this method see, Swaroop et al. (1991) Nucleic Acids Res. 19: 1954 and Yasunaga et al. (1999) Nature Genet. 21: 363-9.

The RDA method is a method that uses PCR to selectively amplify a sequence of a test DNA that is absent in a driver DNA, and can be used in the present invention similarly to other previously described methods. For more details on the procedure see Lisitsyn (1995) Trends Genet. 11: 303-7 and Schutte et al. (1995) Proc. Natl. Acad. Sci. USA 92: 5950-4.

Genes specific to dopaminergic neuron progenitor cells, or cells differentiated, induced, or proliferated therefrom, are detected and isolated as described, and can be inserted into vectors or such, for sequence determination and expression analysis using the various known methods described above.
<Screening Using Dopaminergic Neuron Progenitor Cell Maturation as an Index>

The present invention provides screening methods that comprise the step of contacting test substances with the dopaminergic neuron progenitor cells of the present invention, and the step of detecting the differentiation or proliferation of the progenitor cells that results from that contact. Since compounds obtained by this screening method demonstrate a regulatory function in the differentiation, proliferation, and such, of dopaminergic neurons, they are considered useful as potential therapeutic candidates for diseases caused by defects in dopaminergic neurons. The dopaminergic neuron progenitor cells of the present invention include cells selected by using the polynucleotide probes or antibodies of the present invention, and cells obtained by the proliferation and/or differentiation induction of these cells.

Here, the "test substance" may be any type of compound, examples of which include the expression products of gene libraries, synthetic low molecular weight compound libraries, synthetic peptide libraries, antibodies, substances released by bacteria, cell (microbial, plant, or animal) extracts, cell (microbial, plant, or animal) culture supernatants, purified or partially purified polypeptides, marine organisms, plant or animal extracts, soil, random phage peptide display libraries, and such.

Cell differentiation and proliferation can be detected by comparison with cell status in the absence of the test substance. Cell differentiation and proliferation can be detected by morphological observation under a microscope or by detection or quantification of substances produced in cells, such as dopamine.
<Analysis of Lrp4 Expression Regulatory Region>

Using a sequence of the Lrp4 gene, an expression regulatory region of Lrp4 can be cloned from genomic DNA by known methods. For example, a method for establishing the transcriptional start site, such as the 51 mapping method, is known and can be used (Cell Engineering, Supplement 8, New Cell Engineering Experiment Protocol, Cancer Research Division, The Institute of Medical Science, The University of Tokyo ed., Shujunsha Publishing (1993) pp. 362-374). In general, the expression regulatory region of a gene can be cloned by screening genomic DNA libraries, using probe DNAs comprising a 15-100 bp segment, and preferably a 30-50 bp segment, of the gene's 5' terminus (in the present invention, all or a portion of nucleotides of SEQ ID NO: 1 or SEQ ID NO: 2). A clone obtained in this manner contains a 5' non-coding region of 10 kbp or more, and is shortened or fragmented by exonuclease treatment, or such. Finally, the shortened sequence portion, comprising a potential expression regulatory region, is evaluated for the strength, regulation and such of its expression using a reporter gene, thereby making it possible to determine the minimum unit required to maintain the activity of the Lrp4 expression regulatory region.

Gene expression regulatory regions can be predicted using a program such as Neural Network (http://www.fruitfly.org./seq_tools/promoter.html; Reese et al., Biocomputing: Proceedings of the 1996 Pacific Symposium, Hunter and Klein ed., World Scientific Publishing Co., Singapore, (1996)). Moreover, a program for predicting the minimum unit required for the activity of an expression regulatory region is also known and can be used (http://biosci.cbs.umn-.edu./software/proscan/promoterscan.htm; Prestridge (1995) J. Mol. Biol. 249: 923-932).

The expression regulatory region of the Lrp4 gene isolated in this manner can be used to produce proteins of interest specifically in dopaminergic neuron proliferative progenitor cells in vivo.
<Ligand for Lrp4>

The Lrp4 polypeptides have a transmembrane domain, and thus in nature are thought to exist embedded within the cell membrane. Due to its expression in dopaminergic neuron progenitor cells, Lrp4 is believed to be involved in the regulation of dopaminergic neuron progenitor cell proliferation and in neuron differentiation and maturation. Thus, potential ligands that may demonstrate an agonistic or antagonistic function towards Lrp4 may be used to regulate the differentiation of dopaminergic neurons in vivo, ex vivo, and in vitro. In identifying ligands for Lrp4 polypeptides, an Lrp4 polypeptide and a candidate compound are first contacted and tested for the presence of binding. In this case, the Lrp4 polypeptide can be used when immobilized on a support, or embedded in the cell membrane. There are no particular limitations on the candidate compounds, examples of which include expression products of gene libraries, natural substances derived from marine organisms, extracts of various types of cells, known compounds and peptides, natural substances derived from plants, body tissue extracts, microbial culture supernatants and peptide groups randomly produced by the phage display method (J. Mol. Biol. 222: 301-10 (1991)). In addition, the candidate compound may be labeled for detection of binding.

<Inhibition of Lrp4 Expression>

Since the present invention clearly demonstrates that Lrp4 mRNA is transiently expressed in dopaminergic neuron proliferative progenitor cells, Lrp4 may be involved in the control of progenitor cell proliferation as well as neuron differentiation and maturation. Thus, substances that inhibit Lrp4 gene expression may be used to control the differentiation of dopaminergic neurons in vivo, ex vivo, and in vitro. Examples of substances capable of inhibiting gene expression include antisense nucleic acids, ribozymes, and double-stranded RNAs (small interfering RNA; siRNA). Thus, the present invention provides such antisense nucleic acids, ribozymes, and double-stranded RNAs.

Examples of antisense mechanisms that suppress target gene expression include: (1) inhibition of transcription initiation via triplex formation, (2) transcription suppression through hybrid formation at sites of local open-loop structures formed by RNA polymerase, (3) transcription inhibition through hybrid formation with RNA during synthesis, (4) suppression of splicing through hybrid formation at intron-exon junctions, (5) suppression of splicing through hybrid formation at sites of spliceosome formation, (6) suppression of mRNA migration to the cytoplasm through hybrid formation with mRNA, (7) suppression of splicing through hybrid formation at a capping site or poly A addition site, (8) suppression of translation initiation through hybrid formation at binding sites of translation initiation factors, (9) translation suppression through hybrid formation at ribosome binding sites, (10) suppression of peptide chain elongation through hybrid formation at mRNA coding regions or polysome binding sites, and (11) suppression of gene expression through hybrid formation at sites of nucleic acid/protein interaction (Hirashima and Inoue, "New Biochemistry Experiment Course 2, Nucleic Acids IV, Gene Replication and Expression", Japanese Biochemical Society edit., Tokyo Kagaku Dozin Publishing, pp. 319-347 (1993)).

An Lrp4 antisense nucleic acid of the present invention may be a nucleic acid that inhibits gene expression by any of the mechanisms described in (1) to (11) above. Namely, it may contain an antisense sequence to not only a sequence of a coding region, but also a sequence of a non-coding region of a target gene whose expression is to be inhibited. A DNA that encodes an antisense nucleic acid can be used by linking to a suitable regulatory sequence that allows its expression. The antisense nucleic acid does not need to be completely complementary to the coding region or non-coding region of a target gene, as long as it can effectively inhibit the expression of this gene. Such antisense nucleic acids have a chain length of at least 15 bp or more, preferably 100 bp or more, and more preferably 500 bp or more, and are normally within 3000 bp, preferably within 2000 bp, and more preferably within 1000 bp. It is preferable that such antisense nucleic acids share an identity of 90% or more, and more preferably 95% or more, with the complementary chain of a target gene transcription product. These antisense nucleic acids can be prepared according to phosphorothionate methods (Stein (1988) Nucleic Acids Res. 16: 3209-21) or the like, using Lrp4 polynucleotides.

"Ribozyme" is a generic term referring to catalysts with an RNA component, and ribozymes are broadly classified into large ribozymes and small ribozymes. Large ribozymes cleave the phosphate-ester bonds of a nucleic acid, and after reaction, they leave 5'-phosphoric acid and 3'-hydroxyl group at the reaction sites. Large ribozymes are further classified into (1) group I intron RNAs, which carry out guanosine-initiated trans-esterification reactions at 5'-splice sites, (2) group II intron RNAs, which perform two-step self-splicing reactions via a lariat structure, and (3) RNA components of ribonuclease P, which cleave precursor tRNAs at their 5' side via hydrolysis reactions. In contrast, small ribozymes are comparatively small structural units (about 40 bp) that cleave RNAs, forming 5'-hydroxyl groups and 2'-3' cyclic phosphoric acids. Small ribozymes include, for example, hammerhead-type ribozymes (Koizumi et al. (1988) FEBS Lett. 228: 225) and hairpin-type ribozymes (Buzayan (1986) Nature 323: 349; Kikuchi and Sasaki (1992) Nucleic Acids Res. 19: 6751; Kikuchi (1992) Chemistry and Biology 30: 112). Since ribozymes are easily altered and synthesized, various methods for their modification are known. For example, hammerhead-type ribozymes that recognize and cleave nucleotide sequence UC, UU, or UA within a target RNA can be created, by designing the substrate binding portion of a ribozyme to be complementary to an RNA sequence near the target site (Koizumi et al. (1988) FEBS Lett. 228: 225; M. Koizumi and E. Ohtsuka (1990) Protein, Nucleic Acid and Enzyme 35: 2191; Koizumi et al. (1989) Nucleic Acids Res. 17: 7059). Hairpin-type ribozymes can also be designed and produced using known methods (Kikuchi and Sasaki (1992) Nucleic Acids Res. 19: 6751; Kikuchi (1992) Chemistry and Biology 30: 112).

Antisense nucleic acids and ribozymes of the present invention can also be used in viral vectors derived from retroviruses, adenoviruses, adeno-associated viruses, and such, or non-viral vectors that use liposomes, or naked DNAs, to control gene expression in cells using ex vivo or in vivo gene therapy.

RNA interference is a phenomenon in which the introduction of an artificial double-stranded RNA into cells causes RNAs having the same nucleotide sequence to be degraded (Fire et al. (1998) Nature 391: 806-11). There are no particular limitations on the siRNAs of the present invention, provided they inhibit transcription of Lrp4 mRNA. Normally, an siRNA is a combination of a sense and antisense chain to the sequence of a target mRNA, and has a nucleotide length of at least 10 to the same number of nucleotides as the target mRNA. These siRNAs preferably have a nucleotide length of 15 to 75, preferably 18 to 50, and more preferably 20 to 25 nucleotides.

In order to suppress Lrp4 expression, siRNAs can be introduced into cells using known methods. For example, a DNA is designed to encode, in a single strand, two RNA chains that compose an siRNA, and this is then incorporated into an expression vector, cells are transformed with the expression vector, and the siRNA can be expressed in the cells in the form of a double-stranded RNA with a hairpin structure. Plasmid expression vectors that continuously produce siRNA by transfection have also been designed (for example, RNAi-Ready pSIREN Vector, and RNAi-Ready pSIREN-RetroQ Vector (BD Biosciences Clontech)).

The nucleotide sequence of an siRNA can be designed using a computer program such as that disclosed at the Ambion website (http://www.ambion.com/techlib/misc/siRNA_finder.html). Kits for screening for functional siRNAs are also commercially available and can be used (for example, BD Knockout RNAi System (BD Biosciences Clontech).

EXAMPLES

The present invention will be specifically described using Examples, but it is not be construed as being limited thereto.

Example 1 Isolation and Sequence Analysis of a Gene Specific to Dopaminergic Neuron Progenitor Cells To isolate genes specific to dopaminergic neuron progenitor cells, the midbrain ventral region of E12.5 mice was additionally cut into two regions in the dorsoventral direction, and genes specifically expressed in the most ventral region containing dopaminergic neurons were identified by the subtraction (N-RDA) method. One of the isolated cDNA fragments was a fragment encoding Lrp4/Corin. Lrp4 encodes type II transmembrane proteins (FIG. 1).

(1) N-RDA Method
(1)-1. Adapter Preparation
The following oligonucleotides were annealed to each other, and prepared at 100 μM, (ad2: ad2S+ad2A, ad3: ad3S+ad3A, ad4: ad4S+ad4A, ad5: ad5S+ad5A, ad13: ad13S+ad13A)

```
ad2S:
                                    (SEQ ID NO: 5)
cagctccacaacctacatcattccgt ad2A:
                                    (SEQ ID NO: 6)
acggaatgatgt ad3S:
                                    (SEQ ID NO: 7)
gtccatcttctctctgagactctggt ad3A:
                                    (SEQ ID NO: 8)
accagagtctca ad4S:
                                    (SEQ ID NO: 9)
ctgatgggtgtcttctgtgagtgtgt ad4A:
                                    (SEQ ID NO: 10)
acacactcacag ad5S:
                                    (SEQ ID NO: 11)
ccagcatcgagaatcagtgtgacagt ad5A:
                                    (SEQ ID NO: 12)
actgtcacactg ad13S:
                                    (SEQ ID NO: 13)
gtcgatgaacttcgactgtcgatcgt ad13A:
                                    (SEQ ID NO: 14)
acgatcgacagt
```

(1)-2. cDNA Synthesis
Ventral midbrain regions were cut out of E12.5 mouse embryos (Japan SLC), and divided into two sections in the dorsoventral direction. Total RNA was prepared using the RNeasy Mini Kit (Qiagen), and double-stranded cDNA was synthesized using a cDNA Synthesis Kit (Takara). After digestion with restriction enzyme RsaI, ad2 was added. The cDNA was amplified by a 5-minute incubation at 72° C., 15 PCR cycles of 30 seconds at 94° C., 30 seconds at 65° C., and 2 minutes at 72° C., and a final 2-minute incubation at 72° C. using ad2S as the primer. In all cases, N-RDA PCR was carried out using a reaction solution containing the following components.

10× ExTaq 5 μl
2.5 mM dNTP 4 μl
ExTaq 0.25 μl
100 μM primer 0.5 μl
cDNA 2 μl
Distilled water 38.25 μl (1)-3. Driver Production
The ad2S-amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit (Qiagen), and digested with RsaI. 3 μg was used for each round of subtraction.

(1)-4. Tester Production
The ad2S amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit (Qiagen), and digested with RsaI. ad3 was added to 60 ng of the RsaI-digested cDNA.

(1)-5. First Round of Subtraction
The tester and the driver produced in Sections 1-3 and 1-4 above were mixed, subjected to ethanol precipitation, and then dissolved in 1 μl of 1×PCR buffer. After a 5-minute incubation at 98° C., 1 μl of 1×PCR buffer+1M NaCl was added. After another 5 minutes of incubation at 98° C., the tester and the driver were hybridized at 68° C. for 16 hours.

With ad3S as the primer, the hybridized cDNA was amplified by incubating at 72° C. for 5 minutes, and performing ten cycles of 30 seconds at 94° C., 30 seconds at 65° C., and 2 minutes at 72° C. Next, the amplified cDNA was digested with the Mung Bean Nuclease (Takara) and purified using a Qiaquick PCR Purification Kit. Then, it was amplified by incubating at 94° C. for 2 minutes, and performing 13 PCR cycles of 30 seconds at 94° C., 30 seconds at 65° C., and 2 minutes at 72° C., and a final 2-minute incubation at 72° C.

(1)-6. Normalization
1 μl of 2×PCR buffer was added to 8 ng of the cDNA amplified in the first round of subtraction. After incubating at 98° C. for 5 minutes, 2 μl of 1×PCR buffer+1 M NaCl was added. After another 5 minutes of incubation at 98° C., the cDNA was hybridized at 68° C. for 16 hours.

The hybridized cDNA was digested with RsaI, and purified using the Qiaquick PCR Purification Kit. Then, it was amplified with ad3 S as the primer by incubating at 94° C. for 2 minutes, and performing 11 PCR cycles of 30 seconds at 94° C., 30 seconds at 65° C., and 2 minutes at 72° C., and a final 2-minute incubation at 72° C. The PCR product was then digested with RsaI, followed by the addition of ad4.

(1)-7. Second Round of Subtraction 20 ng of the cDNA to which ad4 was added in Section 1-6 above was used as the tester and mixed with the driver of 1-3 above, and the same subtraction procedure used in Section 1-5 above was performed. Finally, ad5 was added to the cDNA following RsaI digestion.

(1)-8. Third Round of Subtraction 2 ng of the cDNA to which ad5 was added in section 1-7 above was used as the tester and mixed with the driver of 1-3 above, and the same subtraction procedure used in section 1-5 above was carried out. Finally, ad13 was added to the RsaI-digested cDNA.

(1)-9. Fourth Round of Subtraction 2 ng of the cDNA to which ad13 was added in section 1-8 above was used as the tester and mixed with the driver of 1-3 above, and the same subtraction procedure used in Section 1-5 above was carried out. The amplified cDNA was cloned into pCRII vector (Invitrogen), and its nucleotide sequence was analyzed using the ABI3100 sequence analyzer.

Example 2 Expression Analysis of the Lrp4 Gene

Next, an expression analysis of the Lrp4 gene by in situ hybridization was carried out according to the following protocol.

First, E12.5 mouse embryos were embedded in O.C.T., and fresh frozen sections of 16 µm thickness were prepared. After drying on a slide glass, the sections were fixed in 4% PFA at room temperature for 30 minutes. After washing with PBS, hybridization was carried out at 65° C. for 40 hours (1 µg/ml DIG-labeled RNA probe, 50% formamide, 5×SSC, 1% SDS, 50 µg/ml yeast RNA, 50 µg/ml Heparin). Subsequently, the sections were washed at 65° C. (50% formamide, 5×SSC, 1% SDS) and then treated with RNase (5 µg/ml RNase) at room temperature for 5 minutes. After washing with 0.2×SSC at 65° C. and washing with 1× TBST at room temperature, blocking was carried out (Blocking reagent: Roche). The sections were then reacted with alkaline phosphatase-labeled anti-DIG antibody (DAKO), washed (1×TBST, 2 mM Levamisole), and color developed using NBT/BCIP (DAKO) as the substrate.

Figure 2:
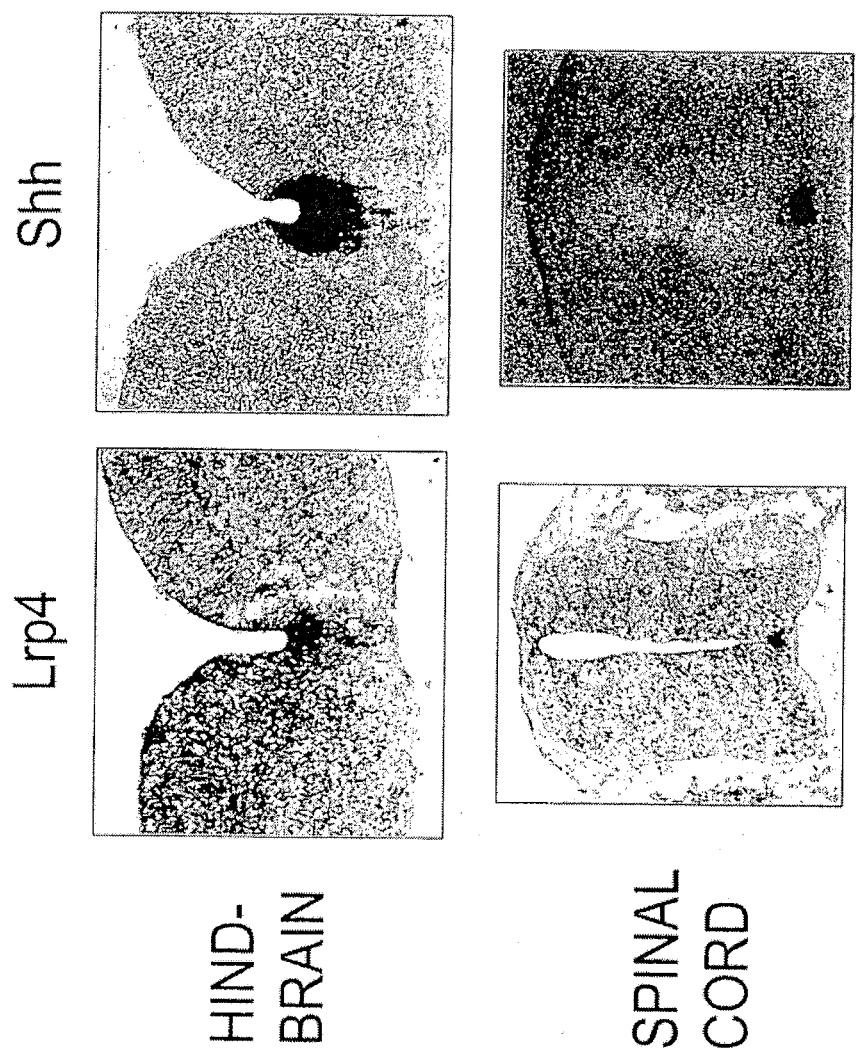
FIG. 2 is a set of photographs showing the results of Lrp4 and Shh mRNA expression analysis in E12.5 mouse ventral hindbrain region and spinal cord by in situ hybridization.
Figure 3:
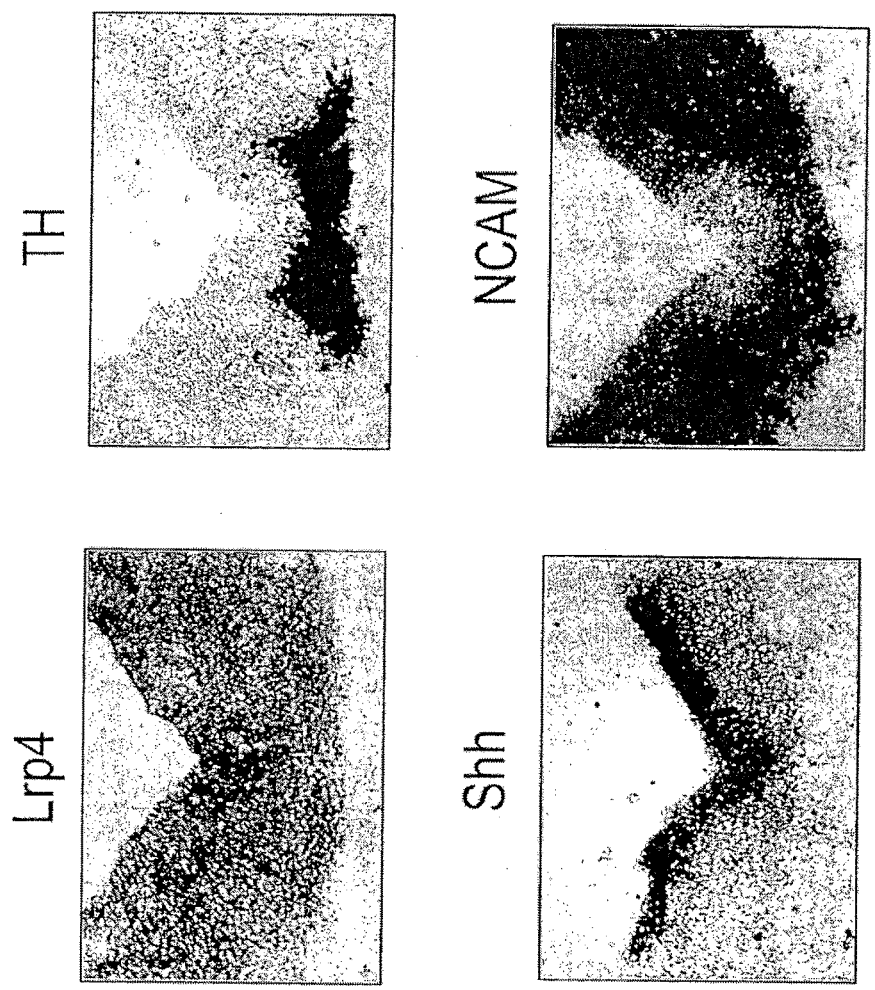
FIG. 3 is a set of photographs showing the results of Lrp4, Shh, tyrosine hydroxylase (TH), and NCAM mRNA expression analysis in E12.5 mouse ventral midbrain region by in situ hybridization.

The expression analysis by in situ hybridization showed that Lrp4 mRNA is specifically expressed in the ventral midline region from the midbrain to the hindbrain and the spinal cord at the stage E12.5, which corresponds to the time of dopaminergic neuron development. Lrp4 demonstrates a similar expression pattern to Shh mRNA from the hindbrain to the spinal cord, and was clearly determined to be specific to the floor plate, which is the organizer region (FIGS. 2 and 5). In the midbrain, Lrp4 expression was observed more centrally than the Shh mRNA expression zone (FIGS. 3 and 5).

Figure 4:
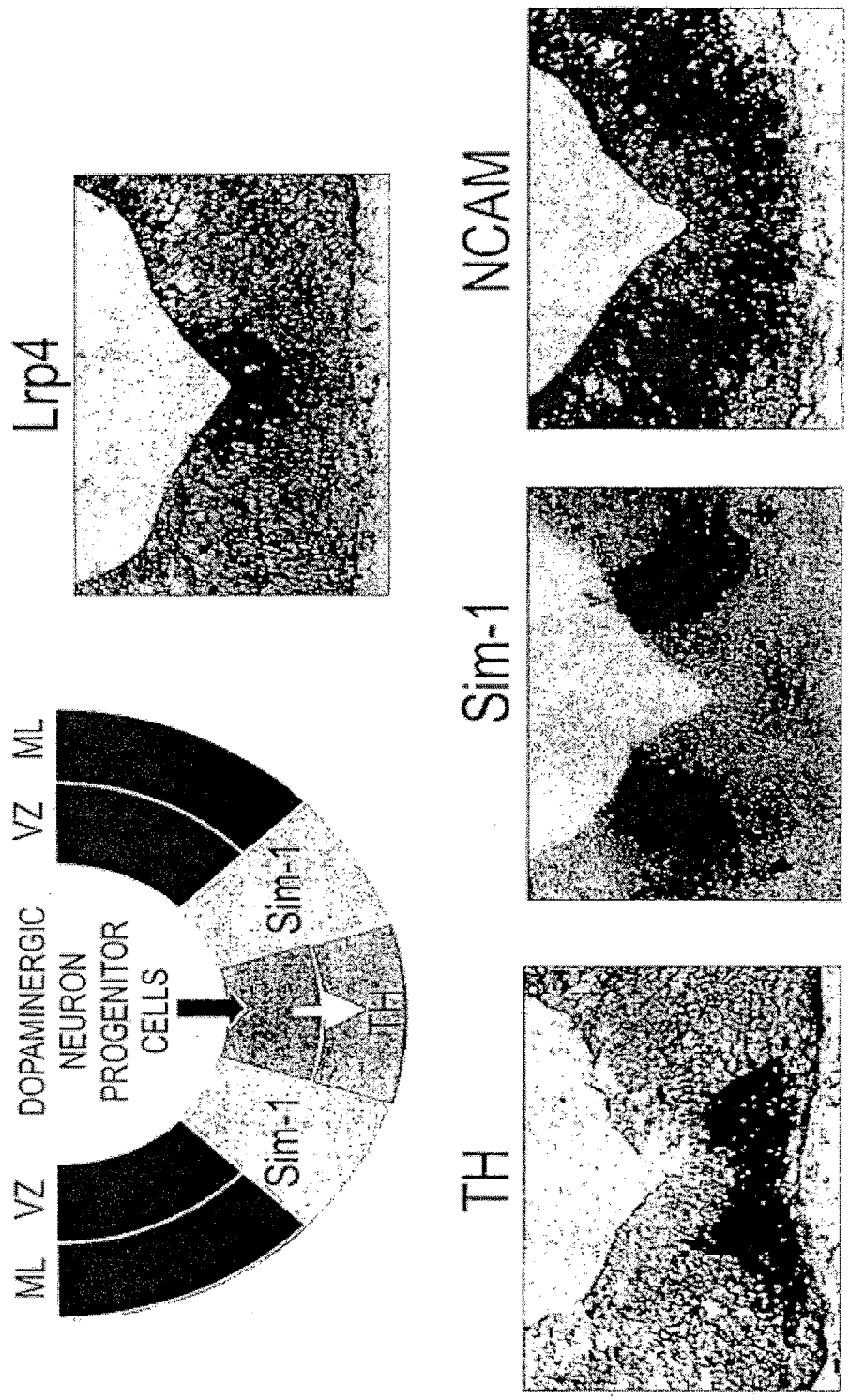
FIG. 4 is a schematic diagram of the Lrp4 expression pattern in the midbrain, and photographs indicating the expression of mRNAs of Lrp4, tyrosine hydroxylase (TH), Sim-1, and NCAM in the ventral midbrain of E12.5 mice analyzed by in situ hybridization. VZ: ventricular zone; and ML: mantle layer.
Figure 6:
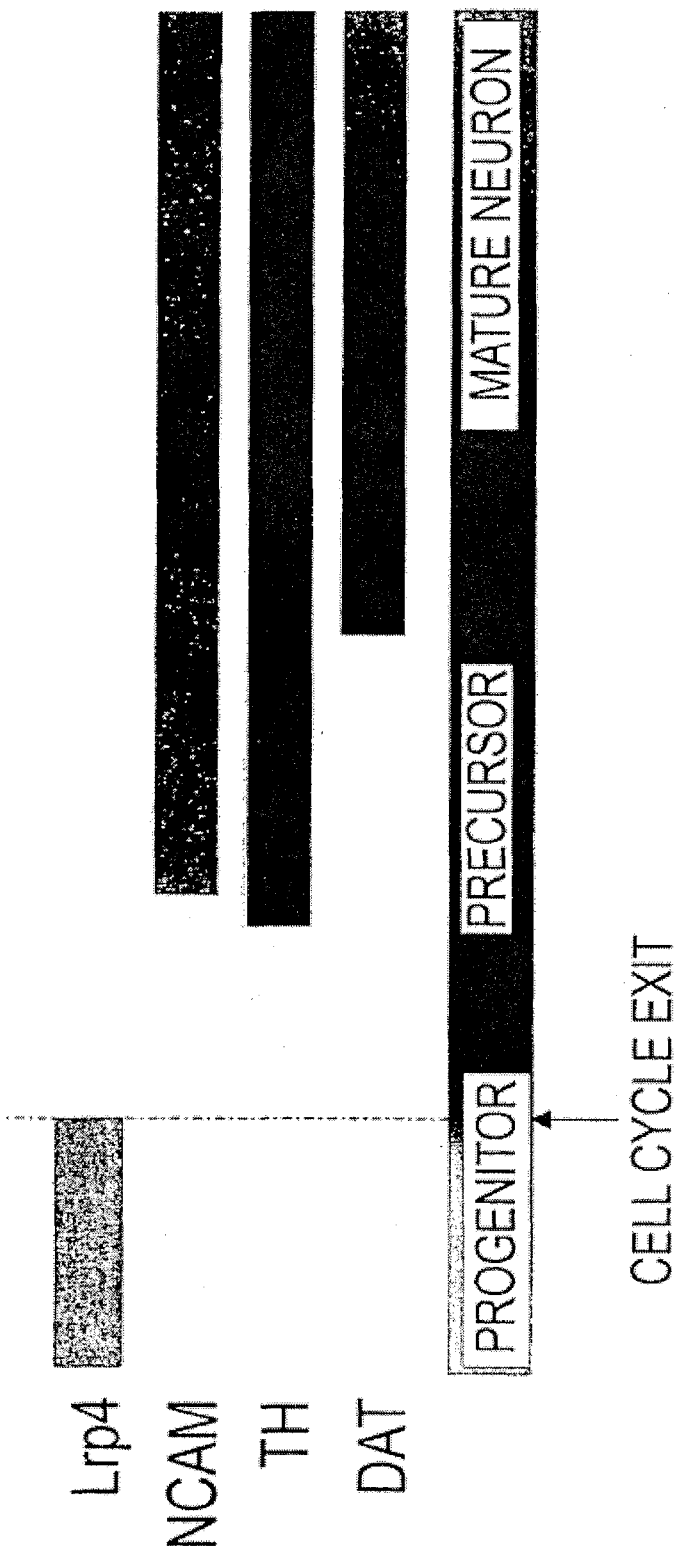
FIG. 6 schematically shows the timing of expression of Lrp4, NCAM, TH, and DAT mRNAs from the generation to maturation of dopaminergic neurons.

The results of comparison with the neuron maturation marker NCAM mRNA show that Lrp4 mRNA-expressing cells were proliferative progenitor cells in the NCAM mRNA-negative ventricular zone (VZ). Moreover, when compared with the expression of the dopaminergic neuron marker, TH mRNA, their expression regions completely overlapped along the dorsal-ventral axis (FIGS. 3 and 5), although expression of both TH mRNA and Lrp4 mRNA in the same cells was not observed since TH mRNA is only expressed in the mantle layer (ML). In general, neurons present in neural tubes are known to first proliferate in the VZ, exit cell cycle with the commencement of differentiation, and then mature after migrating to the outer ML. Thus, dopaminergic neuron proliferative progenitor cells are believed to proliferate in the VZ which lines the TH expression zone, and express TH mRNA after having migrated to the outside following cell cycle exit. Namely, Lrp4 mRNA is believed to be specifically expressed in the midbrain in dopaminergic neuron proliferative progenitor cells (FIGS. 4 and 6).

Example 3 Expression of Lrp4 in Dopaminergic Neurons Induced to Differentiate from ES Cells Next, whether Lrp4 is expressed in ES cells that have been induced to differentiate into dopaminergic neurons in vitro, was examined.

Figure 7:
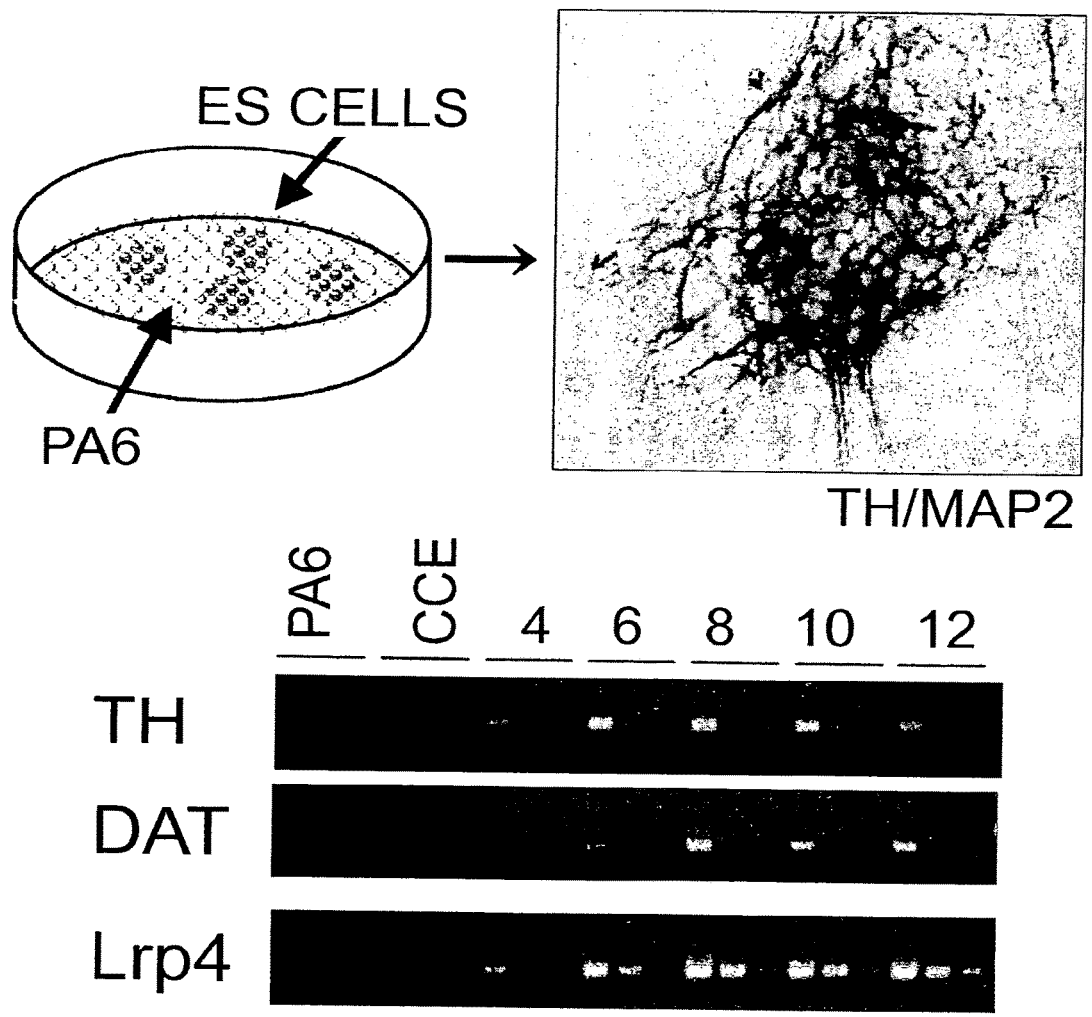
FIG. 7 (top panel consisting of a drawing and photograph) schematically shows the inhibition of differentiation of ES cells into dopaminergic neurons by the SDIA method. The bottom photograph shows the results of investigating the expression of Lrp4 mRNA in dopaminergic neurons differentiated from ES cells over time, using the SDIA method by RT-PCR.

First, dopaminergic neurons were induced to differentiate from ES cells using the SDIA method (Kawasaki et al. (2000) Neuron 28(1): 31-40) (see the upper part of FIG. 7). Cells were recovered 4, 6, 8, 10, and 12 days after induction, and total RNA was recovered using the RNeasy Mini Kit (Qiagen) followed by RT-PCR. In RT-PCR, cDNA was initially synthesized for 1 µg of total RNA using the RNA PCR Kit (TaKaRa). PCR was then carried out in the following reaction system, using as a template cDNA equivalent to 10 ng, 1 ng, and 0.1 ng.

| | |
|---|---|
| 10× ExTaq | 2 µl |
| 2.5 mM dNTP | 1.6 µl |
| ExTaq | 0.1 µl |
| 100 µM primer | 0.2 µl each |
| cDNA | 1 µl |
| Distilled water | 14.9 µl |

After incubating for 2 minutes at 94° C., 35 PCR cycles of 30 seconds at 94° C., 30 seconds at 65° C., and 2 minutes at 72° C. were carried out followed by incubating for 2 minutes at 72° C.

The sequences of the primers used are shown below.

```
Lrp4:
                                     (SEQ ID NO: 15)
TAGTCTACCACTGCTCGACTGTAACG/

(SEQ ID NO: 16)
CAGAGTGAACCCAGTGGACATATCTG

TH:
                                     (SEQ ID NO: 17)
GTTCCCAAGGAAAGTGTCAGAGTTGG/

(SEQ ID NO: 18)
GAAGCTGGAAAGCCTCCAGGTGTTCC

DAT:
                                     (SEQ ID NO: 19)
CTCCGAGCAGACACCATGACCTTAGC/

(SEQ ID NO: 20)
AGGAGTAGGGCTTGTCTCCCAACCTG
```

Figure 8:
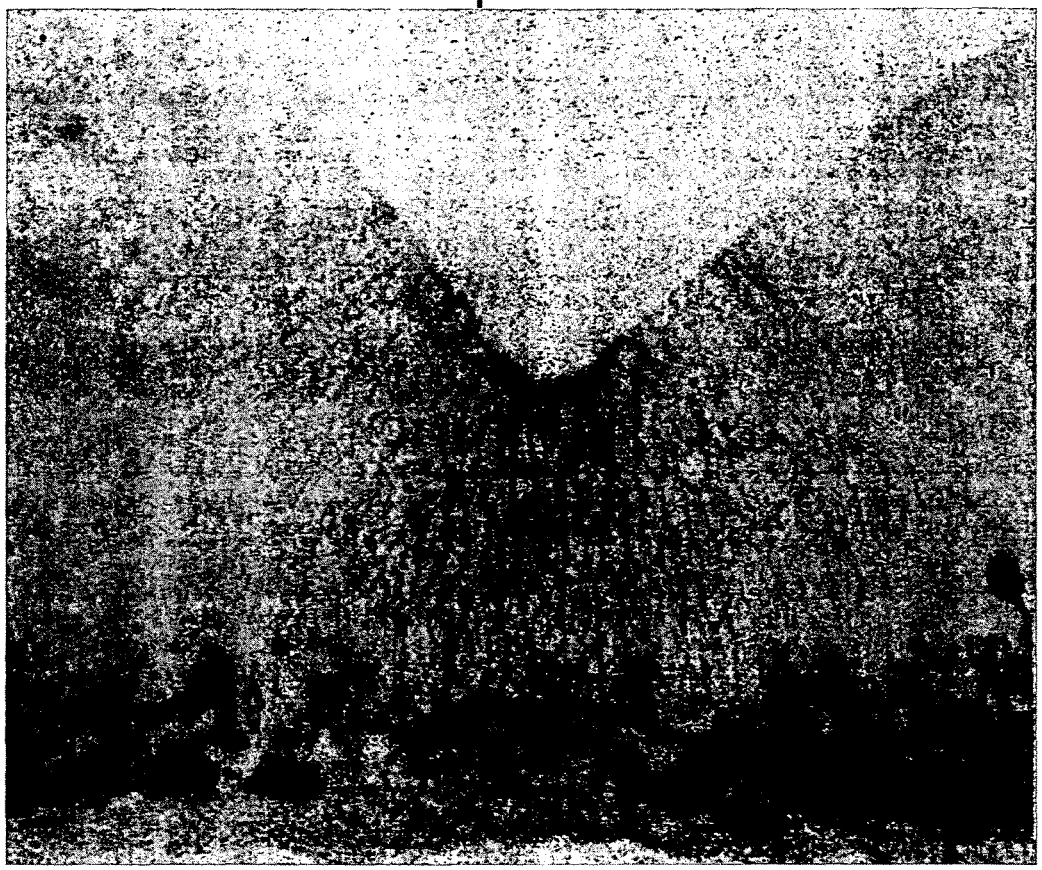
FIG. 8 is a photograph showing Lrp4 protein expression in the E12.5 mouse midbrain.

According to the results of expression analysis by RT-PCR, although Lrp4 is not expressed in ES cells (CCE) or stroma cells (PA6), expression was clearly induced starting on day 4 in the same manner as TH as a result of inducing differentiation (FIG. 8). Thus, the marker polynucleotide probes of the present invention are useful as markers not only when isolating dopaminergic neuron proliferative progenitor cells from the fetal midbrain, but also when isolating dopaminergic neuron proliferative progenitor cells that have been induced to differentiate from ES cells in vitro.

Example 4 Analysis of Lrp4 Protein Expression

The anti-Lrp4 antibody was produced by the protocol described below using the extracellular region encoding sequence in the Lrp4 gene, and expression analyses were performed using immunohistological staining.

First, the extracellular region (161 to 502 amino acids) encoding sequence in the Lrp4 gene was introduced into 293E cells, and the extracellular region of the Lrp4 protein was expressed and collected. Hamsters were immunized with the collected protein, and lymphocytes were removed therefrom and fused with myeloma cells. The fused cells were cultured to obtain a culture supernatant. On day 12.5 mouse embryos were then fixed with 4% PFA/PBS(−) at 4° C. for two hours, then the solution was replaced with 20% sucrose/PBS(−) at 4° C. overnight, and the embryos were embedded with OTC. 12-μm-thick sections were made, attached on a slide glass, dried at room temperature for 30 minutes, and wetted with PBS(−) again. The sections were blocked (10% normal donkey serum and 10% normal goat serum/Block Ace) at room temperature for 20 minutes, and then reacted with the anti-Lrp4 monoclonal antibody produced as described above (mixture of FERM BP-10315 and FERM BP-10316 [each ¼-diluted culture supernatants, 10% normal donkey serum, 10% normal goat serum, and 2.5% Block Ace/PBS]) and the anti-TH antibody (Chemicon, 0.7 μg/mL, 10% normal donkey serum, 10% normal goat serum, and 2.5% Block Ace/PBS) at room temperature for one hour, and further reacted at 4° C. overnight. The sections were washed four times with 0.1% Triton X-100/PBS(−) at room temperature for 10 minutes. Cy3-labeled anti-hamster IgG antibody or the FITC-labeled anti-mouse IgG antibody (Jackson, 10 μg/mL, 10% normal donkey serum, 10% normal goat serum, and 2.5% Block Ace/PBS) was reacted with the sections at room temperature for one hour. Then, the sections were washed as described above, then washed with PBS(−) at room temperature for 10 minutes, and sealed.

As a result of expression analysis by immunohistological staining using the produced anti-Lrp4 monoclonal antibody, expression of the Lrp4 protein was observed in the ventral midbrain at E12.5, the stage when the dopaminergic neuron developed (FIG. 8) as shown by expression analysis using in situ hybridization. Compared with expression of the TH protein, which was the dopaminergic neuron marker, the Lrp4 protein was expressed in the most ventral midbrain (VZ side) where the TH protein was expressed. Accordingly, it appeared that the Lrp4 protein is expressed in the dopaminergic neuron progenitor cells.

Next, using the anti-Lrp4 monoclonal antibody, Lrp4-expressing cells were detected by flow cytometry.

First, ES cells were induced to differentiate to dopaminergic neuron progenitor cells in vitro using the SDIA method. A cell population comprising the cells was dispersed using a cell dissociation buffer (Invitrogen), and stained with the anti-Lrp4 monoclonal antibody (mixture of FERM BP-10315 and FERM BP-10316 [each ¼-diluted culture supernatant, 1% fetal calf serum, and 1 mM EDTA/SDIA differentiation medium]) at 4° C. for 20 minutes without fixing and permeabilization. Subsequently, the cells were washed three times with 1% fetal calf serum and 1 mM EDTA/SDIA differentiation medium at 4° C. for 3 minutes. The cells were stained with biotin-labeled anti-hamster IgG antibody (Jackson, 10 μg/mL, 1% fetal calf serum and 1 mM EDTA/SDIA differentiation medium) at 4° C. for 20 minutes, and washed as described above. Then, the cells were stained with PE-labeled streptavidin (Pharmingen, 20 μg/mL, 1% fetal calf serum and 1 mM EDTA/SDIA differentiation medium) at 4° C. for 20 minutes, and washed as described above. After staining, the Lrp4-expressing cells were detected by a flow cytometer.

Figure 9:
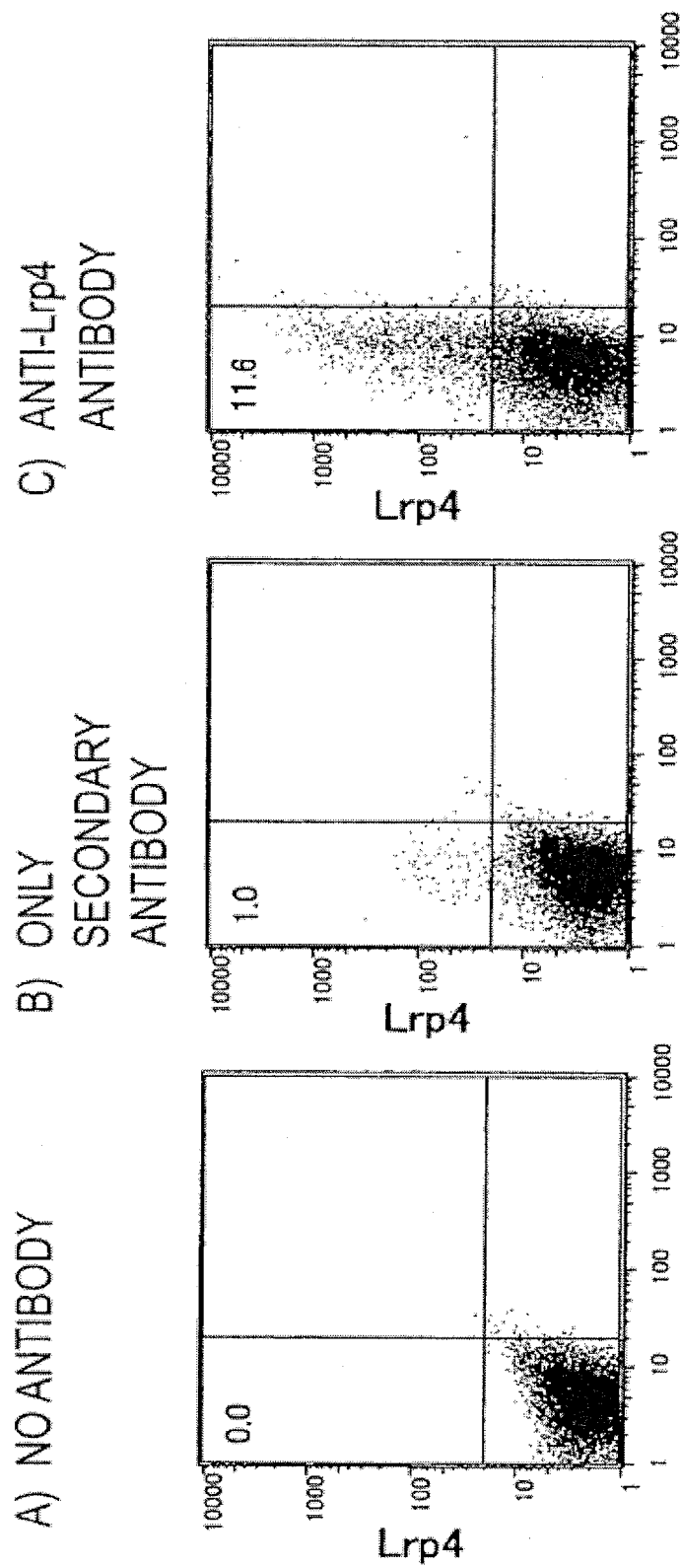
FIG. 9 shows Lrp4 protein expression on the SDIA-differentiated cell surface analyzed by flow cytometry using the anti-Lrp4 antibody.

The results of detecting the Lrp4-expressing cells by flow cytometry using the produced anti-Lrp4 monoclonal antibody detected an Lrp4 protein-expressing population (FIG. 9). Since the Lrp4 protein-expressing cells could be detected without fixing and permeabilization, it appeared that living Lrp4 protein-expressing cells can be separated by using a flow cytometer equipped with a cell sorter. The Lrp4 protein is thought to be expressed in the dopaminergic neuron progenitor cells, and thus the anti-Lrp4 antibody appeared to be useful for the separation of the dopaminergic neuron progenitor cells.

Example 5 Separation of Lrp4-Expressing Cells by Antibodies

Lrp4 protein-positive cells separated using the anti-Lrp4 antibody were characterized.

First, a cell population comprising E12.5 mouse fetus ventral midbrain and dopaminergic neuron progenitor cells, induced in vitro to differentiate from ES cells by the SDIA method, was stained with the anti-Lrp4 antibody by the method described in Example 4. Lrp4-positive and -negative cells were separated using a cell sorter. Total RNA was collected from the cells immediately after separation using an RNeasy mini kit (Qiagen). Then, cDNA was synthesized, and amplified by the same method as described in Example 1 to use as a template in RT-PCR. The PCR was performed using cDNAs corresponding to the amplified cDNA equivalent to 4 ng, 0.4 ng, and 0.04 ng by the following reaction system.

| | |
|---|---|
| 10x ExTaq | 1 μL |
| 2.5 mM dNTP | 0.8 μL |
| ExTaq | 0.05 μL |
| 100 μM primers | 0.1 μL each |
| cDNA | 1 μL |
| Distilled water | 6.95 μL |

PCR was carried out under conditions of 94° C. for 2 minutes, 26 cycles of 94° C. for 30 seconds, 65° C. for 30 seconds, and 72° C. for 2 minutes, and finally 72° C. for 2 minutes.

The sequences of the primers used are shown below.

```
Lrp4:
                                  (SEQ ID NO: 15)
TAGTCTACCACTGCTCGACTGTAACG/

(SEQ ID NO: 16)
CAGAGTGAACCCAGTGGACATATCTG

TH:
                                  (SEQ ID NO: 17)
GTTCCCAAGGAAAGTGTCAGAGTTGG/

(SEQ ID NO: 18)
GAAGCTGGAAAGCCTCCAGGTGTTCC

Nurr1:
                                  (SEQ ID NO: 21)
CACTCCTGTGTCTAGCTGCCAGATGC/

(SEQ ID NO: 22)
AGTGCGAACACCGTAGTGCTGACAGG
```

Nestin:
(SEQ ID NO: 23)
GATGAAGAAGAAGGAGCAGAGTCAGG/

(SEQ ID NO: 24)
ATTCACTTGCTCTGACTCCAGGTTGG

MAP2:
(SEQ ID NO: 25)
CCATGATCTTTCCCCTCTGGCTTCTG/

(SEQ ID NO: 26)
TTTGGCTGGAAAGGGTGACTCTGAGG

Figure 10:
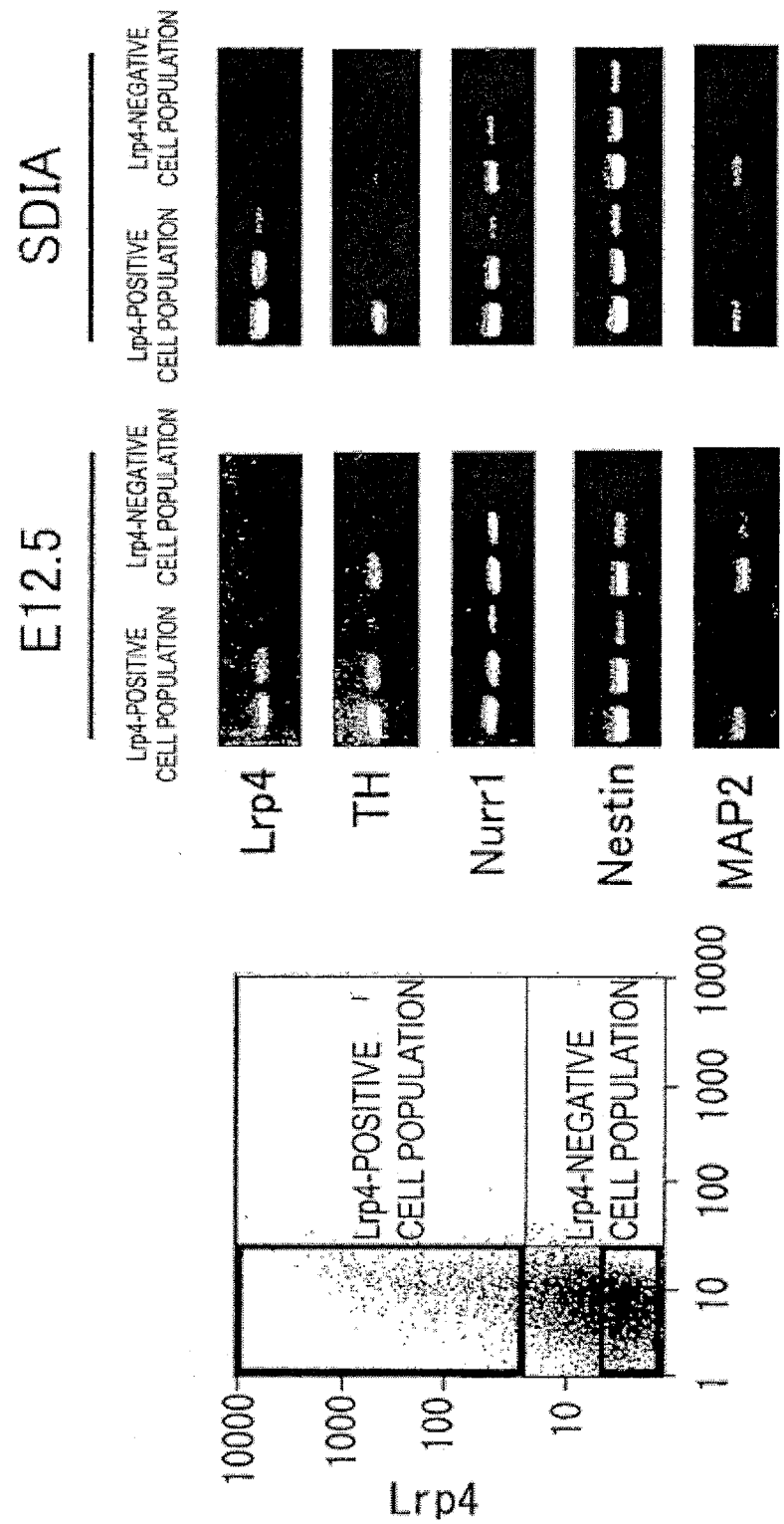
FIG. 10 is a set of photographs showing the expression of various dopaminergic neuron markers in Lrp4-positive cells analyzed by RT-PCR.
Figure 11:
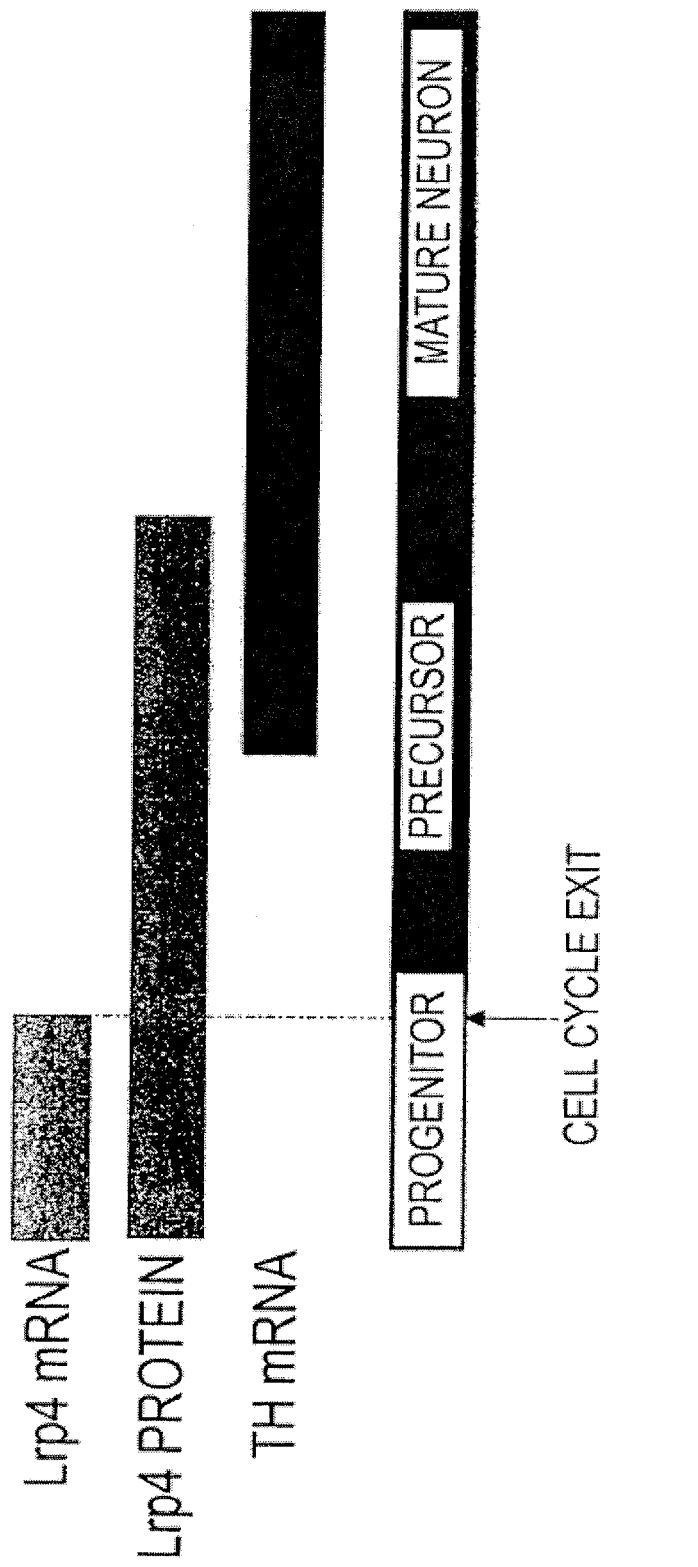
FIG. 11 schematically shows the expression periods of Lrp4 mRNA and protein, and TH mRNA from the development to maturation of dopaminergic neurons. This shows that both dopaminergic neuron proliferative progenitor cells and postmitotic dopaminergic neuron precursor cells are present in Lrp4-expressing cells.

As expected, the results of expression analysis by the RT-PCR indicated expression of the proliferative progenitor cell marker Nestin. It was also revealed that cells expressing MAP2, which was the postmitotic neuron marker, were included in the Lrp4 protein-positive cell population (FIG. 10). Therefore, it was found that Lrp4 protein expression is maintained after stopping mRNA expression, and that Lrp4 protein is useful as a marker for separating not only dopaminergic neuron proliferative progenitor cells but also postmitotic dopaminergic neuron precursor cells (FIG. 11). Furthermore, since Nurr1 and TH, which are markers for postmitotic dopaminergic neuron precursor cells, were expressed at higher levels compared to the Lrp4-negative cell population, Lrp4-positive cells were confirmed to be dopaminergic neuron lineage progenitor cells (FIG. 10).

Next, the present inventors analyzed the ratio of proliferative progenitor cells to postmitotic precursor cells in the Lrp4 protein-positive cell population separated by the anti-Lrp4 antibody.

The separated cells were seeded on a glass slide coated with poly-L-ornithine (Sigma, 0.002% in PBS), laminin (Invitrogen, 5 µg/mL in PBS), and fibronectin (Sigma, 5 µg/mL in PBS), and incubated in N2 (Invitrogen, 1×), B27 (Invitrogen 1×), ascorbic acid (Sigma, 200 µM), and BDNF (Invitrogen, 20 ng/mL)/SDIA differentiation medium at 37° C. for 40 minutes to adhere thereon. The adherent cells were fixed in 4% PFA/PBS at 4° C. for 20 minutes, and washed twice with PBS at 4° C. for 10 minutes. Permeabilization with 0.3% Triton X-100/PBS was performed at room temperature for 15 minutes, and blocking with 10% normal donkey serum/Block Ace was performed at room temperature for 20 minutes. Then, the cells were reacted with anti-Nestin antibody (Chemicon, 2 µg/mL, 10% normal donkey serum, 2.5% Block Ace, 0.1% Triton X-100/PBS) or anti-βIII-tubulin antibody (BABCO, 1/2000, 0.5 µg/mL, 10% normal donkey serum, 2.5% Block Ace, and 0.1% Triton X-100/PBS) at room temperature for one hour, and subsequently at 4° C. overnight. On the next day, the cells were washed three times with 0.1% Triton X-100/PBS at room temperature for 5 minutes, and reacted with the FITC-labeled anti-mouse IgG antibody or the Cy5-labeled anti-rabbit IgG antibody (both from Jackson, 10 µg/mL, 10% normal donkey serum, 2.5% Block Ace, and 0.1% Triton X-100/PBS) at room temperature for 30 minutes. Subsequently, the cells were washed as described above, then washed with PBS at room temperature for 5 minutes, and sealed for observation.

Also, the separated cells were similarly seeded on a glass slide, and cultured in the above-described medium supplemented with BrdU (Roche, 5-Bromo-2'-deoxy-uridine Labeling and Detection kit II, 1×) at 37° C. for 18 hours. Then, the above-described procedures were similarly carried out until the blocking step. The cells were reacted in 2 N HCl at 37° C. for 20 minutes, washed three times with PBS, and then reacted with anti-BrdU antibody and DNase (Roche, 5-Bromo-2'-deoxy-uridine Labeling and Detection kit II, 1× conc. in incubation buffer) at 37° C. for 30 minutes. Furthermore, the cells were reacted with anti-BrdU antibody (Sigma, 44 µg/mL, 10% normal donkey serum, 2.5% Block Ace, and 0.1% Triton X-100/PBS) at room temperature for one hour, and subsequently at 4° C. overnight. The next day, the cells were washed three times with 0.1% Triton X-100/PBS at room temperature for 5 minutes, and then reacted with the FITC-labeled anti-mouse IgG antibody (Jackson, 10 µg/mL, 10% normal donkey serum, 2.5% Block Ace, and 0.1% Triton X-100/PBS) at room temperature for 30 minutes. Subsequently, the cells were washed, and sealed for observation as described above.

Figure 12:
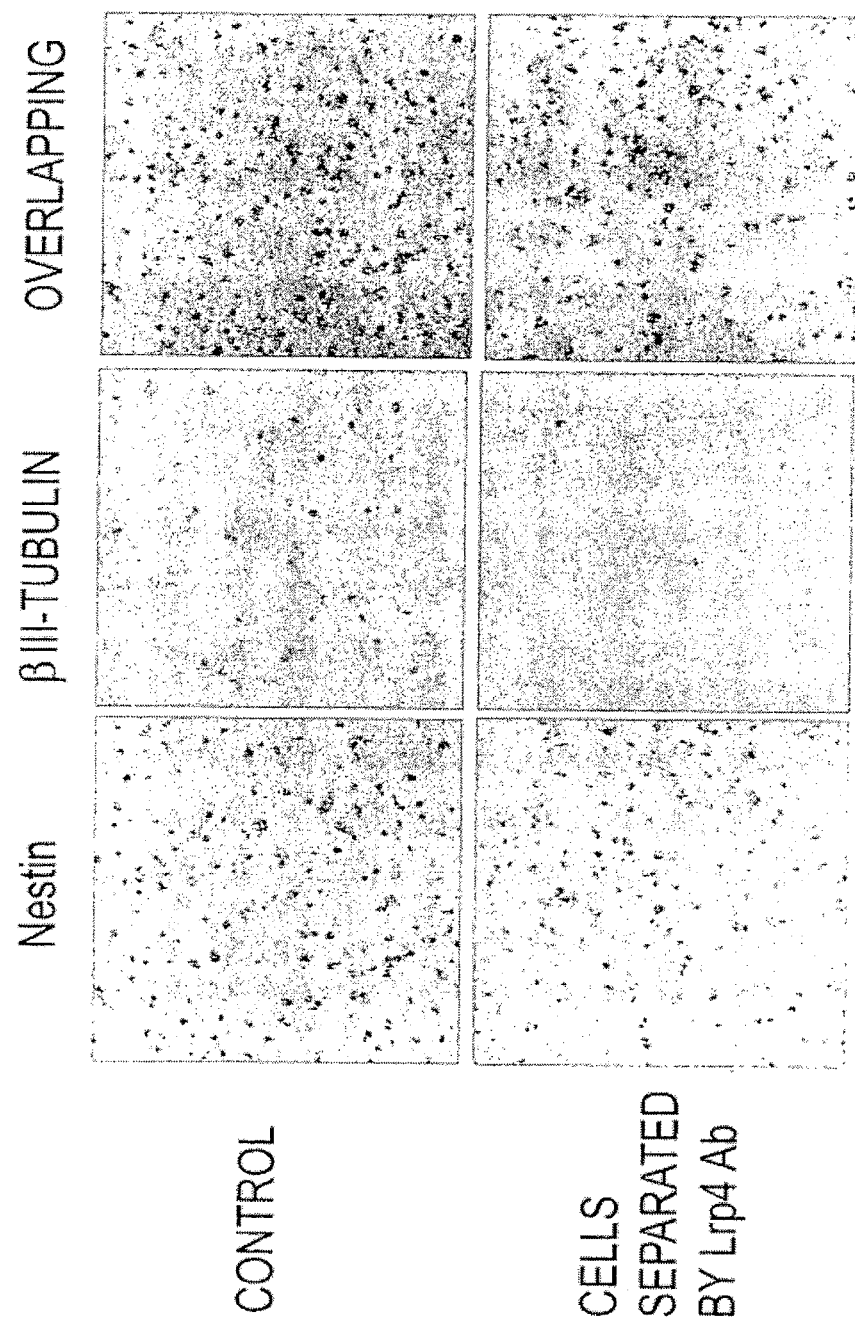
FIG. 12 is a set of photographs showing the results of examining the differentiation stages of Lrp4-positive cells.

As a result of the marker staining, it was revealed that a majority of the Lrp4-positive cells are Nestin-positive proliferative progenitor cells and that a part thereof is positive for the postmitotic marker βIII-tubulin (FIG. 12). In addition, the separated cells were confirmed to frequently incorporate BrdU, and to actually proliferate in vitro (FIG. 13).

Next, the present inventors confirmed that the separated Lrp4-positive cells differentiate into the dopaminergic neurons.

The separated cells were seeded on a glass slide coated with poly-L-ornithine (Sigma, 0.002% in PBS), laminin (Invitrogen, 5 µg/mL in PBS), and fibronectin (Sigma, 5 µg/mL in PBS), and incubated in N2 (Invitrogen, 1×), B27 (Invitrogen 1×), ascorbic acid (Sigma, 200 µM), BDNF (Invitrogen, 20 ng/mL), and bFGF (R&D, 10 ng/ml)/SDIA differentiation medium at 37° C. for 24 hours. The cells were then further cultured in the above medium without bFGF for another six days. The cultured cells were fixed in 4% PFA/PBS at 4° C. for 20 minutes, and washed twice with PBS at 4° C. for 10 minutes. Permeabilization with 0.3% Triton X-100/PBS was performed at room temperature for 15 minutes, and blocking with 10% normal donkey serum/ Block Ace was performed at room temperature for 20 minutes. Then, the cells were reacted with anti-TH antibody (Chemicon, 0.3 µg/mL, 10% normal donkey serum, 2.5% Block Ace, 0.1% Triton X-100/PBS) or anti-βIII-tubulin antibody (BABCO, 1/2000, 0.5 µg/mL, 10% normal donkey serum, 2.5% Block Ace, and 0.1% Triton X-100/PBS) at room temperature for one hour, and subsequently at 4° C. overnight. On the next day, the cells were washed three times with 0.1% Triton X-100/PBS at room temperature for 5 minutes, and reacted with the FITC-labeled anti-mouse IgG antibody or the Cy5-labeled anti-rabbit IgG antibody (both from Jackson, 10 µg/mL, 10% normal donkey serum, 2.5% Block Ace, and 0.1% Triton X-100/PBS) at room temperature for 30 minutes. Subsequently, the cells were washed as described above, then washed with PBS at room temperature for 5 minutes, and sealed for observation.

Figure 14:
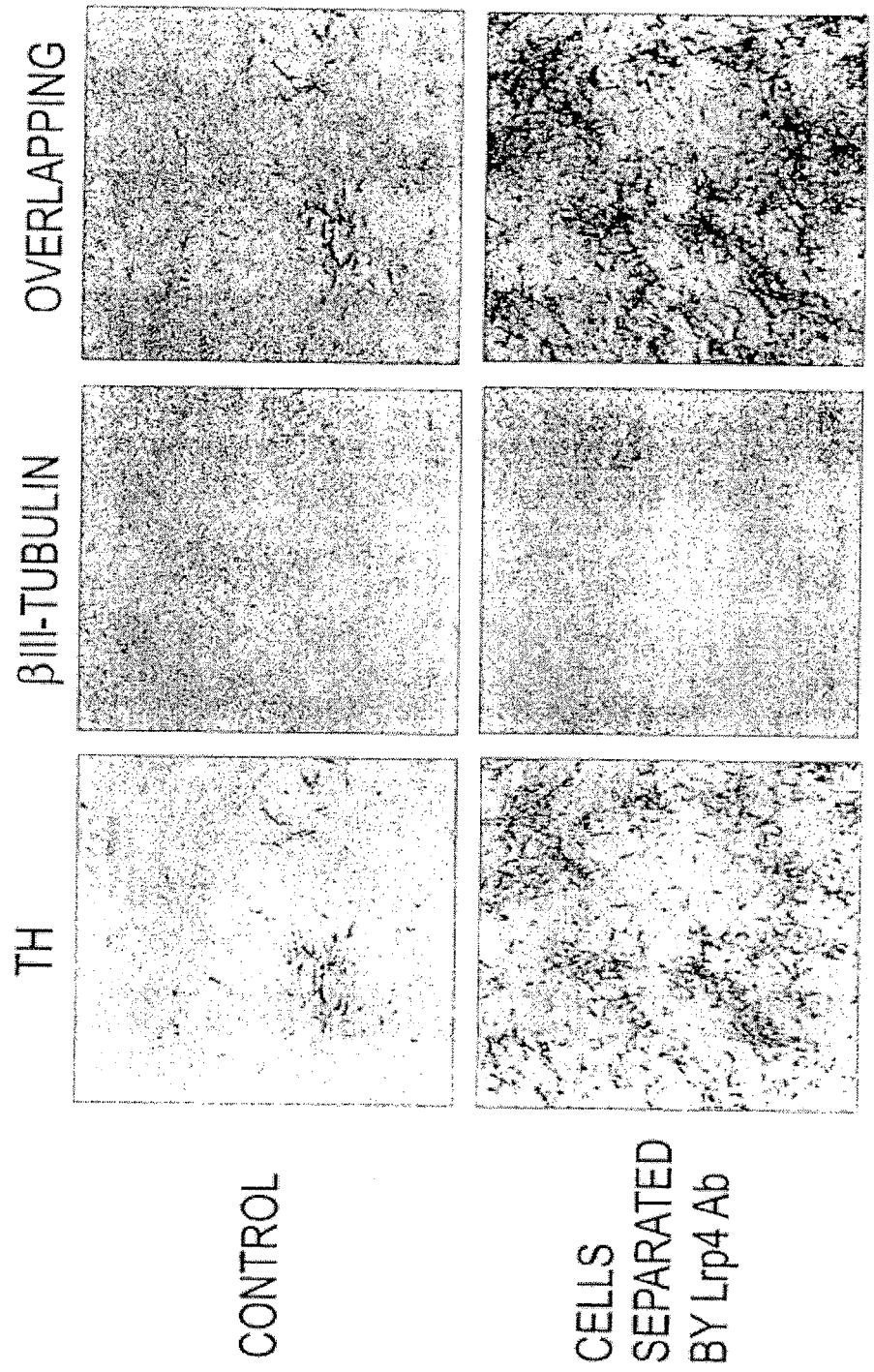
FIG. 14 is a set of photographs showing that Lrp4-positive cells differentiate into dopaminergic neurons.
Figure 15:
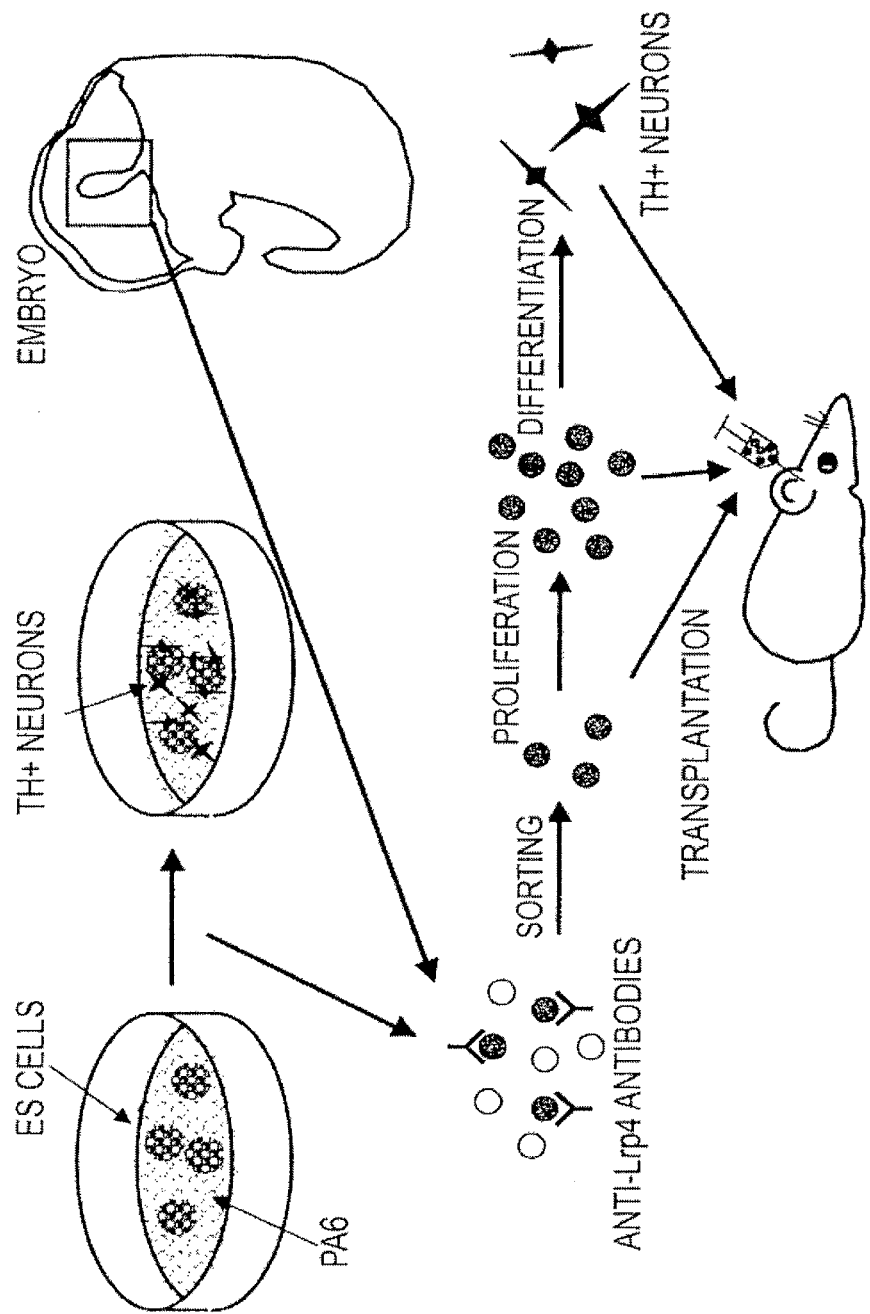
FIG. 15 schematically shows the separation and application of dopaminergic neuron progenitor cells using anti-Lrp4 antibody.

As a result of culturing the separated cells in vitro, it was obvious that more TH protein-positive dopaminergic neurons were induced than with the unseparated control cells. Therefore, it was revealed that the Lrp4-positive cells are certainly dopaminergic neuron lineage progenitor cells and can mature in vitro (FIG. 14).

Example 6 Transplantation of Separated Lrp4-Positive Cells into Striatum in Parkinson's Disease Model Mice Lrp4-expressing cells were separated by flow cytometry using anti-Lrp4 monoclonal antibody, and the cells were transplanted into the striatum of Parkinson's disease model mice.

First, ES cells were induced to differentiate to dopaminergic neuron progenitor cells in vitro using the SDIA method. A cell population comprising the cells was dispersed using a cell dissociation buffer (Invitrogen), and stained with the anti-Lrp4 monoclonal antibody prepared in Example 4 (mixture of FERM BP-10315 and FERM BP-10316 [each ¼-diluted culture supernatant, 1% fetal calf serum, and 1 mM EDTA/SDIA differentiation medium]) at 4° C. for 20 minutes without fixing and permeabilization. Subsequently, the cells were washed three times with 1% fetal calf serum and 1 mM EDTA/SDIA differentiation medium at 4° C. for 3 minutes. The cells were stained with biotin-labeled anti-hamster IgG antibody (Jackson, 10 μg/mL, 1% fetal calf serum and 1 mM EDTA/SDIA differentiation medium) at 4° C. for 20 minutes, and washed as described above. Then, the cells were stained with PE-labeled streptavidin (Pharmingen, 20 μg/mL, 1% fetal calf serum and 1 mM EDTA/SDIA differentiation medium) at 4° C. for 20 minutes, and washed as described above. After staining, the Lrp4-expressing cells were separated by a flow cytometer.

Next, the present inventors transplanted the separated Lrp4 protein-positive cells into the striatum of Parkinson's disease model mice, and characterized the Lrp4 protein-positive cells in the brain.

First, the Parkinson's disease model mice were prepared by injecting 1.25 μL of 6-OHDA (Sigma, 2 μg/μL) into one side of the medial forebrain bundle of 12-week-old mice (slc) to deaden the dopaminergic neurons projecting from the midbrain to the striatum. Two weeks after preparing the model mice, $3 \times 10^4$ Lrp4-positive cells per mouse were transplanted into the striatum to which 6-OHDA had been injected. The Lrp4 protein-positive cells to be transplanted were obtained by: transfecting ES cells to express the EGFP gene under the control of CAG promoter (Niwa et al., Gene 108:193-200 (1991)); inducing the ES cells to differentiate into the dopaminergic neuron progenitor cells in vitro by the SDIA method; and staining the cell population comprising the dopaminergic neuron progenitor cells with the anti-Lrp4 antibody as described in Example 4 and separating by the cell sorter.

Three weeks after the transplantation, 500 μL of 10% urethan in saline was intraperitoneally injected to anesthetize the mice. Under anesthesia, thoracotomy was performed, 30 mL of saline (Otsuka) was injected from left ventricle for perfusion, and then perfusion fixation was carried out with 30 mL of 4% PFA/PBS(−). After fixation, the brains were removed, and further immersion-fixed in 4% PFA/PBS(−) for another eight hours. The brains were then sliced at a thickness of 2 mm, the solution was replaced with 20 to 40% sucrose/PBS(−) overnight, and the brains were embedded in OCT. 10 to 12 μm-thick sections were made, attached on glass slides, dried at room temperature for 30 minutes, and wetted again with PBS(−). Blocking (10% normal donkey serum/Block Ace) was then performed at room temperature for 20 minutes. The sections were then reacted with anti-GFP antibody (Molecular probes, 20 μg/mL, 10% normal donkey serum, and 10% Block Ace/PBS), anti-MAP2 antibody (Sigma, mouse ascites, diluted 100 times, 10% normal donkey serum, and 10% Block Ace/PBS), or anti-TH antibody (Chemicon, 1 μg/mL, 10% normal donkey serum and 10% Block Ace/PBS) at room temperature for one hour, and again at 4° C. overnight. Sections were washed four times with 0.1% Triton X-100/PBS(−) at room temperature for 10 minutes. The sections were then reacted with Alexa Flour 488-labeled anti-rabbit IgG antibody (Molecular Probes, 4 μg/mL, 10% normal donkey serum, and 10% Block Ace/PBS), Cy3-labeled anti-mouse IgG antibody (Jackson, 10 μg/mL, 10% normal donkey serum, and 10% Block Ace/PBS), or Cy5-labeled anti-sheep IgG antibody (Jackson, 10 μg/mL, 10% normal donkey serum, and 10% Block Ace/PBS) at room temperature for one hour. Then, the sections were washed as described above, washed with PBS(−) at room temperature for 10 minutes, and sealed.

The expression of various markers was analyzed by immunohistological staining.

As a result, EGFP-positive cells were observed in the striatum of the transplanted mice (Table 1). This suggests that the transplanted Lrp4 protein-positive cells are successfully engrafted in the striatum of the Parkinson's disease model mice.

Figure 16:
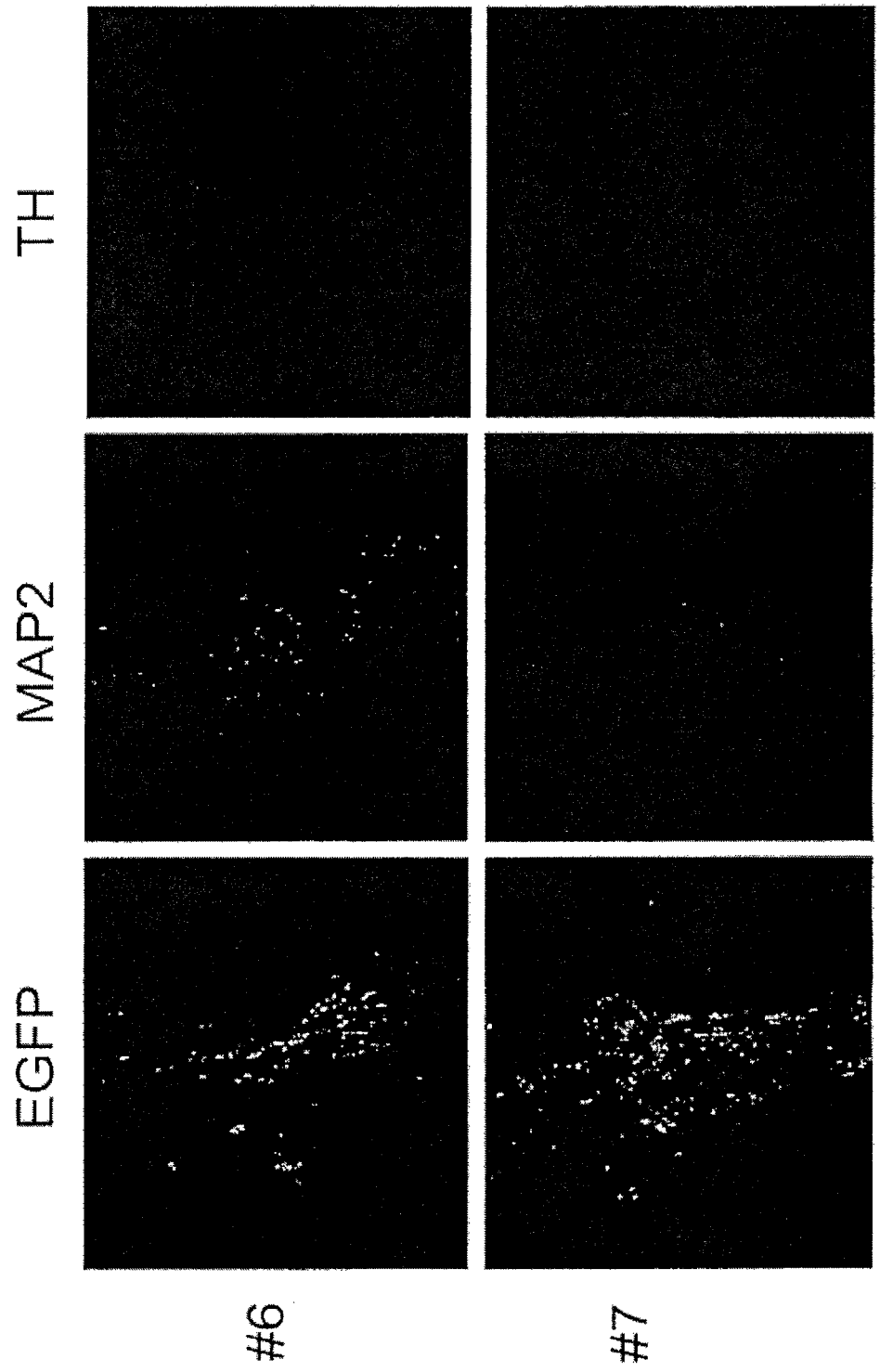
FIG. 16 is a set of photographs showing the in vivo differentiation of transplanted Lrp4-positive cells.

Most of the successfully engrafted cells were also observed to be positive for the mature neuron marker MAP2, and EGFP-positive axons were observed to extend far into the striatum (Table 1 and FIG. 16).

TABLE 1

|  | EGFP+ CELLS | TH+ CELLS | TH+ |
|---|---|---|---|
| #6 SEQ ID NO: 20 | 95 | 19 | 20% |
| #7 SEQ ID NO: 12 | 131 | 21 | 16% |

(Table 1 shows the in vivo differentiation of the transplanted Lrp4-positive cells into TH-positive cells. Two weeks after deadening the dopaminergic neurons with 6-OHDA, the Lrp4 protein-positive cells were transplanted into mice #6 and #7. Perfusion was performed three weeks after transplant.

The results indicated that the transplanted Lrp4 protein-positive cells are nerve progenitor cells, whereas most successfully engrafted cells differentiate and mature into mature nerve cells. About 20% of the successfully engrafted cells were TH-positive, strongly suggesting that at least a part of the transplanted Lrp4 protein-positive cells differentiate into dopaminergic neurons.

Therefore, the dopaminergic neuron progenitor cells separated according to the present invention are able to differentiate into the dopaminergic neurons by being transplanted into the brain, and thus the dopaminergic neuron progenitor cells separated according to the present invention are believed useful for therapies.

Example 7 Lrp4 Expression in Dopaminergic Neurons Induced to Differentiate from ES Cells Using the 5-Stage Method The present inventors examined whether or not Lrp4 is expressed when ES cells are induced to differentiate into the dopaminergic neurons in vitro using the 5-stage method.

First, ES cells (CCE) were induced to differentiate into dopaminergic neurons using the 5-stage method (Lee et al., Nat. Biotech., 18:675-679 (2000), mouse dopaminergic neuron differentiation kit [R&D Systems]). Cells were collected on day 2 at Stage 1, day 4 at Stage 2, day 6 at Stage 3, days 4 and 6 at Stage 4, and days 4 and 7 at Stage 5. Total RNAs were prepared using RNeasy mini kit (Qiagen) to perform RT-PCR. In the RT-PCR, cDNA was first synthesized from 1 μg of the total RNA using RNA PCR kit (TaKaRa). The PCR was performed by the following reaction system, using cDNAs corresponding to 10 ng, 1 ng, and 0.1 ng as templates.

| | |
|---|---|
| 10x ExTaq | 2 µL |
| 2.5 mM dNTP | 1.6 µl |
| ExTaq | 0.1 µL |
| 100 µM primers | 0.2 µL each |
| cDNA | 1 µL |
| Distilled water | 14.9 µL |

PCR was carried out under conditions of 94° C. for 2 minutes, 32 cycles of 94° C. for 30 seconds, 65° C. for 30 seconds, and 72° C. for 2 minutes, and finally 72° C. for 2 minutes.

The sequences of the primers used are shown below.

```
Lrp4:
                                    (SEQ ID NO: 15)
TAGTCTACCACTGCTCGACTGTAACG/

(SEQ ID NO: 16)
CAGAGTGAACCCAGTGGACATATCTG

TH:
                                    (SEQ ID NO: 17)
GTTCCCAAGGAAAGTGTCAGAGTTGG/

(SEQ ID NO: 18)
GAAGCTGGAAAGCCTCCAGGTGTTCC
```

Figure 17:
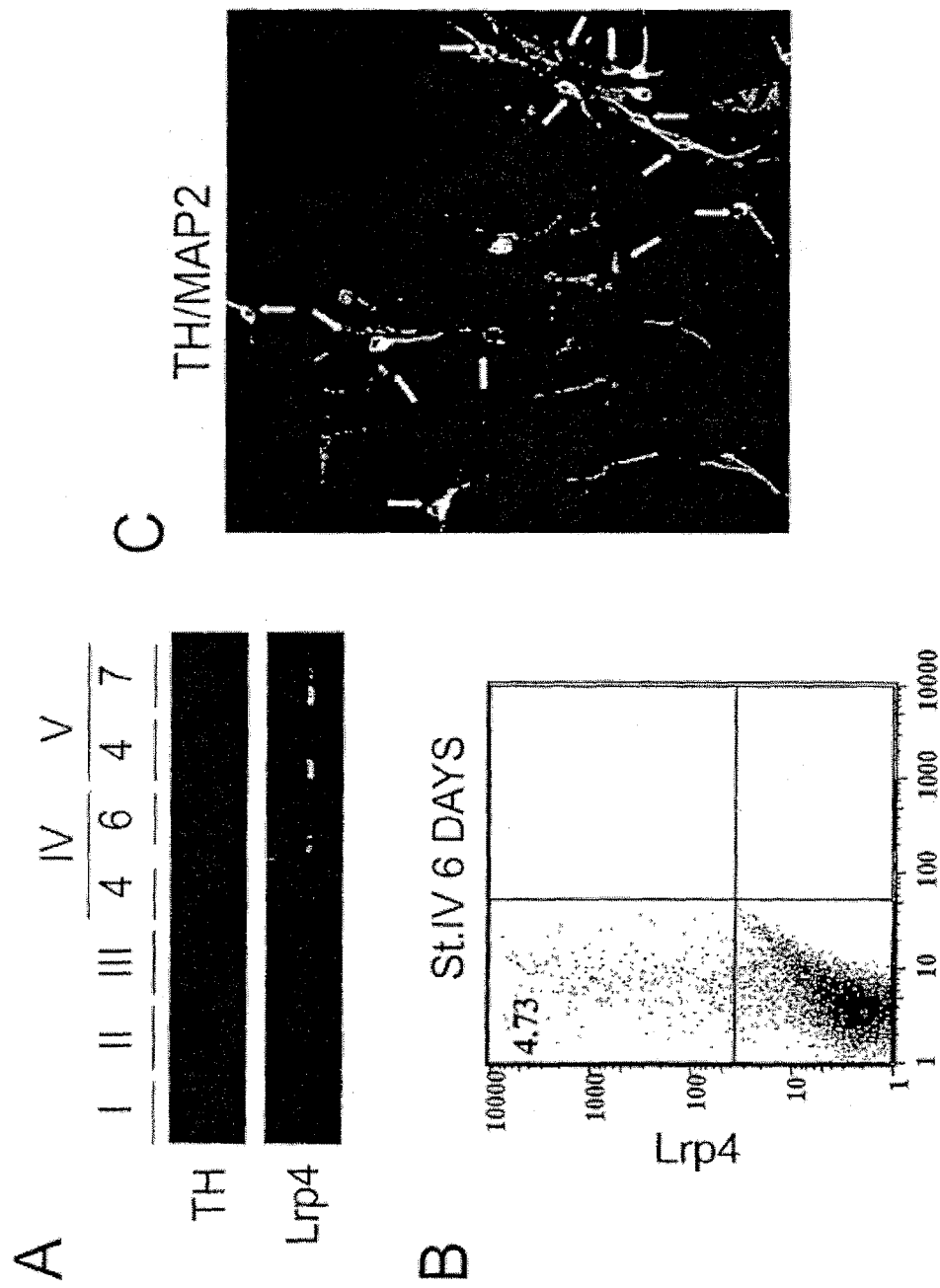
FIG. 17 shows a diagram and photographs indicating Lrp4 expression in cells differentiated by the 5-stage method, and differentiation of Lrp4-positive cells into dopaminergic neurons. The arrows in panel C indicate TH protein-positive dopaminergic neurons.

The results of expression analysis by RT-PCR revealed that Lrp4 is not expressed in Stage 1, at which the cells are undifferentiated ES cells, but is induced to be expressed in Stage 4, at which the dopaminergic neuron progenitor cells are developed (FIG. 17A).

Next, the present inventors detected the Lrp4-expressing cells by flow cytometry using the anti-Lrp4 monoclonal antibody when ES cells were induced to differentiate into the dopaminergic neurons in vitro using the 5-stage method.

First, the cell population (day 7 at Stage 4) comprising the dopaminergic neuron progenitor cells induced to differentiate from ES cells in vitro using the 5-stage method was dispersed using the cell dispersing solution Accumax (Innovative Cell Technologies, Inc.). Without the steps of fixing and permeabilization, the cells were stained with anti-Lrp4 monoclonal antibody (mixture of FERM BP-10315 and FERM BP-10316 [each ½-diluted culture supernatant]) at 4° C. for 20 minutes. The cells were then washed three times with 1% fetal calf serum, 1 mM EGTA, 4.5 mg/mL glucose, and 40 ng/mL DNase I/Ca- and Mg-free Hanks' balanced salt solution (HBSS-) at 4° C. for 3 minutes. The cells were stained with the PE-labeled anti-hamster IgG antibody (8 µg/mL [BD Biosciences], 1% fetal calf serum, 1 mM EGTA, 4.5 mg/mL glucose, and 40 ng/mL DNase I/Ca- and Mg-free Hanks' balanced salt solution (HBSS-)) at 4° C. for 30 minutes, and washed as described above. After staining, Lrp4-expressing cells were detected using a flow cytometer.

The results of detecting Lrp4-expressing cells by flow cytometry using anti-Lrp4 monoclonal antibody detected an Lrp4 protein-expressing population in the cell group comprising the dopaminergic neuron progenitor cells induced to differentiate from the ES cells in vitro using the 5-stage method (FIG. 17B). This suggested that Lrp4 is expressed in the dopaminergic neuron progenitor cells induced to differentiate from the ES cells by not only the SDIA method but also by the 5-stage method, and is useful as a marker for cell separation.

Example 8 Differentiation and Maturation In Vitro of Lrp4-Expressing Cells Separated by Antibodies The present inventors examined whether or not Lrp4 protein-positive cells separated using anti-Lrp4 antibody differentiate into dopaminergic neurons in vitro.

The cell population comprising the dopaminergic neuron progenitor cells induced to differentiate from ES cells in vitro using the 5-stage method was stained using anti-Lrp4 antibody by the method described in Example 4. The Lrp4-positive cells were then separated using a cell sorter. The separated cells were seeded on a glass slide coated with poly-L-ornithine (Sigma, 0.002% in PBS) and fibronectin (Sigma, 5 µg/mL in PBS), and incubated in N2 (Invitrogen, 1×), ascorbic acid (Sigma, 200 µM), and BDNF (R&D Systems, 20 ng/mL)/DMEM/F12 at 37° C. for 7 days. The cultured cells were fixed in 2% PFA and 0.15% picric acid/PBS at 4° C. for 20 minutes, and washed twice with PBS at 4° C. for 10 minutes. Permeabilization with 0.3% Triton X-100/PBS was performed at room temperature for 30 minutes, and blocking with 10% normal donkey serum and 10% normal goat serum/Block Ace was performed at room temperature for 20 minutes. Then, the cells were reacted with anti-TH antibody (Chemicon, 0.4 µg/mL, 10% normal donkey serum, 10% normal goat serum, 2.5% Block Ace, 0.1% Triton X-100/PBS) or anti-MAP2 antibody (Sigma, 1/200 ascites, 0.5 µg/mL, 10% normal donkey serum, 10% normal goat serum, 2.5% Block Ace, and 0.1% Triton X-100/PBS) at room temperature for one hour, and subsequently at 4° C. overnight. On the next day, the cells were washed four times with 0.1% Triton X-100/PBS at room temperature for 10 minutes, and reacted with the FITC-labeled anti-mouse IgG antibody or the Cy3-labeled anti-rabbit IgG antibody (both from Jackson, 10 µg/mL, 10% normal donkey serum, 10% normal goat serum, 2.5% Block Ace, and 0.1% Triton X-100/PBS) at room temperature for 30 minutes. Subsequently, the cells were washed as described above, then washed with PBS at room temperature for 5 minutes, and sealed for observation.

Culturing the separated Lrp4-positive cells in vitro induced many TH protein-positive dopaminergic neurons (FIG. 17C). Therefore, it was revealed that Lrp4-positive cells induced by the 5-stage method are dopaminergic neuron progenitor cells, and can mature in vitro. The Lrp4 was expressed in the dopaminergic neuron progenitor cells induced by two different differentiation methods (SDIA method and 5-stage method), and dopaminergic neuron progenitor cells induced by either method could be separated using the anti-Lrp4 antibody. Accordingly, it appeared that Lrp4 is useful as a marker for dopaminergic neuron progenitor cells derived from any cell source. The 5-stage method is capable of inducing differentiation of dopaminergic neuron progenitor cells without contact with animal-derived cells and components, and expected to be applied clinically. Lrp4 is useful as a cell separation marker in the methods, and thus appeared to be most likely applied to transplant therapy for neurodegenerative diseases including Parkinson's disease.

Example 9 Elimination of Undifferentiated ES Cells by Separating Dopaminergic Neuron Progenitor Cells Using Anti-Lrp4 Antibody When ES cell-derived transplant cells are prepared, it is most important in terms of safety to eliminate the undifferentiated ES cells that result in teratoma. Since Lrp4 is not expressed in undifferentiated ES cells (Example 3), separation using Lrp4 as a marker is expected to eliminate undifferentiated ES cells. To confirm this hypothesis, the present inventors used RT-PCR to examine the expression of ERas (Nature, 423(6939):541-5 (2003)) and Nanog (Cell, 113(5): 631-42 (2003)), which are ES cell-specific genes, to investigate whether undifferentiated ES cells were contained in cells separated using anti-Lrp4 antibody from cells induced to differentiate from ES cells in vitro using the SDIA method.

First, using the method described in Example 5, Lrp4-positive and -negative cells were separated by a cell sorter from a cell population comprising dopaminergic neuron progenitor cells induced to differentiate from ES cells in vitro using the SDIA method. Total RNA was collected immediately after separation, and the cDNA to be amplified was prepared. PCR was performed using cDNAs corresponding to 4 ng, 0.4 ng, and 0.04 ng as templates for the following reaction system:

| | |
|---|---|
| 10x ExTaq | 1 μL |
| 2.5 mM dNTP | 0.8 μL |
| ExTaq | 0.05 μL |
| 100 μM primers | 0.1 μL each |
| cDNA | 1 μL |
| Distilled water | 6.95 μL |

PCR was carried out under conditions of 94° C. for 2 minutes, 26 cycles (for Lrp4 and Nestin) or 30 cycles (for ERas and Nanog) of 94° C. for 30 seconds, 65° C. for 30 seconds, and 72° C. for 2 minutes, and finally 72° C. for 2 minutes.

The sequences of the primers used are shown below (the sequences of Lrp4 and Nestin were described in Example 5).

```
ERas:
                                    (SEQ ID NO: 27)
TGCTCTCACCATCCAGATGACTCACC/

(SEQ ID NO: 28)
TGGACCATATCTGCTGCAACTGGTCC

Nanog:
                                    (SEQ ID NO: 29)
TCCAGCAGATGCAAGAACTCTCCTCC/

(SEQ ID NO: 30)
TTATGGAGCGGAGCAGCATTCCAAGG
```

Figure 18:
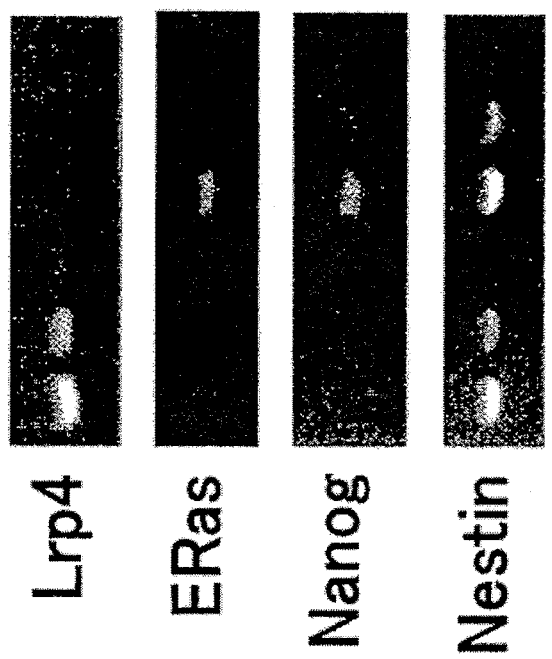
FIG. 18 is a set of photographs showing the results of using RT-PCR to analyze the expression of ES cell-specific genes (ERas and Nanog) in Lrp4-positive cells and Lrp4-negative cells.

As a result, ERas and Nanog, which are expressed specifically in ES cells, were not expressed in the Lrp4-positive cell population; on the other hand, ERas and Nanog expressions were detected in the Lrp4-negative cell population (FIG. 18). Accordingly, it was revealed that undifferentiated ES cells contained in the cells induced to differentiate by the SDIA method could be eliminated by cell separation using Lrp4.

INDUSTRIAL APPLICABILITY

The present invention identified Lrp4 as a gene expressed specifically and transiently in dopaminergic neuron proliferative progenitor cells. As a result of examining Lrp4 expression in more detail, it was confirmed that Lrp4 mRNA and the Lrp4 protein were expressed specifically in dopaminergic neuron proliferative progenitor cells and in dopaminergic neuron progenitor cells, including cells prior to and after cell cycle exit, respectively. Thus, by using the expression of Lrp4 mRNA or an Lrp4 polypeptide in the cells as an index, it became possible in terms of safety, survival rate, and network formation to select dopaminergic neuron lineage cells suitable for transplant therapy for neurodegenerative diseases including Parkinson's disease. When the cells are obtained using Lrp4 as a marker, as in the present invention, the cells can be easily differentiated into a suitable state in vitro even when the therapy requires mature cells. Moreover, dopaminergic neuron progenitor cells obtained by the methods of the present invention can also be used to isolate genes specifically expressed in these cells. The cells are also thought to be useful in developing pharmaceuticals for neurodegenerative diseases such as Parkinson's disease. Since dopaminergic neuron proliferative progenitor cells obtained using Lrp4 mRNA as a marker are involved in early neuron formation, they are useful in elucidating the neuron maturation process, namely, for identifying various factors involved in the maturation process. Elucidation of these factors is expected to contribute greatly to the treatment of neurodegenerative diseases. Moreover, maturation of these cells can be used as an index for screening substances that may regulate (inhibit or promote) the maturation process.

The invention claimed is:

1. A method for detecting or selecting a dopaminergic neuron progenitor cell, wherein the method comprises the step of contacting an antibody with a cell sample thought to comprise a dopaminergic neuron progenitor cell, wherein the antibody binds to a polypeptide selected from the group consisting of:
   (1) a polypeptide encoded by a polynucleotide consisting of the nucleotide sequence of SEQ ID NO:1;
   (2) a polypeptide consisting of the amino acid sequence of SEQ ID NO:3; and
   (3) a polypeptide encoded by a polynucleotide that hybridizes under stringent conditions with a sequence completely complementary to the nucleotide sequence of SEQ ID NO:1, wherein said stringent conditions are hybridization in 2×SSC, 0.1% SDS, at 65° C.

2. A method for producing a dopaminergic neuron proliferative progenitor cell, wherein the method comprises the steps of:
   (1) selecting a dopaminergic neuron progenitor cell by the method of claim 1; and
   (2) removing a postmitotic dopaminergic neuron precursor cell to select the dopaminergic neuron proliferative progenitor cell.

3. The method of claim 1, wherein the cell sample comprises cells from the ventral midbrain.

4. The method of claim 1, wherein the cell sample comprises in vitro differentiated dopaminergic neuron progenitor cells.

5. The method of claim 4, wherein the in vitro differentiated dopaminergic neuron progenitor cells are differentiated from embryonic stem cells.

6. The method of claim 4, wherein the in vitro differentiated dopaminergic neuron progenitor cells are differentiated from bone marrow interstitial cells.

7. The method of claim 1, wherein the method further comprises isolating cells bound by the antibody from the cell sample.

8. The method of claim 3, wherein the method further comprises isolating cells bound by the antibody from the cell sample.

9. The method of claim 4, wherein the method further comprises isolating cells bound by the antibody from the cell sample.

* * * * *

SEQUENCE LISTING

```
<160> NUMBER OF SEQ ID NOS: 30

<210> SEQ ID NO 1
<211> LENGTH: 4864
<212> TYPE: DNA
<213> ORGANISM: Mus musculus

<400> SEQUENCE: 1
ctagtcccca ggcagacggt ccctcactcc tgtggcttgg cgtcggagac gctggcagtc      60
atgggcaggg tttccttcag cgttcgggtc agctccgtgc ggagagcccg ctgctcttgt     120
cctgggcgat gctacctctc ctgcagagtc cctccaacca ccgccctccg tgcactgaac     180
ggtcttggct gcgcgggggt tccgggggag actgcaggtg gagccgtcgg acccggcccc     240
ttggggaccc gtggcttcct ctccgggtcc aagttccagg ctcccggcag ctggaaggat     300
tgctttggag ccccgcctgc tccagacgtc ttgagagcag acaggagcgt gggcgagggc     360
tgtcctcaga agctggtgac tgctaacttg ctgcgcttcc tcctgctggt gctcatcccc     420
tgcatctgcg ccctcatcgt gctgctgcc atcctgctgt cctttgtggg aacattaaaa     480
agggtttatt tcaaatcaaa tgacagtgaa cctttggtca ctgatgggga agctcgagtg     540
```

```
cctggtgtta ttcctgtaaa tacagtttat tatgagaaca cagggggcgcc ctctctgccc      600 cccagccagt ccactccagc ctggacaccg agagctcctt ctccagagga ccagagtcac      660
aggaacacaa gcacctgcat gaacatcact cacagccagt gtcaaattct gccctaccac      720
agcacgttgg cacctctctt gccaattgtc aaaaacatgg acatggagaa gttcctcaag      780
ttcttcacgt acctccatcg cctcagttgc tatcaacata tcctgctctt cggctgtagc      840
ctcgccttcc ctgagtgcgt tgttgatggc gatgacaggc atggtcttct accctgtaga      900
tctttctgtg aggctgcaaa agaaggatgc gaatctgtcc tgggaatggt gaactcctcc      960
tggccggatt ccctcagatg ctctcagttt agggaccaca ctgagactaa cagcagtgtc     1020
agaaagagct gcttctcact gcagcaggaa catggaaagc aatcactctg tggagggggc     1080
gagagcttcc tgtgtaccag cgggctctgc gtccccaaga agctgcagtg taacggctat     1140
aatgactgtg atgactggag cgacgaggcg cattgcaact gcagcaagga tctgtttcac     1200
tgtggcacag gcaagtgcct ccactacagc ctcttgtgtg atgggtacga tgactgtggg     1260
gacccgagtg acgagcaaaa ctgtgattgt aatctcacaa aagagcatcg ctgtggagat     1320
gggcgctgca ttgcggctga gtgggtgtgc gatgggggacc atgactgtgt ggacaagtct     1380
gatgaggtca actgctcttg tcacagccag ggcctggtgg aatgcacaag tggacagtgc     1440
atccctagca ccttccagtg tgatgggggac aagactgta aggatgggag tgacgaggag     1500
aactgcagtg acagtcagac gccatgtcca aaggagaaac agggatgctt tggcagttcc     1560
tgcgtcgaat cctgtgctgg tagctctctg tgtgactcag acagcagcct gagtaactgc     1620
agtcaatgtg agcccatcac tttggaactc tgcatgaatt tgctctacaa ccatacacat     1680
tatccaaatt accttggcca cagaactcaa aaggaagcgt ccatcagctg ggagtcatcc     1740
cttttccctg cccttgtaca aaccaactgt tacaaatacc tcatgttttt cgcttgcacc     1800
attttggttc caaagtgtga tgtgaataca ggacaacgca tcccgccttg cagactcctg     1860
tgtgagcact ccaaagagcg ctgtgagtct gttctgggaa tcgttggcct gcagtggcct     1920
gaagacaccg actgcaatca atttccagag gaaagttcag acaatcaaac ttgcctcctg     1980
cccaatgaag atgtggaaga tgctctccg agtcacttca aatgccgctc gggacgatgc     2040
gttctgggct ccaggagatg tgacggccag gctgactgtg acgacgacag tgacgaggag     2100
aactgtggtt gtaaagagag agctctttgg gaatgtccat ttaataagca atgtctgaag     2160
catacattaa tctgcgatgg gtttccagat tgtccagaca gtatggatga aaaaaactgc     2220 tcatttttgcc aagacaatga gctggaatgt gccaaccatg agtgtgtgcc gcgtgacctt     2280
tggtgcgacg gatgggtcga ctgctcagac agttctgatg aatgggggctg tgtgaccctc     2340 tctaaaaatg ggaactcctc ctcattgctg actgttcaca aatctgcaaa ggaacaccac     2400
gtgtgtgctg acggctggcg ggagacgttg agtcagctgg cctgcaagca gatgggttta     2460
ggagaaccgt ctgtgaccaa gctgatccca ggacaggaag ccagcagtg gctgaggttg     2520 taccccaact gggagaatct caatgggagc accttgcagg agctgctggt atacaggcac     2580
tcctgcccaa gcagaagtga gatttcccctt ctgtgctcca gcaagactg tggccgccgc     2640 cctgctgccc gaatgaacaa gaggatcctt ggggtcgga ctagtcgtcc tgggaggtgg     2700
ccgtggcagt gctctctgca gagtgaaccc agtggacata tctgtggctg tgtcctcatt     2760
gccaagaagt gggtcctgac agttgcccat gctttgaag ggagagaaga cgctgatgtt     2820
tggaaagtgg tatttggcat aaacaacctg gaccatccat caggcttcat gcagacccgc     2880
```

-continued

```
tttgtgaaga ccatcctgct acatccccgt tacagtcgag cagtggtaga ctatgatatc    2940
agcgtggtgg agctgagcga tgatatcaat gagacaagct acgtcagacc tgtctgccta    3000
cccagtccgg aggagtatct agaaccagat acgtactgct acatcacagg ctggggccac    3060
atgggcaata aaatgccctt taagctgcag gagggagagg tccgcattat ccctctggag    3120
cagtgccagt cctatttga catgaagacc atcaccaatc ggatgatctg tgctggctat    3180
gagtctggca ccgtggactc ctgcatggga gacagcggtg ggcctctggt ttgtgaacga    3240
cccggaggac agtggacatt atttggttta acttcatggg gctccgtctg ctttccaaa    3300 gttctgggac ctggagtgta cagcaatgtg tcttactttg tgggctggat tgaaagacaa    3360
atatatatcc agaccttct ccaaaagaaa tcccaaggat aatcagagac tttgtgggga    3420
aacctacatg gagaatgacc ctctgaaaca gaagcttgtc ctgccaagag ctgtacgaac    3480
aggcgtttca cggacaggac gctcaacatg caccgcaaga tctctcctgt ttgtgctaga    3540
tgagttttac tcaggcttta atctctttca acattatcat ttattaattt catgaatcct    3600
tttaaaagca cagagcaaag taggttttgt tatttttgcta ggctaacctt gaatgtagtg    3660
tgcaattacc aacccataga gacatttgga gctctagggt aacaagttat agaaagctcc    3720
ttttattact actacaagac acacacggag atacacgctg actgatctcc agtttctgct    3780
taagcccagt ggcttagggg gcacatttca gaactgatct tggagactgg cttttaattt    3840
gtagaaagcc aagagaatat atatgctttt attatttact ctactcttct aaataacttg    3900
aagaaatcat gaaagacaga gaaaggaccc acagtgttga tctagacagt tgaagttgca    3960
agaatgtaaa attctctagc caaccaaact aacactctga agtaagtaga attctatcct    4020
ttctgtattc aaattaagct taaaatctcc accagatttg ttcccgttac tgggaatttt    4080
cggagtatgt cacttagatg actgtgatgt caaaagccag gtcaatcctt gaggaaataa    4140
tttgtttgct tatgtgggaa tgaataagaa tctttccatt ccgcaaaaca cacaaattaa    4200
aaaggagaaa aaaattaaa taacattcca cacccaatta attctgaaaa ttagtctgct    4260
tgtattcacc caaaacagaa aagttacaga aatatatttc aaagtgcagc aaaatgttgc    4320
atggagtata taacattttg caatttcccc ctcatgatgt ctaacatccg gtattgccat    4380
ttgcctcatt gataattaaa actaaatttt aaggatgctt ttaagcactg gccactttta    4440
tgggaatcaa ttcccaaagc aattagtggt tacaagtatt ttttcccact aaaaagtttc    4500
aaaacacaaa ccttcatact aaattaatta gccagacatg aactatgtaa catgcaaatg    4560 ccttttgaa caagtaggat gcactgttaa acttcaccag caaccaaact gcctcagtat    4620
tgcttacagg gactacctgc aatttatat gtgtatttg tactcttttt ctagatagtt    4680
caaatgcaaa acattgtttc aacccctatt ctccatgttg ttcacctctt gtcctggaat    4740
ttgttacaaa gtgtgtgtag caaatgattg tactgcggtc aggactatat gaaggtttag    4800
gaccatcggg tcggttttgt tataattgtt ggcacataat taataaaata ttttagcat    4860 tggg                                                                 4864
```

<210> SEQ ID NO 2
<211> LENGTH: 5810
<212> TYPE: DNA
<213> ORGANISM: Homo sapiens

<400> SEQUENCE: 2

```
cgggcccagg cgcggtggcg gtggccgggg ctgcggcgcg gggggcgggg cggtcgggcc      60
cgggacaccc cctcccggtc ccctggcggg gcagcgtcgg ctctggcagc actggaggcg    120
```

```
gcggcggccc gagggcgact tgcggggcgc gcaggccgcc gtgcacccgg gacgcttccc    180
cctcggggac cctccgcggg cttctccgcc gcgccgtccg gcgggagccg gcgggacccc    240
gggcgagcgg cgcgggcggc accatgaggc ggcagtgggg cgcgctgctg cttggcgccc    300
tgctctgcgc acacgtacta cctacctgtt cccctcttga ctttcactgt gacaatggca    360
agtgcatccg ccgctcctgg gtgtgtgacg gggacaacga ctgtgaggat gactcggatg    420
agcaggactg tccccccccgg gagtgtgagg aggacgagtt ccctgccag aatggctact    480 gcatccggag tctgtggcac tgcgatggtg acaatgactg tggcgacaac agcgatgagc    540
agtgtgacat gcgcaagtgc tccgacaagg agttccgctg tagtgacgga agctgcattg    600
ctgagcattg gtactgcgac ggtgacaccg actgcaaaga tggctccgat gaggagaact    660
gtccctcagc agtgccagcg cccccctgca acctggagga gttccagtgt gcctatggac    720
gctgcatcct cgacatctac cactgcgatg gcgacgatga ctgtggagac tggtcagacg    780
agtctgactg ctgtgagtac tctggccagc tgggagcctc ccaccagccc tgccgctctg    840
gggagttcat gtgtgacagt ggcctgtgca tcaatgcagg ctggcgctgc gatggtgacg    900
cggactgtga tgaccagtct gatgagcgca actgcaaaca gttccgctgt cactcaggcc    960
gctgtgtccg cctgtcctgg cgctgtgatg gggaggacga ctgtgcagac aacagcgatg    1020
aagagaactg tgagaataca ggaagccccc aatgtgcctt ggaccagttc ctgtgttgga    1080
atgggcgctg cattgggcag aggaagctgt gcaacggggt caacgactgt ggtgacaaca    1140
gcgacgaaag cccacagcag aattgccggc cccggacggg tgaggagaac tgcaatgtta    1200
acaacggtgg ctgtgcccag aagtgccaga tggtgcgggg ggcagtgcag tgtacctgcc    1260
acacaggcta ccggctcaca gaggatgggc acacgtgcca agatgtgaat gaatgtgccg    1320
aggaggggta ttgcagccag ggctgcacca acagcgaagg ggctttccaa tgctggtgtg    1380
aaacaggcta tgaactacgg cccgaccggc gcagctgcaa ggctctgggg ccagagcctg    1440
tgctgctgtt cgccaatcgc atcgacatcc ggcaggtgct gccacaccgc tctgagtaca    1500
cactgctgct taacaacctg gagaatgcca ttgcccttga tttccaccac cgccgcgagc    1560
ttgtcttctg gtcagatgtc accctggacc ggatcctccg tgccaacctc aacgcagca    1620 acgtggagga ggttgtgtct actgggctgg agagcccagg gggcctggct gtggattggg    1680
tccatgacaa actctactgg accgactcag gcacctcgag gattgaggtg gccaatctgg    1740
atggggccca ccggaaagtg ttgctgtggc agaacctgga gaagccccgg gccattgcct    1800
tgcatcccat ggagggtacc atttactgga cagactgggg caacacccccc cgtattgagg    1860 cctccagcat ggatggctct ggacgccgca tcattgccga tacccatctc ttctggccca    1920
atggcctcac catcgactat gccgggcgcc gtatgtactg ggtggatgct aagcaccatg    1980
tcatcgagag ggccaatctg gatgggagtc accgtaaggc tgtcattagc caggtgtttg    2040
aagacagcct gtactggaca gactggcaca ccaagagcat caatagcgct aacaaattta    2100
cggggaagaa ccaggaaatc attcgcaaca aactccactt ccctatggac atccacacct    2160
tgcaccccca gcgccaacct gcagggaaaa accgctgtgg ggacaacaac ggaggctgca    2220
cgcacctgtg tctgcccagt ggccagaact acacctgtgc ctgccccact ggcttccgca    2280
agatcagcag ccacgcctgt gcccagagtc ttgacaagtt cctgctttt gcccgaagga    2340 tggacatcct tcgaatcagc tttgacacag aggacctgtc tgatgatgtc atcccactgg    2400
ctgacgtgcg cagtgctgtg gcccttgact gggactcccg ggatgaccac gtgtactgga    2460
```

```
cagatgtcag cactgatacc atcagcaggg ccaagtggga tggaacagga caggaggtgg    2520
tagtggatac cagtttggag agcccagctg gcctggccat tgattgggtc accaacaaac    2580
tgtactggac agatgcaggt acagaccgga ttgaagtagc aacacagat ggcagcatga     2640 gaacagtact catctgggag aaccttgatc gtcctcggga catcgtggtg aacccatgg     2700 gcgggtacat gtattggact gactggggtg cgagcccaa gattgaacga gctggcatgg    2760
atgcctcagg ccgccaagtc attatctctt ctaatctgac ctggcctaat gggttagcta    2820
ttgattatgg gtcccagcgt ctatactggg ctgacgccgg catgaagaca attgaatttg    2880
ctggactgga tggcagtaag aggaaggtgc tgattggaag ccagctcccc cacccatttg    2940
ggctgaccct ctatggagag cgcatctatt ggactgactg gcagaccaag agcatacaga    3000
gcgctgaccg gctgacaggg ctggaccggg agactctgca ggagaacctg gaaaacctaa    3060
tggacatcca tgtcttccac cgccgccggc ccccagtgtc tacaccatgt gctatggaga    3120
atggcggctg tagccacctg tgtcttaggt ccccaaatcc aagcggattc agctgtacct    3180
gccccacagg catcaacctg ctgtctgatg gcaagacctg ctcaccaggc atgaacagtt    3240
tcctcatctt cgccaggagg atagacattc gcatggtctc cctggacatc ccttatttg     3300 ctgatgtggt ggtaccaatc aacattacca tgaagaacac cattgccatt ggagtagacc    3360
cccaggaagg aaaggtgtac tggtctgaca gcacactgca caggatcagt cgtgccaatc    3420
tggatggctc acagcatgag gacatcatca ccacagggct acagaccaca gatgggctcg    3480
cggttgatgc cattggccgg aaagtatact ggacagacac gggaacaaac cggattgaag    3540
tgggcaacct ggacgggtcc atgcggaaag tgttggtgtg cagaaccttg acagtcccc     3600 gggccatcgt actgtaccat gagatggggt ttatgtactg gacagactgg ggggagaatg    3660
ccaagttaga gcggtccgga atggatggct cagaccgcgc ggtgctcatc aacaacaacc    3720
taggatggcc caatggactg actgtggaca aggccagctc ccaactgcta tgggccgatg    3780
cccacaccga gcgaattgag gctgctgacc tgaatggtgc caatcggcat acattggtgt    3840
caccggtgca gcacccatat ggcctcaccc tgctcgactc ctatatctac tggactgact    3900
ggcagactcg gagcatccac cgtgctgaca agggtactgg cagcaatgtc atcctcgtga    3960
ggtccaacct gccaggcctc atggacatgc aggctgtgga ccgggcacag ccactaggtt    4020
ttaacaagtg cggctcgaga aatggcggct gctcccacct ctgcttgcct cggccttctg    4080
gcttctcctg tgcctgcccc actggcatcc agctgaaggg agatgggaag acctgtgatc    4140
cctctcctga gacctacctg ctcttctcca gccgtggctc catccggcgt atctcactgg    4200
acaccagtga ccacaccgat gtgcatgtcc ctgttcctga gctcaacaat gtcatctccc    4260
tggactatga cagcgtggat ggaaaggtct attacacaga tgtgttcctg gatgttatca    4320
ggcgagcaga cctgaacggc agcaacatgg agacagtgat cgggcgaggg ctgaagacca    4380
ctgacgggct ggcagtggac tgggtggcca ggaacctgta ctggacagac acaggtcgaa    4440
ataccattga ggcgtccagg ctggatggtt cctgccgcaa agtactgatc aacaatagcc    4500
tggatgagcc ccgggccatt gctgttttcc ccaggaaggg gtacctcttc tggacagact    4560
ggggccacat tgccaagatc gaacgggcaa acttggatgg ttctgagcgg aaggtcctca    4620
tcaacacaga cctgggttgg cccaatggcc ttaccctgga ctatgatacc cgcaggatct    4680
actgggtgga tgcgcatctg gaccggatcg agagtgctga cctcaatggg aaactgcggc    4740
aggtcttggt cagccatgtg tcccacccct ttgccctcac acagcaagac aggtggatct    4800
actggacaga ctggcagacc aagtcaatcc agcgtgttga caaatactca ggccggaaca    4860
```

-continued

```
aggagacagt gctggcaaat gtggaaggac tcatggatat catcgtggtt tccccctcagc    4920 ggcagacagg gaccaatgcc tgtggtgtga acaatggtgg ctgcacccac ctctgctttg    4980
ccagagcctc ggacttcgta tgtgcctgtc ctgacgaacc tgatagccgg ccctgctccc    5040
ttgtgcctgg cctggtacca ccagctccta gggctactgg catgagtgaa aagagcccag    5100
tgctacccaa cacaccacct accaccttgt attcttcaac cacccggacc cgcacgtctc    5160
tggaggaggt ggaaggaaga tgctctgaaa gggatgccag gctgggcctc tgtgcacgtt    5220
ccaatgacgc tgttcctgct gctccagggg aaggacttca tatcagctac gccattggtg    5280
gactcctcag tattctgctg attttggtgg tgattgcagc tttgatgctg tacagacaca    5340
aaaaatccaa gttcactgat cctggaatgg ggaacctcac ctacagcaac cctcctacc     5400 gaacatccac acaggaagtg aagattgaag caatccccaa accagccatg tacaaccagc    5460
tgtgctataa gaaagaggga gggcctgacc ataactacac caaggagaag atcaagatcg    5520
tagagggaat ctgcctcctg tctggggatg atgctgagtg ggatgacctc aagcaactgc    5580
gaagctcacg gggggcctc ctccgggatc atgtatgcat gaagacagac acggtgtcca    5640
tccaggccag ctctggctcc ctggatgaca cagagacgga gcagctgtta caggaagagc    5700
agtctgagtg tagcagcgtc catactgcag ccactccaga aagacgaggc tctctgccag    5760
acacgggctg gaaacatgaa cgcaagctct cctcagagag ccaggtctaa               5810
```

<210> SEQ ID NO 3
<211> LENGTH: 1113
<212> TYPE: PRT
<213> ORGANISM: Mus musculus

<400> SEQUENCE: 3

```
Met Gly Arg Val Ser Phe Ser Val Arg Val Ser Val Arg Arg Ala
 1               5                  10                  15

Arg Cys Ser Cys Pro Gly Arg Cys Tyr Leu Ser Cys Arg Val Pro Pro
                20                  25                  30

Thr Thr Ala Leu Arg Ala Leu Asn Gly Leu Gly Cys Ala Gly Val Pro
            35                  40                  45

Gly Glu Thr Ala Gly Gly Ala Val Gly Pro Gly Pro Leu Gly Thr Arg
        50                  55                  60

Gly Phe Leu Ser Gly Ser Lys Phe Gln Ala Pro Gly Ser Trp Lys Asp
 65                  70                  75                  80

Cys Phe Gly Ala Pro Ala Pro Asp Val Leu Arg Ala Asp Arg Ser
                85                  90                  95

Val Gly Glu Gly Cys Pro Gln Lys Leu Val Thr Ala Asn Leu Leu Arg
            100                 105                 110

Phe Leu Leu Leu Val Leu Ile Pro Cys Ile Cys Ala Leu Ile Val Leu
            115                 120                 125

Leu Ala Ile Leu Leu Ser Phe Val Gly Thr Leu Lys Arg Val Tyr Phe
        130                 135                 140

Lys Ser Asn Asp Ser Glu Pro Leu Val Thr Asp Gly Glu Ala Arg Val
145                 150                 155                 160

Pro Gly Val Ile Pro Val Asn Thr Val Tyr Tyr Glu Asn Thr Gly Ala
                165                 170                 175

Pro Ser Leu Pro Pro Ser Gln Ser Thr Pro Ala Trp Thr Pro Arg Ala
            180                 185                 190

Pro Ser Pro Glu Asp Gln Ser His Arg Asn Thr Ser Thr Cys Met Asn
        195                 200                 205
```

```
Ile Thr His Ser Gln Cys Gln Ile Leu Pro Tyr His Ser Thr Leu Ala
    210             215                 220

Pro Leu Leu Pro Ile Val Lys Asn Met Asp Met Glu Lys Phe Leu Lys
225             230                 235                 240

Phe Phe Thr Tyr Leu His Arg Leu Ser Cys Tyr Gln His Ile Leu Leu
                245                 250                 255

Phe Gly Cys Ser Leu Ala Phe Pro Glu Cys Val Val Asp Gly Asp Asp
            260                 265                 270

Arg His Gly Leu Leu Pro Cys Arg Ser Phe Cys Glu Ala Ala Lys Glu
        275                 280                 285

Gly Cys Glu Ser Val Leu Gly Met Val Asn Ser Ser Trp Pro Asp Ser
    290                 295                 300

Leu Arg Cys Ser Gln Phe Arg Asp His Thr Glu Thr Asn Ser Ser Val
305                 310                 315                 320

Arg Lys Ser Cys Phe Ser Leu Gln Gln Glu His Gly Lys Gln Ser Leu
                325                 330                 335

Cys Gly Gly Gly Glu Ser Phe Leu Cys Thr Ser Gly Leu Cys Val Pro
            340                 345                 350

Lys Lys Leu Gln Cys Asn Gly Tyr Asn Asp Cys Asp Asp Trp Ser Asp
        355                 360                 365

Glu Ala His Cys Asn Cys Ser Lys Asp Leu Phe His Cys Gly Thr Gly
    370                 375                 380

Lys Cys Leu His Tyr Ser Leu Leu Cys Asp Gly Tyr Asp Asp Cys Gly
385                 390                 395                 400

Asp Pro Ser Asp Glu Gln Asn Cys Asp Cys Asn Leu Thr Lys Glu His
                405                 410                 415

Arg Cys Gly Asp Gly Arg Cys Ile Ala Ala Glu Trp Val Cys Asp Gly
            420                 425                 430

Asp His Asp Cys Val Asp Lys Ser Asp Glu Val Asn Cys Ser Cys His
        435                 440                 445

Ser Gln Gly Leu Val Glu Cys Thr Ser Gly Gln Cys Ile Pro Ser Thr
    450                 455                 460

Phe Gln Cys Asp Gly Asp Glu Asp Cys Lys Asp Gly Ser Asp Glu Glu
465                 470                 475                 480

Asn Cys Ser Asp Ser Gln Thr Pro Cys Pro Glu Gly Glu Gln Gly Cys
                485                 490                 495

Phe Gly Ser Ser Cys Val Glu Ser Cys Ala Gly Ser Ser Leu Cys Asp
            500                 505                 510

Ser Asp Ser Ser Leu Ser Asn Cys Ser Gln Cys Glu Pro Ile Thr Leu
        515                 520                 525

Glu Leu Cys Met Asn Leu Leu Tyr Asn His Thr His Tyr Pro Asn Tyr
    530                 535                 540

Leu Gly His Arg Thr Gln Lys Glu Ala Ser Ile Ser Trp Glu Ser Ser
545                 550                 555                 560

Leu Phe Pro Ala Leu Val Gln Thr Asn Cys Tyr Lys Tyr Leu Met Phe
                565                 570                 575

Phe Ala Cys Thr Ile Leu Val Pro Lys Cys Asp Val Asn Thr Gly Gln
            580                 585                 590

Arg Ile Pro Pro Cys Arg Leu Leu Cys Glu His Ser Lys Glu Arg Cys
        595                 600                 605

Glu Ser Val Leu Gly Ile Val Gly Leu Gln Trp Pro Glu Asp Thr Asp
    610                 615                 620
```

-continued

Cys Asn Gln Phe Pro Glu Ser Ser Asp Asn Gln Thr Cys Leu Leu
625                 630                 635                 640

Pro Asn Glu Asp Val Glu Glu Cys Ser Pro Ser His Phe Lys Cys Arg
            645                 650                 655

Ser Gly Arg Cys Val Leu Gly Ser Arg Arg Cys Asp Gly Gln Ala Asp
            660                 665                 670

Cys Asp Asp Asp Ser Asp Glu Glu Asn Cys Gly Cys Lys Glu Arg Ala
675                 680                 685

Leu Trp Glu Cys Pro Phe Asn Lys Gln Cys Leu Lys His Thr Leu Ile
690                 695                 700

Cys Asp Gly Phe Pro Asp Cys Pro Asp Ser Met Asp Glu Lys Asn Cys
705                 710                 715                 720

Ser Phe Cys Gln Asp Asn Glu Leu Glu Cys Ala Asn His Glu Cys Val
            725                 730                 735

Pro Arg Asp Leu Trp Cys Asp Gly Trp Val Asp Cys Ser Asp Ser Ser
            740                 745                 750

Asp Glu Trp Gly Cys Val Thr Leu Ser Lys Asn Gly Asn Ser Ser Ser
            755                 760                 765

Leu Leu Thr Val His Lys Ser Ala Lys Glu His His Val Cys Ala Asp
770                 775                 780

Gly Trp Arg Glu Thr Leu Ser Gln Leu Ala Cys Lys Gln Met Gly Leu
785                 790                 795                 800

Gly Glu Pro Ser Val Thr Lys Leu Ile Pro Gly Gln Glu Gly Gln Gln
            805                 810                 815

Trp Leu Arg Leu Tyr Pro Asn Trp Glu Asn Leu Asn Gly Ser Thr Leu
            820                 825                 830

Gln Glu Leu Leu Val Tyr Arg His Ser Cys Pro Ser Arg Ser Glu Ile
            835                 840                 845

Ser Leu Leu Cys Ser Lys Gln Asp Cys Gly Arg Arg Pro Ala Ala Arg
850                 855                 860

Met Asn Lys Arg Ile Leu Gly Gly Arg Thr Ser Arg Pro Gly Arg Trp
865                 870                 875                 880

Pro Trp Gln Cys Ser Leu Gln Ser Glu Pro Ser Gly His Ile Cys Gly
            885                 890                 895

Cys Val Leu Ile Ala Lys Lys Trp Val Leu Thr Val Ala His Cys Phe
            900                 905                 910

Glu Gly Arg Glu Asp Ala Asp Val Trp Lys Val Val Phe Gly Ile Asn
            915                 920                 925

Asn Leu Asp His Pro Ser Gly Phe Met Gln Thr Arg Phe Val Lys Thr
            930                 935                 940

Ile Leu Leu His Pro Arg Tyr Ser Arg Ala Val Val Asp Tyr Asp Ile
945                 950                 955                 960

Ser Val Val Glu Leu Ser Asp Asp Ile Asn Glu Thr Ser Tyr Val Arg
            965                 970                 975

Pro Val Cys Leu Pro Ser Pro Glu Glu Tyr Leu Glu Pro Asp Thr Tyr
            980                 985                 990

Cys Tyr Ile Thr Gly Trp Gly His Met Gly Asn Lys Met Pro Phe Lys
            995                 1000                1005

Leu Gln Glu Gly Glu Val Arg Ile Ile Pro Leu Glu Gln Cys Gln Ser
            1010                1015                1020

Tyr Phe Asp Met Lys Thr Ile Thr Asn Arg Met Ile Cys Ala Gly Tyr
1025                1030                1035                1040

Glu Ser Gly Thr Val Asp Ser Cys Met Gly Asp Ser Gly Gly Pro Leu

```
              1045                1050                1055
Val Cys Glu Arg Pro Gly Gly Gln Trp Thr Leu Phe Gly Leu Thr Ser
            1060                1065                1070

Trp Gly Ser Val Cys Phe Ser Lys Val Leu Gly Pro Gly Val Tyr Ser
        1075                1080                1085

Asn Val Ser Tyr Phe Val Gly Trp Ile Glu Arg Gln Ile Tyr Ile Gln
    1090                1095                1100

Thr Phe Leu Gln Lys Lys Ser Gln Gly
1105                1110

<210> SEQ ID NO 4
<211> LENGTH: 1848
<212> TYPE: PRT
<213> ORGANISM: Homo sapiens

<400> SEQUENCE: 4

Met Arg Arg Gln Trp Gly Ala Leu Leu Gly Ala Leu Leu Cys Ala
 1               5                  10                  15

His Val Leu Pro Thr Cys Ser Pro Leu Asp Phe His Cys Asp Asn Gly
            20                  25                  30

Lys Cys Ile Arg Arg Ser Trp Val Cys Asp Gly Asp Asn Asp Cys Glu
        35                  40                  45

Asp Asp Ser Asp Glu Gln Asp Cys Pro Pro Arg Glu Cys Glu Glu Asp
    50                  55                  60

Glu Phe Pro Cys Gln Asn Gly Tyr Cys Ile Arg Ser Leu Trp His Cys
65                  70                  75                  80

Asp Gly Asp Asn Asp Cys Gly Asp Asn Ser Asp Glu Gln Cys Asp Met
                85                  90                  95

Arg Lys Cys Ser Asp Lys Glu Phe Arg Cys Ser Asp Gly Ser Cys Ile
            100                 105                 110

Ala Glu His Trp Tyr Cys Asp Gly Asp Thr Asp Cys Lys Asp Gly Ser
        115                 120                 125

Asp Glu Glu Asn Cys Pro Ser Ala Val Pro Ala Pro Pro Cys Asn Leu
    130                 135                 140

Glu Glu Phe Gln Cys Ala Tyr Gly Arg Cys Ile Leu Asp Ile Tyr His
145                 150                 155                 160

Cys Asp Gly Asp Asp Cys Gly Asp Trp Ser Asp Glu Ser Asp Cys
                165                 170                 175

Cys Glu Tyr Ser Gly Gln Leu Gly Ala Ser His Gln Pro Cys Arg Ser
            180                 185                 190

Gly Glu Phe Met Cys Asp Ser Gly Leu Cys Ile Asn Ala Gly Trp Arg
        195                 200                 205

Cys Asp Gly Asp Ala Asp Cys Asp Asp Gln Ser Asp Glu Arg Asn Cys
    210                 215                 220

Lys Gln Phe Arg Cys His Ser Gly Arg Cys Val Arg Leu Ser Trp Arg
225                 230                 235                 240

Cys Asp Gly Glu Asp Asp Cys Ala Asp Asn Ser Asp Glu Glu Asn Cys
                245                 250                 255

Glu Asn Thr Gly Ser Pro Gln Cys Ala Leu Asp Gln Phe Leu Cys Trp
            260                 265                 270

Asn Gly Arg Cys Ile Gly Gln Arg Lys Leu Cys Asn Gly Val Asn Asp
        275                 280                 285

Cys Gly Asp Asn Ser Asp Glu Ser Pro Gln Gln Asn Cys Arg Pro Arg
    290                 295                 300
```

```
Thr Gly Glu Glu Asn Cys Asn Val Asn Asn Gly Cys Ala Gln Lys
305                 310                 315                 320

Cys Gln Met Val Arg Gly Ala Val Gln Cys Thr Cys His Thr Gly Tyr
            325                 330                 335

Arg Leu Thr Glu Asp Gly His Thr Cys Gln Asp Val Asn Glu Cys Ala
            340                 345                 350

Glu Glu Gly Tyr Cys Ser Gln Gly Cys Thr Asn Ser Glu Gly Ala Phe
                355                 360                 365

Gln Cys Trp Cys Glu Thr Gly Tyr Glu Leu Arg Pro Asp Arg Arg Ser
        370                 375                 380

Cys Lys Ala Leu Gly Pro Glu Pro Val Leu Leu Phe Ala Asn Arg Ile
385                 390                 395                 400

Asp Ile Arg Gln Val Leu Pro His Arg Ser Glu Tyr Thr Leu Leu Leu
                405                 410                 415

Asn Asn Leu Glu Asn Ala Ile Ala Leu Asp Phe His His Arg Arg Glu
                420                 425                 430

Leu Val Phe Trp Ser Asp Val Thr Leu Asp Arg Ile Leu Arg Ala Asn
            435                 440                 445

Leu Asn Gly Ser Asn Val Glu Glu Val Val Ser Thr Gly Leu Glu Ser
450                 455                 460

Pro Gly Gly Leu Ala Val Asp Trp Val His Asp Lys Leu Tyr Trp Thr
465                 470                 475                 480

Asp Ser Gly Thr Ser Arg Ile Glu Val Ala Asn Leu Asp Gly Ala His
                485                 490                 495

Arg Lys Val Leu Leu Trp Gln Asn Leu Glu Lys Pro Arg Ala Ile Ala
            500                 505                 510

Leu His Pro Met Glu Gly Thr Ile Tyr Trp Thr Asp Trp Gly Asn Thr
            515                 520                 525

Pro Arg Ile Glu Ala Ser Ser Met Asp Gly Ser Gly Arg Arg Ile Ile
530                 535                 540

Ala Asp Thr His Leu Phe Trp Pro Asn Gly Leu Thr Ile Asp Tyr Ala
545                 550                 555                 560

Gly Arg Arg Met Tyr Trp Val Asp Ala Lys His His Val Ile Glu Arg
                565                 570                 575

Ala Asn Leu Asp Gly Ser His Arg Lys Ala Val Ile Ser Gln Val Phe
            580                 585                 590

Glu Asp Ser Leu Tyr Trp Thr Asp Trp His Thr Lys Ser Ile Asn Ser
        595                 600                 605

Ala Asn Lys Phe Thr Gly Lys Asn Gln Glu Ile Ile Arg Asn Lys Leu
610                 615                 620

His Phe Pro Met Asp Ile His Thr Leu His Pro Gln Arg Gln Pro Ala
625                 630                 635                 640

Gly Lys Asn Arg Cys Gly Asp Asn Asn Gly Gly Cys Thr His Leu Cys
            645                 650                 655

Leu Pro Ser Gly Gln Asn Tyr Thr Cys Ala Cys Pro Thr Gly Phe Arg
                660                 665                 670

Lys Ile Ser Ser His Ala Cys Ala Gln Ser Leu Asp Lys Phe Leu Leu
            675                 680                 685

Phe Ala Arg Arg Met Asp Ile Arg Ile Ser Phe Asp Thr Glu Asp
        690                 695                 700

Leu Ser Asp Asp Val Ile Pro Leu Ala Asp Val Arg Ser Ala Val Ala
705                 710                 715                 720

Leu Asp Trp Asp Ser Arg Asp Asp His Val Tyr Trp Thr Asp Val Ser
```

```
                        725                 730                 735
Thr Asp Thr Ile Ser Arg Ala Lys Trp Asp Gly Thr Gly Gln Glu Val
                    740                 745                 750
Val Val Asp Thr Ser Leu Glu Ser Pro Ala Gly Leu Ala Ile Asp Trp
                755                 760                 765
Val Thr Asn Lys Leu Tyr Trp Thr Asp Ala Gly Thr Asp Arg Ile Glu
            770                 775                 780
Val Ala Asn Thr Asp Gly Ser Met Arg Thr Val Leu Ile Trp Glu Asn
785                 790                 795                 800
Leu Asp Arg Pro Arg Asp Ile Val Glu Pro Met Gly Gly Tyr Met
                805                 810                 815
Tyr Trp Thr Asp Trp Gly Ala Ser Pro Lys Ile Glu Arg Ala Gly Met
                820                 825                 830
Asp Ala Ser Gly Arg Gln Val Ile Ile Ser Ser Asn Leu Thr Trp Pro
                835                 840                 845
Asn Gly Leu Ala Ile Asp Tyr Gly Ser Gln Arg Leu Tyr Trp Ala Asp
            850                 855                 860
Ala Gly Met Lys Thr Ile Glu Phe Ala Gly Leu Asp Gly Ser Lys Arg
865                 870                 875                 880
Lys Val Leu Ile Gly Ser Gln Leu Pro His Pro Phe Gly Leu Thr Leu
                885                 890                 895
Tyr Gly Glu Arg Ile Tyr Trp Thr Asp Trp Gln Thr Lys Ser Ile Gln
                900                 905                 910
Ser Ala Asp Arg Leu Thr Gly Leu Asp Arg Glu Thr Leu Gln Glu Asn
            915                 920                 925
Leu Glu Asn Leu Met Asp Ile His Val Phe His Arg Arg Pro Pro
930                 935                 940
Val Ser Thr Pro Cys Ala Met Glu Asn Gly Gly Cys Ser His Leu Cys
945                 950                 955                 960
Leu Arg Ser Pro Asn Pro Ser Gly Phe Ser Cys Thr Cys Pro Thr Gly
                965                 970                 975
Ile Asn Leu Leu Ser Asp Gly Lys Thr Cys Ser Pro Gly Met Asn Ser
            980                 985                 990
Phe Leu Ile Phe Ala Arg Arg Ile Asp Ile Arg Met Val Ser Leu Asp
        995                 1000                1005
Ile Pro Tyr Phe Ala Asp Val Val Pro Ile Asn Ile Thr Met Lys
    1010                1015                1020
Asn Thr Ile Ala Ile Gly Val Asp Pro Gln Glu Gly Lys Val Tyr Trp
1025                1030                1035                1040
Ser Asp Ser Thr Leu His Arg Ile Ser Arg Ala Asn Leu Asp Gly Ser
                1045                1050                1055
Gln His Glu Asp Ile Ile Thr Thr Gly Leu Gln Thr Asp Gly Leu
            1060                1065                1070
Ala Val Asp Ala Ile Gly Arg Lys Val Tyr Trp Thr Asp Thr Gly Thr
            1075                1080                1085
Asn Arg Ile Glu Val Gly Asn Leu Asp Gly Ser Met Arg Lys Val Leu
    1090                1095                1100
Val Trp Gln Asn Leu Asp Ser Pro Arg Ala Ile Val Leu Tyr His Glu
1105                1110                1115                1120
Met Gly Phe Met Tyr Trp Thr Asp Trp Gly Glu Asn Ala Lys Leu Glu
                1125                1130                1135
Arg Ser Gly Met Asp Gly Ser Asp Arg Ala Val Leu Ile Asn Asn Asn
                1140                1145                1150
```

```
Leu Gly Trp Pro Asn Gly Leu Thr Val Asp Lys Ala Ser Ser Gln Leu
        1155                1160                1165

Leu Trp Ala Asp Ala His Thr Glu Arg Ile Glu Ala Ala Asp Leu Asn
    1170                1175                1180

Gly Ala Asn Arg His Thr Leu Val Ser Pro Val Gln His Pro Tyr Gly
1185                1190                1195                1200

Leu Thr Leu Leu Asp Ser Tyr Ile Tyr Trp Thr Asp Trp Gln Thr Arg
            1205                1210                1215

Ser Ile His Arg Ala Asp Lys Gly Thr Gly Ser Asn Val Ile Leu Val
                1220                1225                1230

Arg Ser Asn Leu Pro Gly Leu Met Asp Met Gln Ala Val Asp Arg Ala
            1235                1240                1245

Gln Pro Leu Gly Phe Asn Lys Cys Gly Ser Arg Asn Gly Gly Cys Ser
        1250                1255                1260

His Leu Cys Leu Pro Arg Pro Ser Gly Phe Ser Cys Ala Cys Pro Thr
1265                1270                1275                1280

Gly Ile Gln Leu Lys Gly Asp Gly Lys Thr Cys Asp Pro Ser Pro Glu
            1285                1290                1295

Thr Tyr Leu Leu Phe Ser Ser Arg Gly Ser Ile Arg Arg Ile Ser Leu
        1300                1305                1310

Asp Thr Ser Asp His Thr Asp Val His Val Pro Val Pro Glu Leu Asn
            1315                1320                1325

Asn Val Ile Ser Leu Asp Tyr Asp Ser Val Asp Gly Lys Val Tyr Tyr
        1330                1335                1340

Thr Asp Val Phe Leu Asp Val Ile Arg Arg Ala Asp Leu Asn Gly Ser
1345                1350                1355                1360

Asn Met Glu Thr Val Ile Gly Arg Gly Leu Lys Thr Thr Asp Gly Leu
            1365                1370                1375

Ala Val Asp Trp Val Ala Arg Asn Leu Tyr Trp Thr Asp Thr Gly Arg
        1380                1385                1390

Asn Thr Ile Glu Ala Ser Arg Leu Asp Gly Ser Cys Arg Lys Val Leu
            1395                1400                1405

Ile Asn Asn Ser Leu Asp Glu Pro Arg Ala Ile Ala Val Phe Pro Arg
        1410                1415                1420

Lys Gly Tyr Leu Phe Trp Thr Asp Trp Gly His Ile Ala Lys Ile Glu
1425                1430                1435                1440

Arg Ala Asn Leu Asp Gly Ser Glu Arg Lys Val Leu Ile Asn Thr Asp
            1445                1450                1455

Leu Gly Trp Pro Asn Gly Leu Thr Leu Asp Tyr Asp Thr Arg Arg Ile
            1460                1465                1470

Tyr Trp Val Asp Ala His Leu Asp Arg Ile Glu Ser Ala Asp Leu Asn
        1475                1480                1485

Gly Lys Leu Arg Gln Val Leu Val Ser His Val Ser His Pro Phe Ala
        1490                1495                1500

Leu Thr Gln Gln Asp Arg Trp Ile Tyr Trp Thr Asp Trp Gln Thr Lys
1505                1510                1515                1520

Ser Ile Gln Arg Val Asp Lys Tyr Ser Gly Arg Asn Lys Glu Thr Val
            1525                1530                1535

Leu Ala Asn Val Glu Gly Leu Met Asp Ile Ile Val Val Ser Pro Gln
            1540                1545                1550

Arg Gln Thr Gly Thr Asn Ala Cys Gly Val Asn Asn Gly Gly Cys Thr
        1555                1560                1565
```

His Leu Cys Phe Ala Arg Ala Ser Asp Phe Val Cys Ala Cys Pro Asp
    1570                1575                1580

Glu Pro Asp Ser Arg Pro Cys Ser Leu Val Pro Gly Leu Val Pro Pro
1585                1590                1595                1600

Ala Pro Arg Ala Thr Gly Met Ser Glu Lys Ser Pro Val Leu Pro Asn
            1605                1610                1615

Thr Pro Pro Thr Thr Leu Tyr Ser Ser Thr Thr Arg Thr Arg Thr Ser
        1620                1625                1630

Leu Glu Glu Val Glu Gly Arg Cys Ser Glu Arg Asp Ala Arg Leu Gly
    1635                1640                1645

Leu Cys Ala Arg Ser Asn Asp Ala Val Pro Ala Pro Gly Glu Gly
1650                1655                1660

Leu His Ile Ser Tyr Ala Ile Gly Gly Leu Leu Ser Ile Leu Leu Ile
1665            1670                1675                1680

Leu Val Val Ile Ala Ala Leu Met Leu Tyr Arg His Lys Lys Ser Lys
            1685                1690                1695

Phe Thr Asp Pro Gly Met Gly Asn Leu Thr Tyr Ser Asn Pro Ser Tyr
        1700                1705                1710

Arg Thr Ser Thr Gln Glu Val Lys Ile Glu Ala Ile Pro Lys Pro Ala
    1715                1720                1725

Met Tyr Asn Gln Leu Cys Tyr Lys Lys Glu Gly Gly Pro Asp His Asn
1730                1735                1740

Tyr Thr Lys Glu Lys Ile Lys Ile Val Glu Gly Ile Cys Leu Leu Ser
1745                1750                1755                1760

Gly Asp Asp Ala Glu Trp Asp Asp Leu Lys Gln Leu Arg Ser Ser Arg
            1765                1770                1775

Gly Gly Leu Leu Arg Asp His Val Cys Met Lys Thr Asp Thr Val Ser
        1780                1785                1790

Ile Gln Ala Ser Ser Gly Ser Leu Asp Asp Thr Glu Thr Glu Gln Leu
    1795                1800                1805

Leu Gln Glu Glu Gln Ser Glu Cys Ser Ser Val His Thr Ala Ala Thr
        1810                1815                1820

Pro Glu Arg Arg Gly Ser Leu Pro Asp Thr Gly Trp Lys His Glu Arg
1825                1830                1835                1840

Lys Leu Ser Ser Glu Ser Gln Val
            1845

<210> SEQ ID NO 5
<211> LENGTH: 26
<212> TYPE: DNA
<213> ORGANISM: Artificial Sequence
<220> FEATURE:
<223> OTHER INFORMATION: An artificially synthesized adaptor sequence.

<400> SEQUENCE: 5
cagctccaca acctacatca ttccgt                                      26

<210> SEQ ID NO 6
<211> LENGTH: 12
<212> TYPE: DNA
<213> ORGANISM: Artificial Sequence
<220> FEATURE:
<223> OTHER INFORMATION: An artificially synthesized adaptor sequence.

<400> SEQUENCE: 6
acggaatgat gt                                                     12

```
<210> SEQ ID NO 7
<211> LENGTH: 26
<212> TYPE: DNA
<213> ORGANISM: Artificial Sequence
<220> FEATURE:
<223> OTHER INFORMATION: An artificially synthesized adaptor sequence.

<400> SEQUENCE: 7
gtccatcttc tctctgagac tctggt                                          26

<210> SEQ ID NO 8
<211> LENGTH: 12
<212> TYPE: DNA
<213> ORGANISM: Artificial Sequence
<220> FEATURE:
<223> OTHER INFORMATION: An artificially synthesized adaptor sequence.

<400> SEQUENCE: 8
accagagtct ca                                                         12

<210> SEQ ID NO 9
<211> LENGTH: 26
<212> TYPE: DNA
<213> ORGANISM: Artificial Sequence
<220> FEATURE:
<223> OTHER INFORMATION: An artificially synthesized adaptor sequence.

<400> SEQUENCE: 9
ctgatgggtg tcttctgtga gtgtgt                                          26

<210> SEQ ID NO 10
<211> LENGTH: 12
<212> TYPE: DNA
<213> ORGANISM: Artificial Sequence
<220> FEATURE:
<223> OTHER INFORMATION: An artificially synthesized adaptor sequence.

<400> SEQUENCE: 10
acacactcac ag                                                         12

<210> SEQ ID NO 11
<211> LENGTH: 26
<212> TYPE: DNA
<213> ORGANISM: Artificial Sequence
<220> FEATURE:
<223> OTHER INFORMATION: An artificially synthesized adaptor sequence.

<400> SEQUENCE: 11
ccagcatcga gaatcagtgt gacagt                                          26

<210> SEQ ID NO 12
<211> LENGTH: 12
<212> TYPE: DNA
<213> ORGANISM: Artificial Sequence
<220> FEATURE:
<223> OTHER INFORMATION: An artificially synthesized adaptor sequence.

<400> SEQUENCE: 12
actgtcacac tg                                                         12

<210> SEQ ID NO 13
<211> LENGTH: 26
<212> TYPE: DNA
<213> ORGANISM: Artificial Sequence
<220> FEATURE:
<223> OTHER INFORMATION: An artificially synthesized adaptor sequence.
```

<400> SEQUENCE: 13
gtcgatgaac ttcgactgtc gatcgt                                              26

<210> SEQ ID NO 14
<211> LENGTH: 12
<212> TYPE: DNA
<213> ORGANISM: Artificial Sequence
<220> FEATURE:
<223> OTHER INFORMATION: An artificially synthesized adaptor sequence.

<400> SEQUENCE: 14
acgatcgaca gt                                                             12

<210> SEQ ID NO 15
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 15
tagtctacca ctgctcgact gtaacg                                              26

<210> SEQ ID NO 16
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 16
cagagtgaac ccagtggaca tatctg                                              26

<210> SEQ ID NO 17
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 17
gttcccaagg aaagtgtcag agttgg                                              26

<210> SEQ ID NO 18
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 18
gaagctggaa agcctccagg tgttcc                                              26

<210> SEQ ID NO 19
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 19
ctccgagcag acaccatgac cttagc                                              26

<210> SEQ ID NO 20
<211> LENGTH: 26

```
<212> TYPE: DNA
<213> ORGANISM: Artificial Sequence
<220> FEATURE:
<223> OTHER INFORMATION: An artificially synthesized primer sequence.

<400> SEQUENCE: 20
aggagtaggg cttgtctccc aacctg                                          26

<210> SEQ ID NO 21
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 21
cactcctgtg tctagctgcc agatgc                                          26

<210> SEQ ID NO 22
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 22
agtgcgaaca ccgtagtgct gacagg                                          26

<210> SEQ ID NO 23
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 23
gatgaagaag aaggagcaga gtcagg                                          26

<210> SEQ ID NO 24
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 24
attcacttgc tctgactcca ggttgg                                          26

<210> SEQ ID NO 25
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 25
ccatgatctt tccsctctgg cttctg                                          26

<210> SEQ ID NO 26
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 26
```

```
tttggctgga aagggtgact ctgagg                                          26

<210> SEQ ID NO 27
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 27
tgctctcacc atccagatga ctcacc                                          26

<210> SEQ ID NO 28
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 28
tggaccatat ctgctgcaac tggtcc                                          26

<210> SEQ ID NO 29
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 29
tccagcagat gcaagaactc tcctcc                                          26

<210> SEQ ID NO 30
<211> LENGTH: 26
<212> TYPE: DNA
<213> ORGANISM: Artificial Sequence
<220> FEATURE:
<223> OTHER INFORMATION: An artificially synthesized primer sequence.

<400> SEQUENCE: 30
ttatggagcg gagcagcatt ccaagg                                          26
```